US009173602B2

(12) United States Patent
Gilbert

(10) Patent No.: US 9,173,602 B2
(45) Date of Patent: Nov. 3, 2015

(54) FLUID CHARACTERISTIC MEASUREMENT

(76) Inventor: Paul J. Gilbert, Payson, AZ (US)

( * ) Notice: Subject to any disclaimer, the term of this patent is extended or adjusted under 35 U.S.C. 154(b) by 189 days.

(21) Appl. No.: 13/589,686

(22) Filed: Aug. 20, 2012

(65) Prior Publication Data

US 2012/0316415 A1 Dec. 13, 2012

Related U.S. Application Data

(63) Continuation-in-part of application No. 12/925,783, filed on Oct. 29, 2010, which is a continuation-in-part of application No. 12/799,123, filed on Apr. 19, 2010, now abandoned, which is a continuation of application No. 11/769,597, filed on Jun. 27, 2007, now Pat. No. 7,699,818, which is a continuation-in-part of application No. 11/548,086, filed on Oct. 10, 2006, now Pat. No. 7,740,620, which is a continuation-in-part of application No. 11/347,481, filed on Feb. 3, 2006, now Pat. No. 7,695,459.

(60) Provisional application No. 61/524,878, filed on Aug. 18, 2011, provisional application No. 60/650,806, filed on Feb. 8, 2005.

(51) Int. Cl.
| | |
|---|---|
| *A61B 5/145* | (2006.01) |
| *A61B 5/00* | (2006.01) |
| *A61B 5/1473* | (2006.01) |
| *A61B 5/155* | (2006.01) |
| *A61B 5/157* | (2006.01) |
| *A61B 10/00* | (2006.01) |
| *A61M 25/09* | (2006.01) |
| *A61B 19/00* | (2006.01) |
| *A61M 25/01* | (2006.01) |

(52) U.S. Cl.
CPC .......... *A61B 5/14539* (2013.01); *A61B 5/1473* (2013.01); *A61B 5/6852* (2013.01); *A61B 5/1427* (2013.01); *A61B 5/157* (2013.01); *A61B 10/007* (2013.01); *A61B 2010/0061* (2013.01); *A61B 2019/4836* (2013.01); *A61M 25/09* (2013.01); *A61M 2025/0166* (2013.01); *A61M 2025/09008* (2013.01); *A61M 2025/09183* (2013.01); *A61M 2205/3324* (2013.01)

(58) Field of Classification Search
CPC .... A61J 15/003; A61J 15/0026; G01N 31/22; A61B 5/157; A61B 5/1427; A61B 5/14542; A61B 5/14865; A61B 2560/0443; A61B 5/6852; A61B 5/14539; A61F 2007/126; A61M 2230/20
USPC .................................................. 600/584, 593
See application file for complete search history.

(56) References Cited

U.S. PATENT DOCUMENTS

| | | | |
|---|---|---|---|
| 2,657,691 A | | 12/1952 | Nordstrom, Jr. |
| 3,373,735 A | * | 3/1968 | Gallagher ..................... 600/581 |

(Continued)

FOREIGN PATENT DOCUMENTS

| | | |
|---|---|---|
| EP | 0251471 | 1/1988 |
| EP | 1774985 | 4/2007 |

(Continued)

*Primary Examiner* — Max Hindenburg

(57) ABSTRACT

An apparatus comprises a detection indicator, a housing, and an exoskeleton in which the housing nests. The detection indicator is configured to furnish a visual indication upon contact with a fluid responsive to a characteristic of the fluid. The housing comprises an interior chamber configured to receive the fluid and to provide contact between the fluid and the detection indicator. The housing is configured to removably engage a conduit coupled to a source of a fluid sample, which may be a lumen inserted into a patient to receive fluid therefrom. In methods for use with the apparatus, a sample is collected, a characteristic is measured by the apparatus, and the apparatus is disconnected so as to avoid leakage of the sample and exposure of personnel.

28 Claims, 44 Drawing Sheets

(56) References Cited

U.S. PATENT DOCUMENTS

| | | | | |
|---|---|---|---|---|
| 3,395,710 A | | 8/1968 | Stratton et al. | |
| 4,151,832 A | * | 5/1979 | Hamer | 600/578 |
| 4,416,267 A | | 11/1983 | Garren et al. | |
| 4,473,530 A | * | 9/1984 | Villa-Real | 422/408 |
| 4,516,970 A | | 5/1985 | Kaufman et al. | |
| 4,735,214 A | | 4/1988 | Berman | |
| 4,819,619 A | | 4/1989 | Augustine | |
| 4,827,944 A | * | 5/1989 | Nugent | 600/584 |
| 4,879,999 A | | 11/1989 | Leiman et al. | |
| 4,887,997 A | | 12/1989 | Okada | |
| 4,925,446 A | | 5/1990 | Garay et al. | |
| 4,994,117 A | * | 2/1991 | Fehder | 436/133 |
| 4,995,402 A | * | 2/1991 | Smith et al. | 600/584 |
| 5,105,812 A | | 4/1992 | Corman | |
| 5,124,129 A | | 6/1992 | Riccitelli et al. | |
| 5,197,464 A | * | 3/1993 | Babb et al. | 128/207.14 |
| 5,318,530 A | | 6/1994 | Nelson, Jr. | |
| 5,334,167 A | | 8/1994 | Cocanower | |
| 5,339,829 A | * | 8/1994 | Thieme et al. | 600/573 |
| 5,341,803 A | | 8/1994 | Goldberg | |
| 5,360,013 A | * | 11/1994 | Gilbert | 600/584 |
| 5,366,444 A | | 11/1994 | Martin | |
| 5,387,526 A | | 2/1995 | Garner et al. | |
| 5,391,158 A | | 2/1995 | Peters | |
| 5,401,241 A | | 3/1995 | Delany | |
| 5,411,022 A | | 5/1995 | McCue et al. | |
| 5,611,787 A | | 3/1997 | Demeter et al. | |
| 5,891,054 A | | 4/1999 | Metheny et al. | |
| 5,916,176 A | * | 6/1999 | Caillouette | 600/572 |
| 5,951,492 A | * | 9/1999 | Douglas et al. | 600/583 |
| 6,123,075 A | * | 9/2000 | Kirk | 128/205.13 |
| 6,544,474 B2 | | 4/2003 | Douglas | |
| 2003/0109793 A1 | | 6/2003 | Ratner | |
| 2004/0039350 A1 | | 2/2004 | McKittrick | |
| 2006/0060202 A1 | * | 3/2006 | Flynn et al. | 128/207.14 |
| 2006/0189947 A1 | | 8/2006 | Gilbert et al. | |
| 2007/0112317 A1 | | 5/2007 | Gilbert et al. | |
| 2008/0004598 A1 | | 1/2008 | Gilbert | |
| 2009/0198182 A1 | * | 8/2009 | Fujishima et al. | 604/131 |
| 2009/0221885 A1 | | 9/2009 | Hall et al. | |
| 2010/0106097 A1 | | 4/2010 | Elmouelhi | |
| 2011/0077495 A1 | | 3/2011 | Gilbert | |

FOREIGN PATENT DOCUMENTS

| | | |
|---|---|---|
| GB | 2046595 | 11/1980 |
| JP | 2002191552 | 7/2002 |
| WO | 92/21282 | 12/1992 |

* cited by examiner

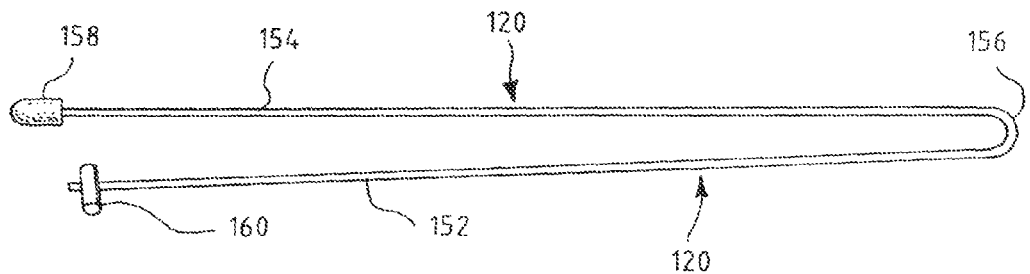
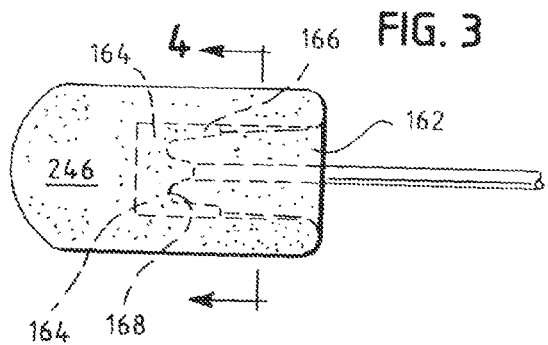
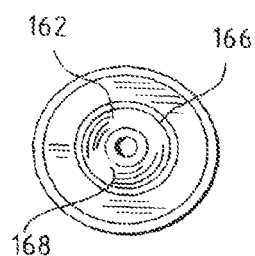
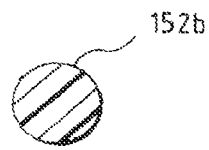
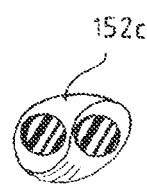
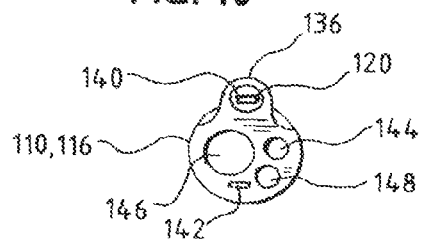

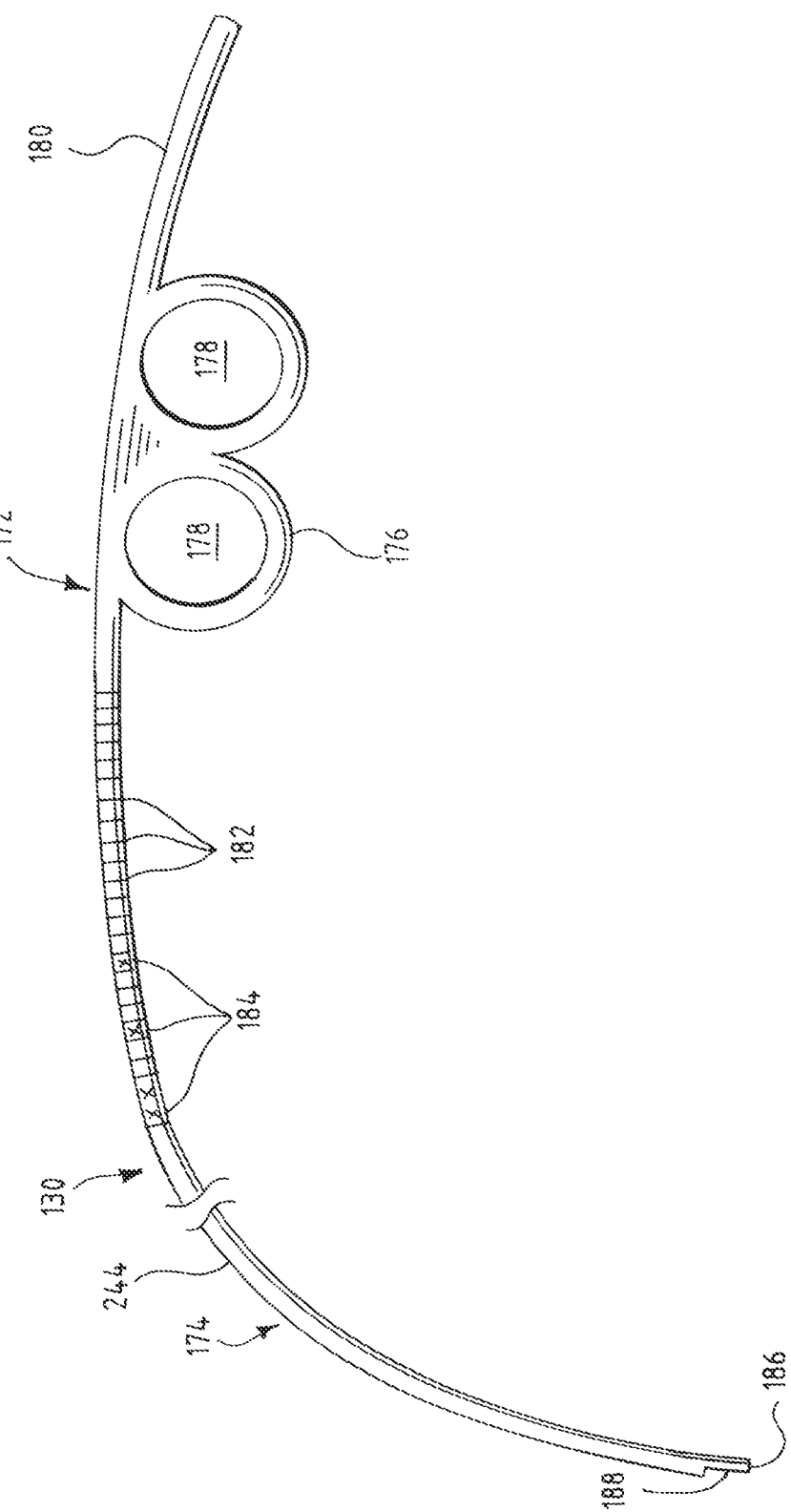

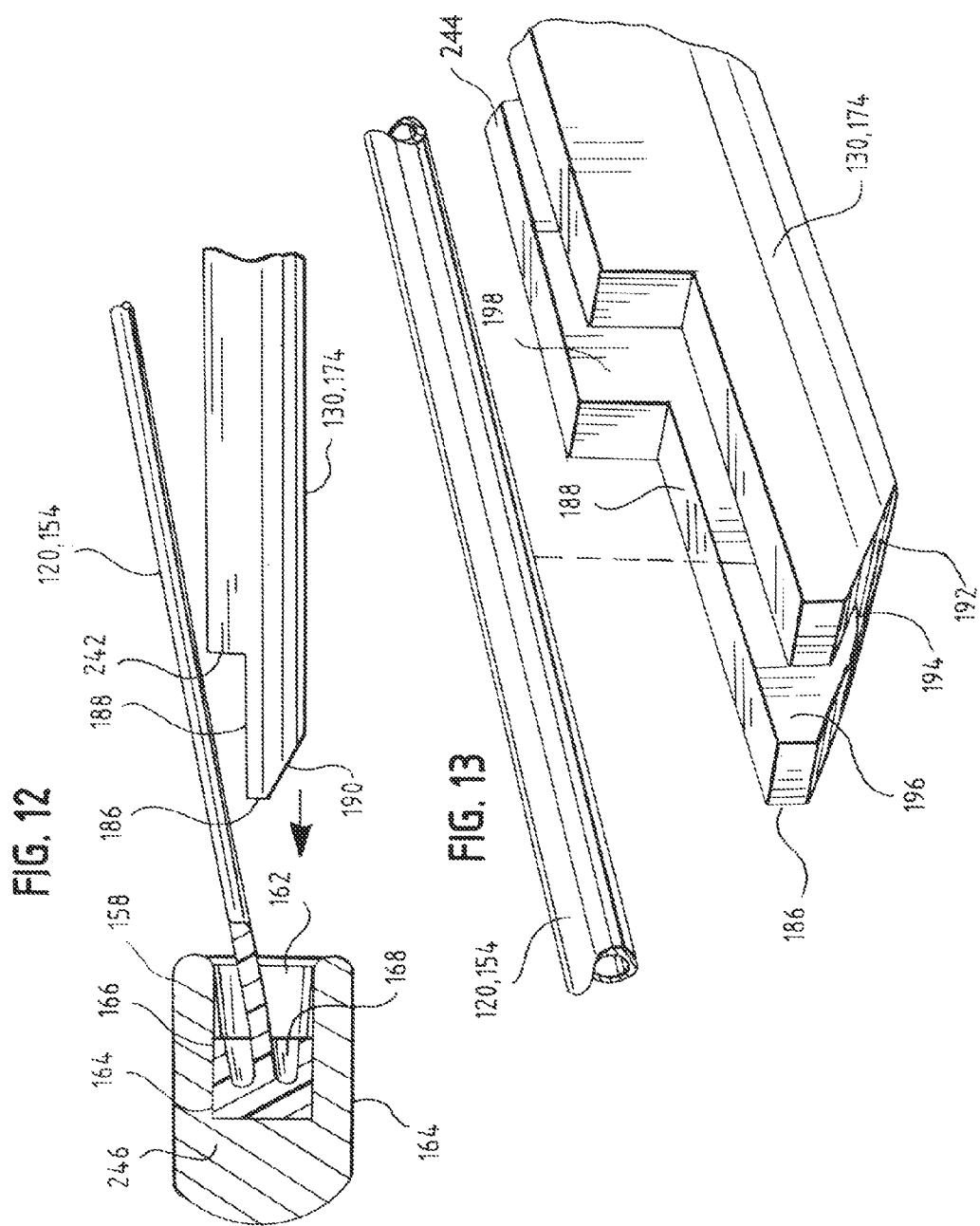

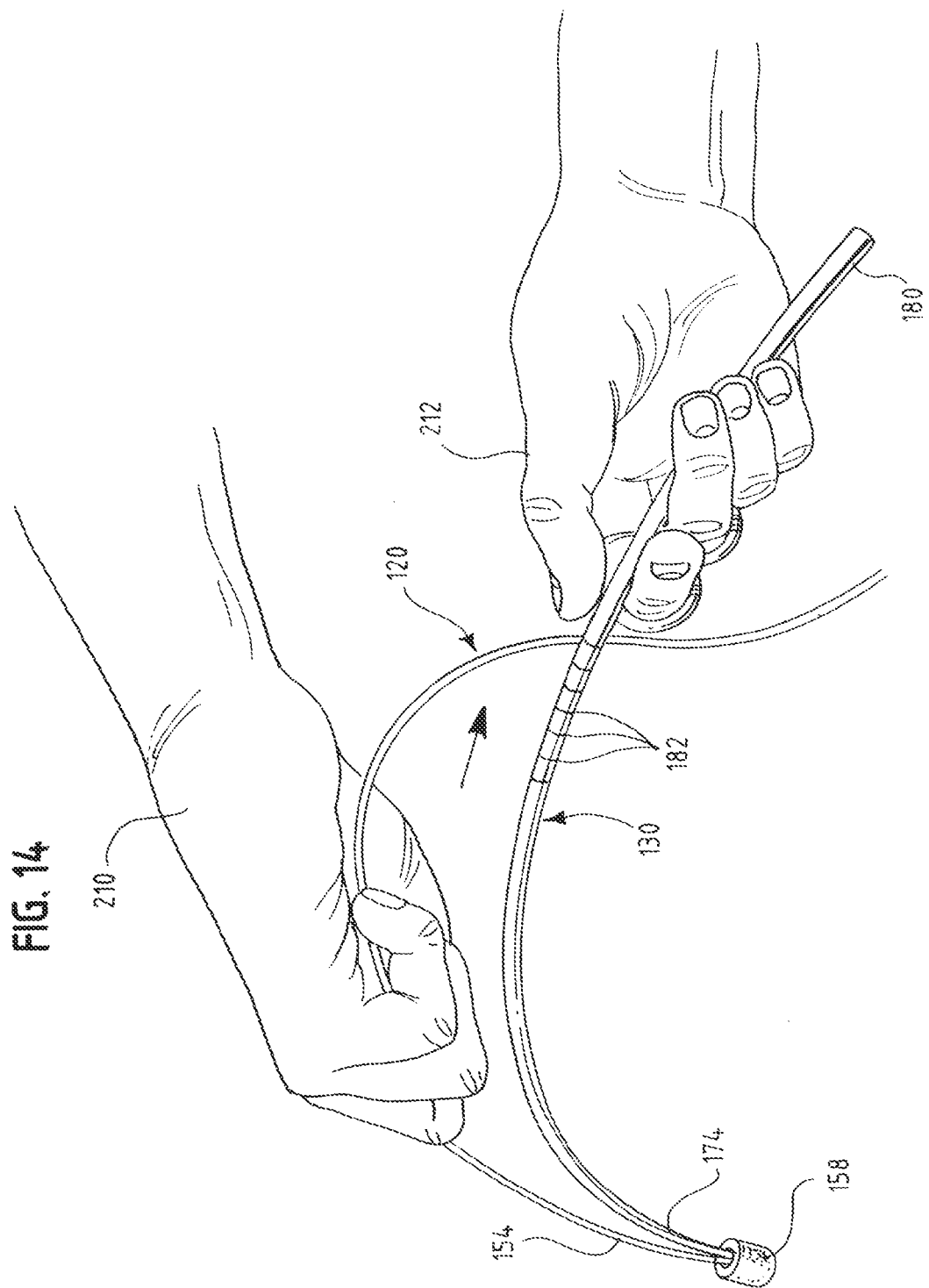

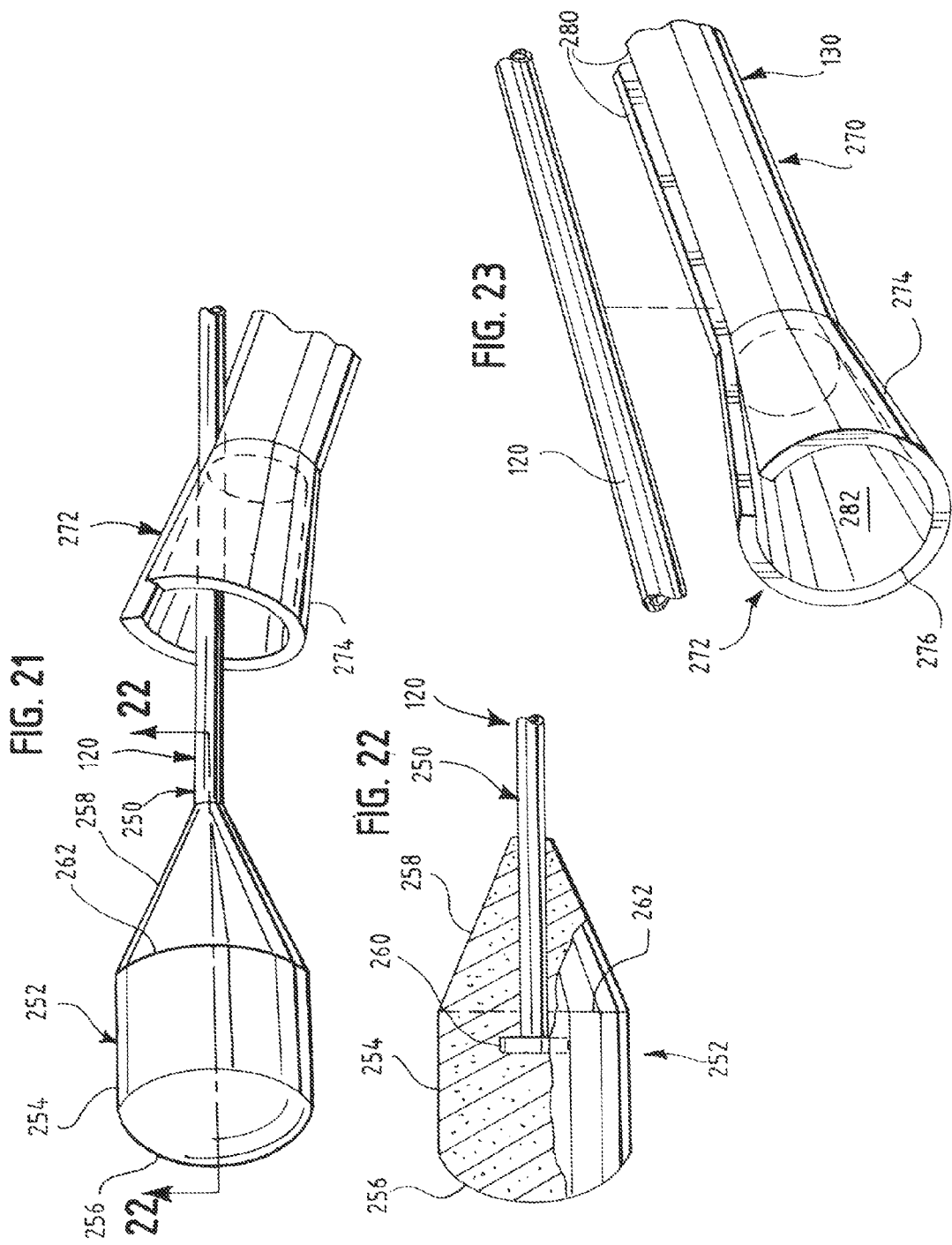

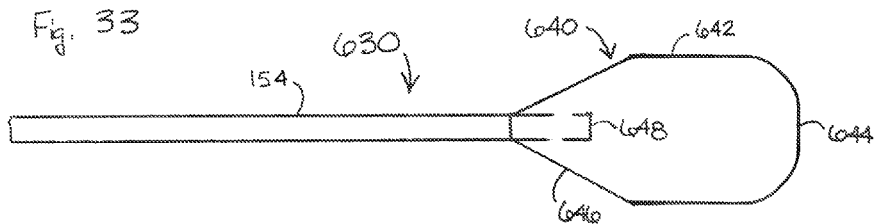
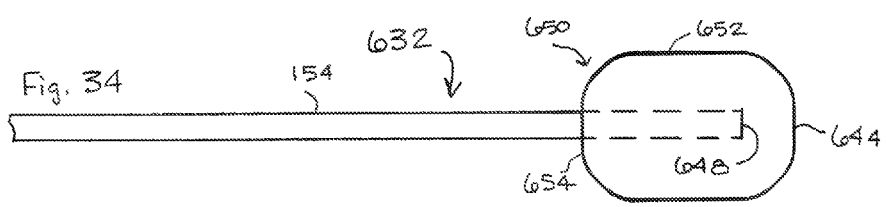
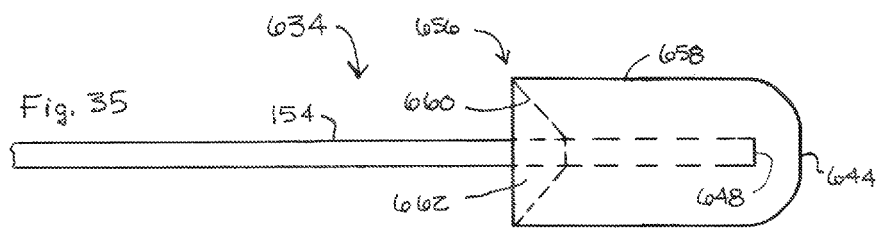
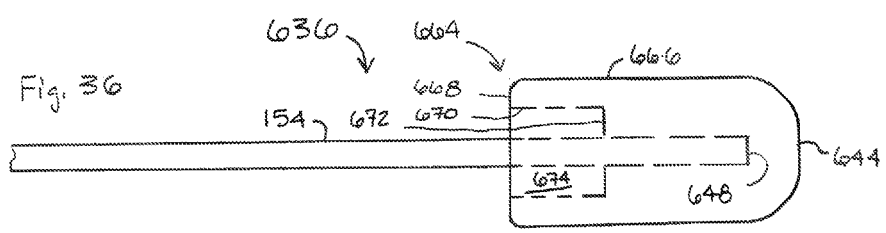
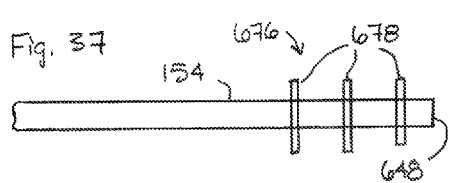
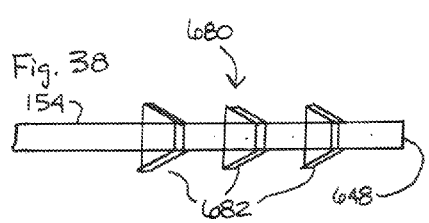

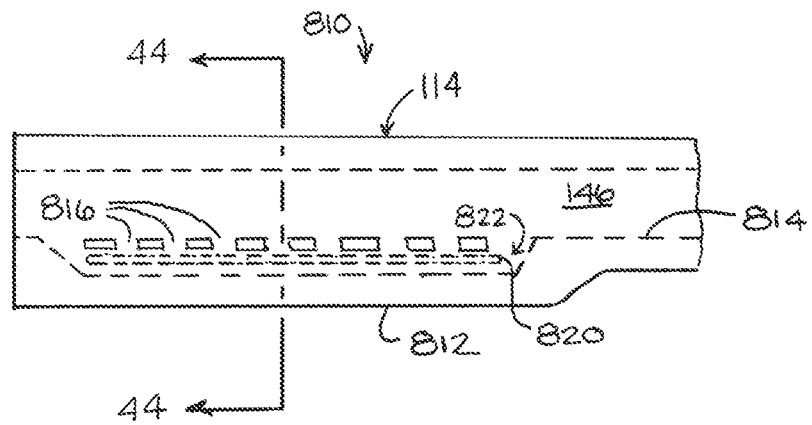
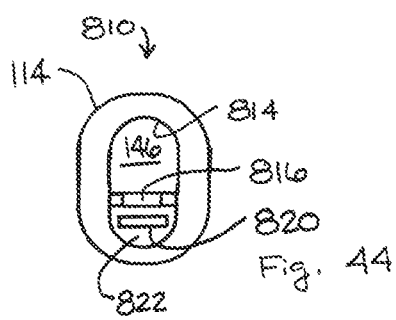
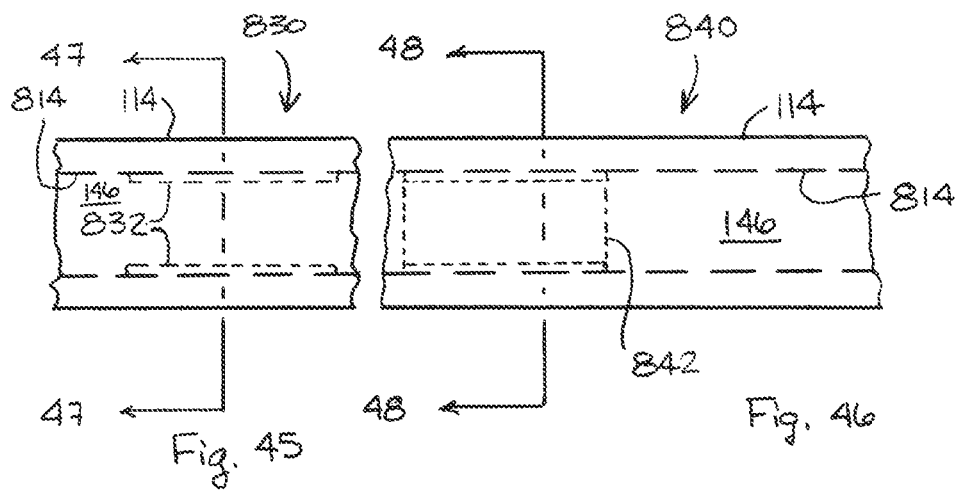
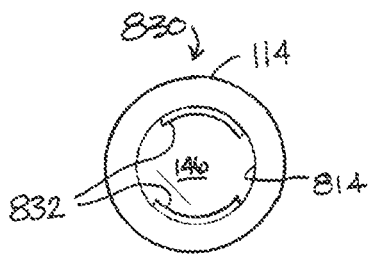
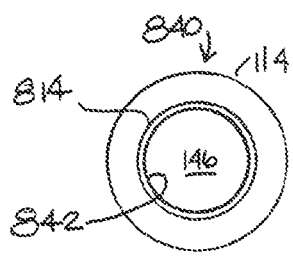

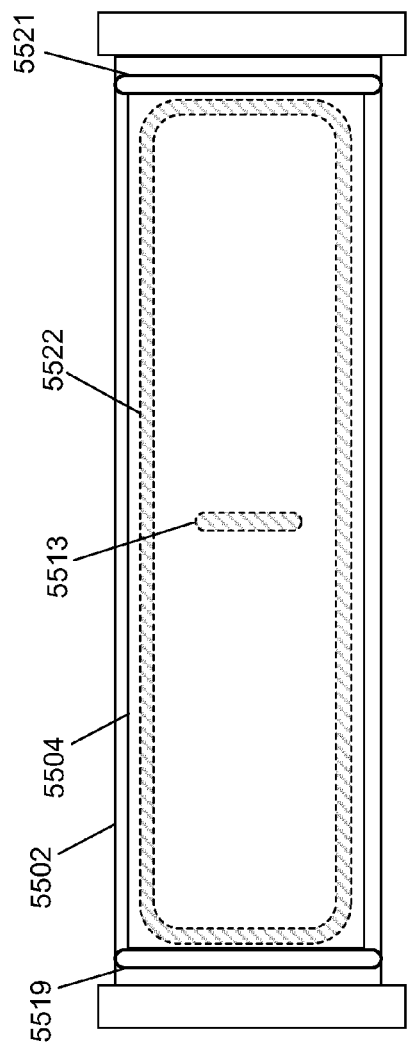
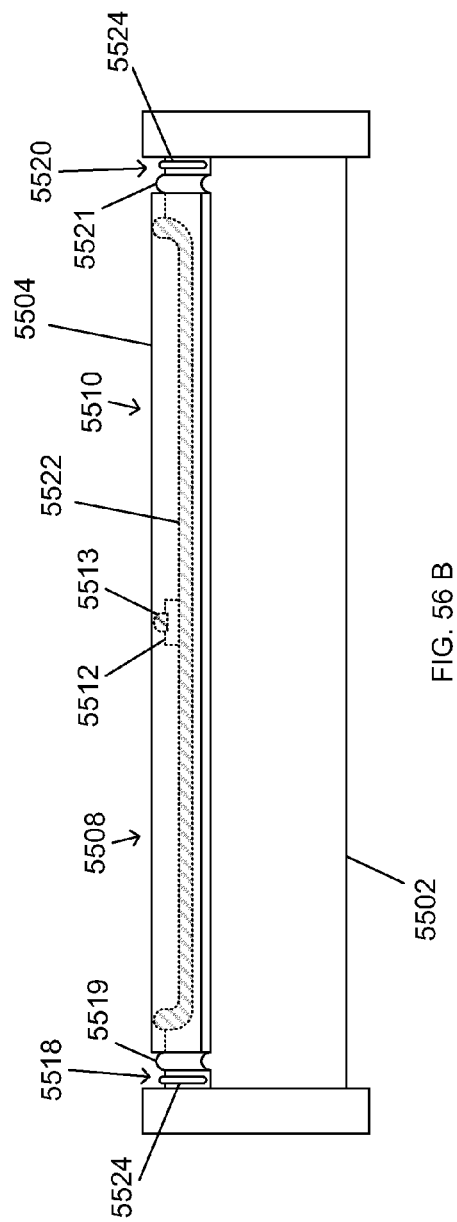
FIG. 56 A
FIG. 56 B

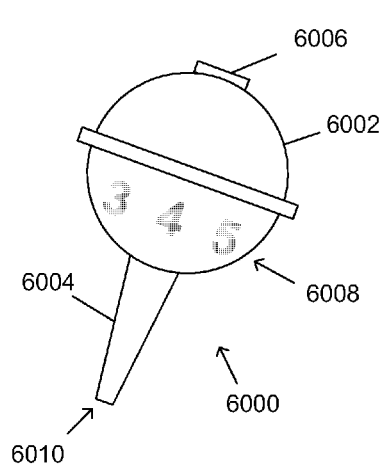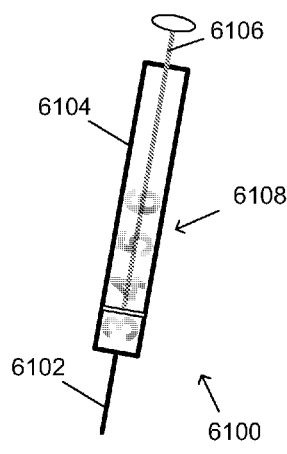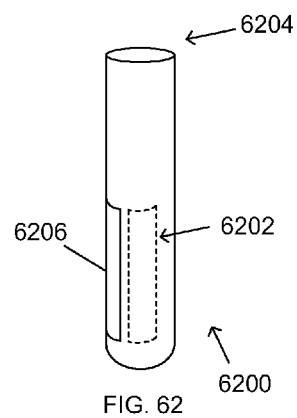
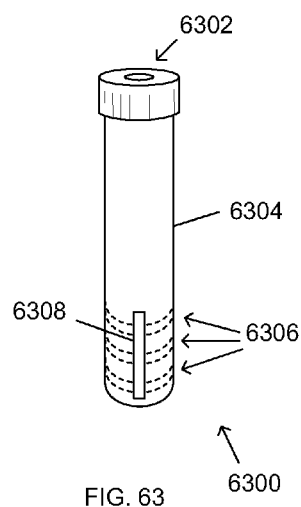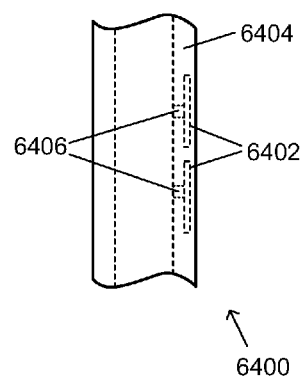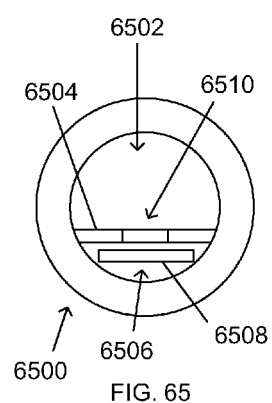

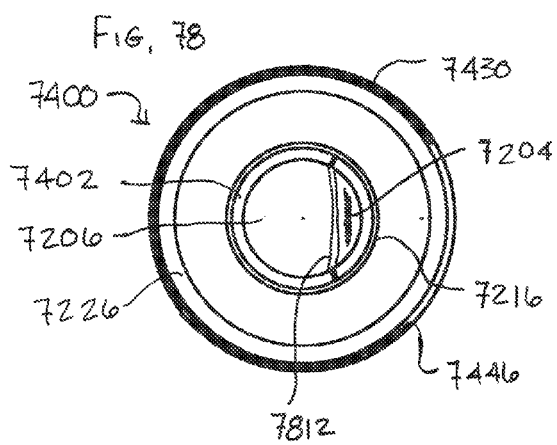
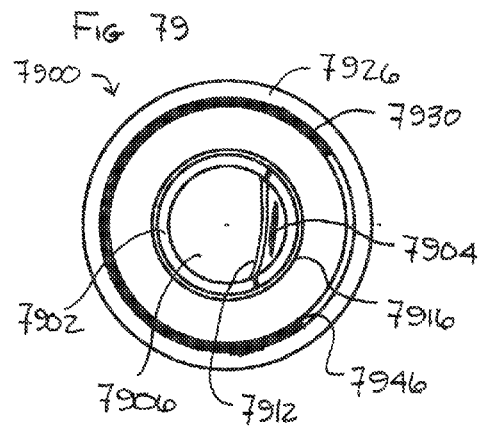
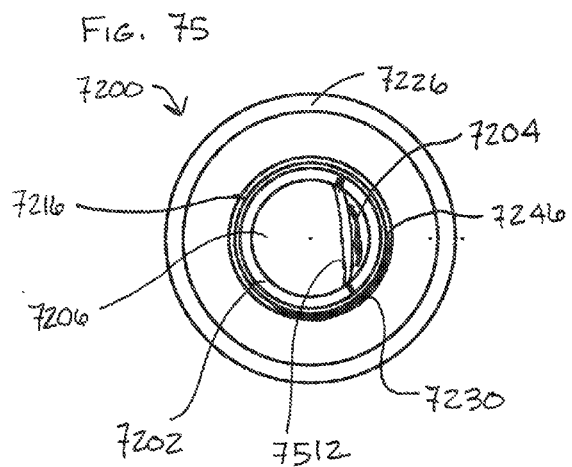
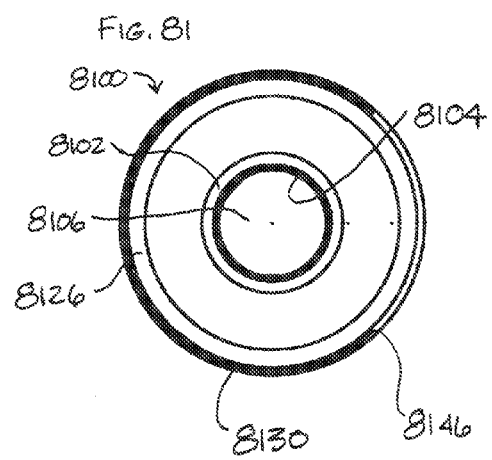
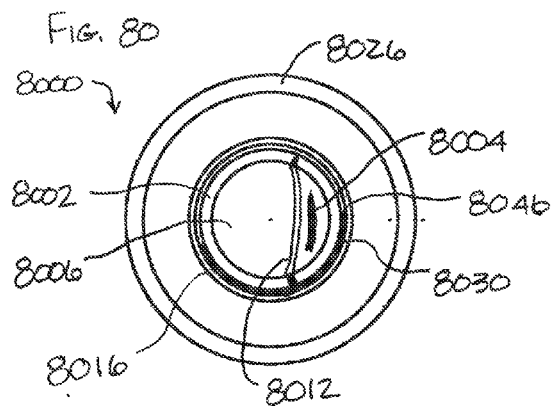

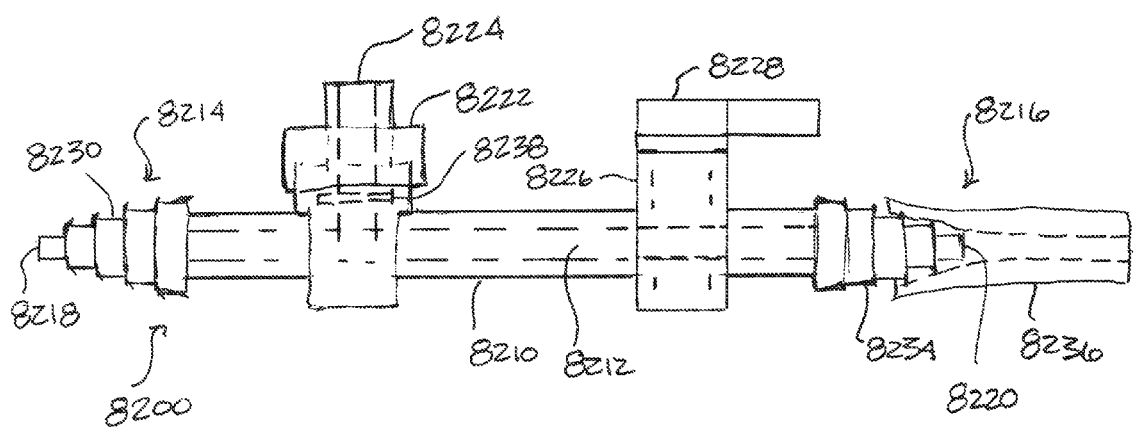

- 8510 — Attach the tee adaptor first end connector to the nasogastric tube and close the manual valve. Ensure the cap is on the accessory port.
- 8512 — Place the nasogastric tube in the patient at the desired insertion distance.
- 8514 — Before attaching the syringe to the fluid characteristic measurement apparatus, draw a predefined quantity of air into the syringe.
- 8516 — Attach the syringe to the fluid characteristic measurement apparatus.
- 8518 — After removing the cap, insert the fluid characteristic measurement apparatus and syringe into the accessory port.
- 8520 — Insufflate a predefined quantity of air from the syringe into the nasogastric tube.
- 8522 — Aspirate holding the indicator vertically until the indicator is saturated. During aspiration, all of the air that was in the NG tube will come into the syringe and there will be about 20-30cc of air at the top by the plunger.
- 8524 — Compare the detection indicator to the reference indicator and determine corresponding measurement.
- 8526 — Record or use the measurement.
- 8528 — Keeping the fluid characteristic measurement apparatus in the accessory port, attach the second end tubing connector to suction.
- 8530 — Turn on suction and open the manual valve.
- 8532 — Insufflate the contents in the syringe and fluid characteristic measurement apparatus into the tee-adaptor. Bodily fluids will be drawn into suction canister. Air in the top of syringe will flush all of the bodily fluids and gastric aspirate from the fluid characteristic measurement apparatus and syringe.
- 8534 — Remove the fluid characteristic measurement apparatus and syringe as one unit from the connector and discard.
- 8536 — Place the cap over the accessory port.
- 8538 — End

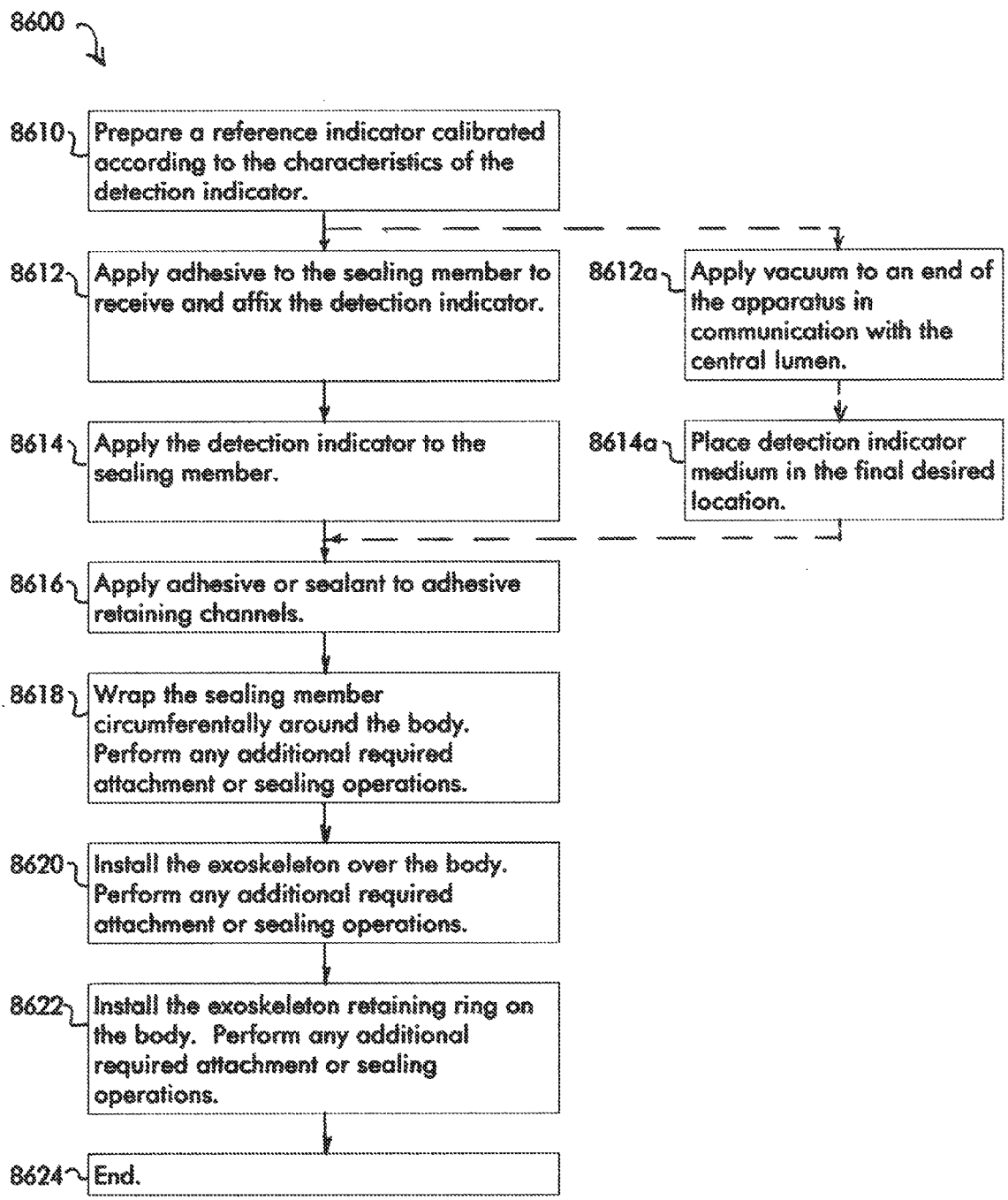

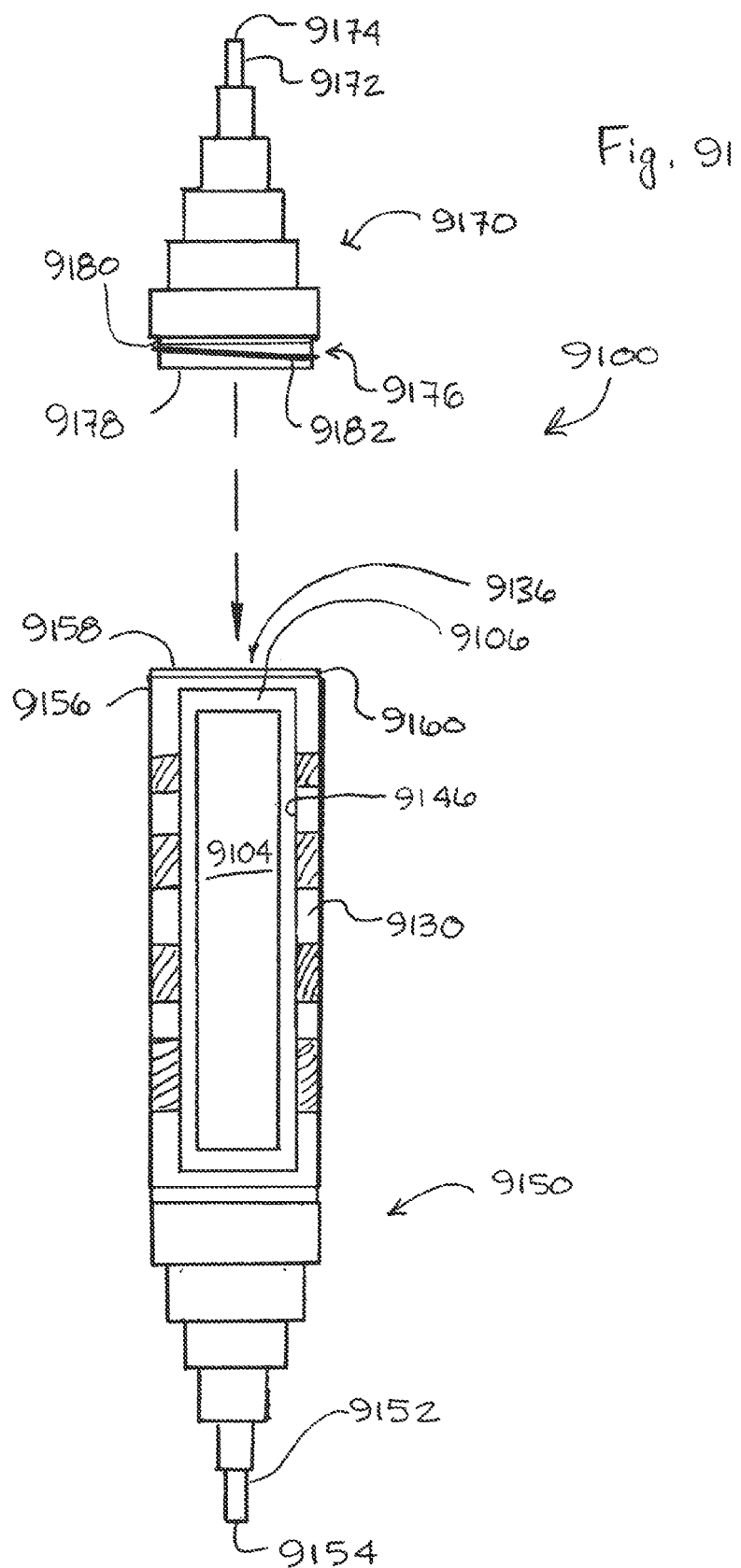

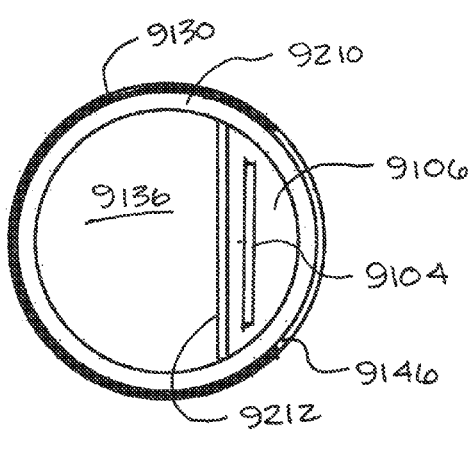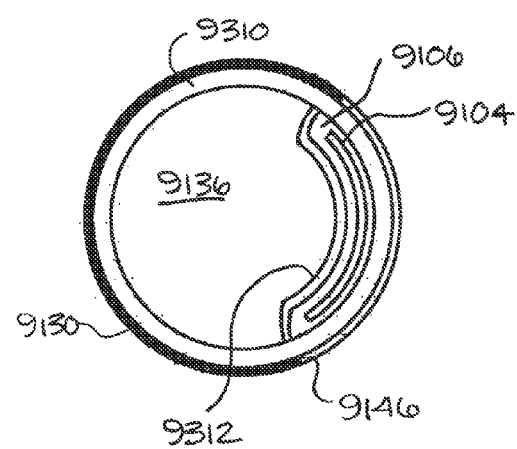

FLUID CHARACTERISTIC MEASUREMENT

CROSS REFERENCE TO RELATED APPLICATIONS

This application claims the benefit under 35 U.S.C. Sec. 119(e) of provisional application No. 61/524,878, filed Aug. 18, 2011, and is a Continuation-in-Part of application Ser. No. 12/925,783, filed Oct. 29, 2010, which is a Continuation-in-Part of application Ser. No. 12/799,123, filed Apr. 19, 2010, now abandoned which is a Continuation of application Ser. No. 11/769,597, filed Jun. 27, 2007, now U.S. Pat. No. 7,699,818 which is a Continuation-in-Part of application Ser. No. 11/548,086, filed Oct. 10, 2006, now U.S. Pat. No. 7,695,459 which is a Continuation-in-Part of application Ser. No. 11/347,481, filed Feb. 3, 2006, which claims the benefit under 35 U.S.C. Sec. 119(e) of provisional application No. 60/650,806, filed Feb. 8, 2005, the disclosures of which are incorporated by reference.

BACKGROUND

In medical practice, it is common to obtain a sample of a fluid for evaluation of various characteristics to aid in evaluation of a patient's health. Examples of such fluids include blood, urine, and stomach contents, which may be taken for analysis. Characteristics of the fluids that may be measured include pH and the presence or levels of various chemicals or medication. Fluids may be taken as a diagnostic aid and also to aid in placement of medical devices such as medical tubing for feeding, breathing, medication, and other uses.

There are many different clinical situations in which it is beneficial to know the gastric pH of a patient, or other chemical properties associated with the patient. Currently to determine the pH, a practitioner aspirates the stomach contents from a lumen (e.g., nasogastric tube, feeding tube, gastric tube) that is in communication with the stomach into a syringe. The contents are then expelled from the syringe and placed in a test tube and sent to a lab for a gastric pH analysis. It is also possible to place a pH probe down the lumen to attain a reading of the stomach contents. However these methods take a considerable amount of time and both can be costly. Another method is to aspirate the stomach contents into the syringe and then expel the contents of the syringe onto litmus paper or other pH indicating paper. This method is also timely and forces the practitioner to handle bodily fluids in the open. This can be both messy and inaccurate.

The pH is measured for multiple reasons. The most common reason being to monitor an intubated or critically ill patient's gastric pH. This is often measured because these critically ill patients develop gastric ulcers due to a lower gastric pH. These ulcers can bleed rapidly and are a cause for significant morbidity and mortality. These often require emergent endoscopy and cauterization to stop the bleeding.

Patients that are critically ill are often on medications that raise the gastric pH. However, dosages needed to adequately raise the pH of the stomach in critically ill patients may vary for each patient and are difficult to determine without measuring the gastric pH. This is often not done because it can be timely and costly to do so. Deviation in gastric pH from a relatively narrow preferred range has been associated with higher risk for certain types of pneumonia, ulcers, gastric bleeding, and other complications.

Detection of the desired characteristic is typically shown using a visual indicator, such as a colorimetric medium that changes from a first color to a second color upon sufficient contact with the fluid. For example, determining the pH for a sample of stomach contents can be performed with a litmus paper which turns red or blue upon contact with acids or bases, respectively. However, some media produce a range of colors responsive to a range of pH values, which both enables the acquisition of a pH reading, and creates challenges for medical personnel in correctly performing, interpreting, and recording the measurement. In addition, the fact that the response of the colorimetric medium can vary from manufacturer to manufacturer, manufacturing lot to manufacturing lot, and other conditions, makes the reliable acquisition of an accurate reading even more challenging.

Determination of the characteristics is often performed by a practitioner (e.g., nurse or doctor) who views the colorimetric medium for the change to occur. However, with many indicator mediums, the initial color change may happen quickly and include a range of colors. For example, a pH paper may be designed to change colors between a range of blue, green, and brown or between red, orange, and yellow to indicate specific levels of pH. The practitioner must then compare the colors of the pH paper with a known reference color to estimate the pH value. Reference colors are often provided on a separate chart for comparison with the visual indicator. Determination of the characteristics generally must be performed without delay, as the sample pH may change when the sample is exposed to air, and the response of the colorimetric medium may be stable and accurate for only a limited time after the medium is exposed to the sample.

A further challenge in a clinical setting is avoidance of personnel exposure to gastric aspirate and other bodily fluids.

SUMMARY

The invention in one implementation encompasses an apparatus. The apparatus comprises a detection indicator, a housing, and an exoskeleton into which the housing nests or telescopes. The detection indicator is configured to present a visual indication upon contact with a fluid, and responsive to a characteristic of the fluid. The housing comprises an interior chamber configured to receive the fluid and to provide contact between the fluid and the detection indicator. The relatively stiff exoskeleton protects the housing from stress that might promote fluid leakage, and is sealed to the housing so that it provides an additional barrier to leakage. The housing is configured to removably engage a conduit which is coupled to a source of a fluid sample. For example, the housing may engage a lumen inserted into a patient to receive the fluid from the patient through the lumen, but could also engage an multi-use adaptor arranged to both receive the fluid and dispose of the fluid after a sample is measured or read.

A further implementation of the invention encompasses an apparatus. The apparatus comprises a detection indicator, a first body portion, and a second body portion adapted to mate with the first body portion. The detection indicator is configured to present a visual indication upon contact with a fluid, and responsive to a characteristic of the fluid. The first body portion comprises an interior chamber or receptacle adapted to receive the detection indicator prior to mating with the second body portion. When mated, the first and second body portions are sealed to provide a leak-free lumen, channel, or conduit between opposite ends of the mated assembly and in fluid communication with the interior chamber. The housing is configured to removably engage a conduit which is coupled to a source of a fluid sample. For example, the housing may engage a lumen inserted into a patient to receive the fluid from the patient through the lumen, but could also engage an multi-use adaptor arranged to both receive the fluid and dispose of the fluid after a sample is measured or read. The interior chamber is configured to receive the fluid and to provide contact between the fluid and the detection indicator.

Another implementation of the invention encompasses a method of using the apparatus. The apparatus is connected to a conduit coupled to a sample source. Air is insufflated to ensure that an end of the conduit is not in contact with a stomach wall or the like. A transfer of a fluid sample from the source, into the removable housing is caused, for example, by a syringe, such that the fluid sample contacts a detection indicator coupled with the removable housing. A visual comparison of the detection indicator with a reference indicator, coupled to the removable housing, is performed to determine a characteristic of the fluid sample. When separating the removable housing from the conduit, the syringe remains with the housing to reduce the likelihood of spillage. Additional measures alone or in combination, including applying suction to the conduit, applying caps to a port of the conduit or to the nasogastric tube, operating valves to stop fluid communication through the apparatus, and insufflating all sample material so as to flush the sample from the apparatus, may be used to avoid or minimize leakage of the sample and prevent exposure of personnel thereto.

A further implementation of the invention encompasses a method of manufacturing the apparatus. During assembly, an adhesive may optionally be placed on the detection indicator, a wrappable sealing member, or a portion of the housing adapted to receive the detection indicator. Also optionally, a partial vacuum may be applied to a lumen of the housing in communication with the area in which the detection indicator is to reside. The vacuum, if present, helps secure the detection indicator in position during assembly. Adhesives or sealants are optionally applied to the sealing means or mating channels or surfaces of the housing. The sealing means is wrapped around the housing to capture the detection indicator. Any required final sealing operations are performed.

BRIEF DESCRIPTION OF THE DRAWINGS

Features of example implementations of the invention will become apparent from the description, the claims, and the accompanying drawings in which:

FIG. 2 is a side view of a guide element 120 of the nasogastric tube insertion system 100 of FIG. 1, showing the guide element in another configuration;

FIG. 3 is an enlarged side view of the leading section 154 of the guide element 120 of FIGS. 1-2;

FIG. 4 is a partial cross-section view of the leading section 154 of the guide element 120 of FIGS. 1-3 taken along section line 4-4 of FIG. 3;

FIG. 5 is a cross-section view of the trailing section 152 of the guide element 120 of FIG. 1 taken along section line 5-5 thereof;

FIG. 6 is a cross-section view of an alternate embodiment of the trailing section 152 of the guide element 120 of FIG. 1 taken along section line 5-5 thereof;

FIG. 7 is a cross-section view of another alternate embodiment of the trailing section 152 of the guide element 120 of FIG. 1 taken along section line 5-5 thereof;

FIG. 8 is a cross-section view of the leading section 154 of the guide element 120 of FIG. 1 taken along section line 8-8 thereof;

FIG. 9 is a cross-section view of an alternate embodiment of the leading section 154 of the guide element 120 of FIG. 1 taken along section line 8-8 thereof;

FIG. 10 is a cross-section view of a nasogastric tube 110 of the nasogastric tube insertion system 100 of FIG. 1, taken along section line 10-10 thereof;

FIG. 11 is a side view of an inserter element 130 of the nasogastric tube insertion system 100 of FIG. 1;

FIG. 12 is an enlarged side view of the insertion section 174 of inserter element 130 of FIGS. 1 and 11 and the leading section 154 of guide element 120 of FIGS. 1-4 showing the insertion section 174 about to be attached to the guide element 120;

FIG. 13 is an enlarged perspective view of the tip 186 of insertion section 174 of inserter element 130 of FIGS. 1, 11, and 12 and a portion of the leading section 154 of guide element 120 of FIGS. 1-4;

FIG. 14 is a side view showing the guide element 120 of FIGS. 1-4 attached to the inserter element 130 of FIGS. 1, 11, and 12, and depicting a stage in an exemplary method of inserting the nasogastric tube insertion system 100 in which the swallowable weight 158 is held on the tip 186 of inserter element 130 by tension on the guide element 120 provided by the user;

FIG. 21 is an enlarged side view of an alternative embodiment 270 of the insertion section of inserter element 130 of FIGS. 1 and 11 and an alternative leading section 250 of guide element 120 of FIGS. 1-2, showing the alternative insertion section 270 about to be attached to the guide element 120;

FIG. 22 is an enlarged cross-section view of an alternative embodiment 250 of the leading section of the guide element 120 of FIG. 21, taken along the section line 22-22 thereof;

FIG. 23 is an enlarged perspective view of the tip 272 of alternative insertion section 270 of inserter element 130 of FIGS. 1 and 21 and a portion of the alternative leading section 250 of guide element 120 of FIG. 22;

FIG. 33 is a side view showing the leading section of an alternate embodiment of a guide element with a weight element thereof having a first example configuration;

FIG. 34 is a side view showing the leading section of an alternate embodiment of a guide element with a weight element thereof having a second example configuration;

FIG. 35 is a side view showing the leading section of an alternate embodiment of a guide element with a weight element thereof having a third example configuration;

FIG. 36 is a side view showing the leading section of an alternate embodiment of a guide element with a weight element thereof having a fourth example configuration;

FIG. 37 is a side view showing the leading section of an alternate embodiment of a guide element before the weight element thereof is installed, depicting a first example configuration of members for retaining the weight element;

FIG. 38 is a side view showing the leading section of an alternate embodiment of a guide element before the weight element thereof is installed, depicting a second example configuration of members for retaining the weight element;

FIG. 43 is a side view of the proximal end section of an alternate embodiment of a nasogastric tube showing a chemical-property indicating element thereof;

FIG. 44 is a cross section view of the alternate embodiment of the nasogastric tube of FIG. 43, taken along the section lines 44-44 of FIG. 43;

FIG. 45 is a side view of the proximal end section of a further alternate embodiment of a nasogastric tube showing a chemical-property indicating medium thereof in a first example configuration;

FIG. 46 is a side view of the proximal end section of a further alternate embodiment of a nasogastric tube showing a chemical-property indicating medium thereof in a second example configuration;

FIG. 47 is a cross section view of the alternate embodiment of the nasogastric tube of FIG. 45, taken along the section lines 47-47 of FIG. 45;

FIG. 48 is a cross section view of the alternate embodiment of the nasogastric tube of FIG. 46, taken along the section lines 47-47 of FIG. 45;

FIGS. 56A and 56B are top and side views of the housing of FIG. 55 with the detection indicator in place.

FIG. 60 is a side view of another implementation of the housing and the fluid retrieval component formed as a bulb-syringe.

FIG. 61 is a side view of another implementation of the housing and the fluid retrieval component formed as a syringe.

FIG. 62 is a side view of an implementation of the housing formed as a test tube.

FIG. 63 is a side view of another implementation of the housing formed as a vacutainer.

FIG. 64 is a partial side view of one implementation of the housing illustrating the detection indicator molded into a wall of the housing.

FIG. 65 is a cross section of another implementation of the housing illustrating a separate channel for the detection indicator.

FIG. 72 is a side elevation view of a further implementation of a fluid characteristic measurement apparatus constructed according to an aspect of the invention.

FIG. 75 is a simplified cross-section view of the fluid characteristic measurement apparatus of FIGS. 72-73, taken across the major longitudinal axis thereof, showing the relative placement certain components.

FIG. 78 is a simplified cross-section view of the fluid characteristic measurement apparatus of FIG. 74, taken across the major longitudinal axis thereof, showing the relative placement of certain components.

FIG. 79 is a simplified cross-section view of a further implementation of a fluid characteristic measurement apparatus, taken across the major longitudinal axis thereof, showing the relative placement of certain components.

FIG. 80 is a simplified cross-section view of a further implementation of a fluid characteristic measurement apparatus, taken across the major longitudinal axis thereof, showing the relative placement of certain components.

FIG. 81 is a simplified cross-section view of a further implementation of a fluid characteristic measurement apparatus, taken across the major longitudinal axis thereof, showing the relative placement of certain components.

FIG. 82 is a side elevation view of a tee adaptor which may be used in conjunction with any of the fluid characteristic measurement apparatus disclosed herein.

FIG. 85 is a flow diagram showing a method which may be used in conjunction with the apparatus of FIG. 83, to measure a characteristic of a fluid, such as that which may be obtained through a nasogastric tube which has been inserted into a medical patient.

FIG. 86 is a flow diagram depicting a partial method for manufacturing a fluid characteristic measurement apparatus of the type disclosed herein.

FIG. 87 is a side elevation view of a further implementation of a fluid characteristic measurement apparatus constructed according to an aspect of the invention.

FIG. 89 is a side elevation view of a portion of an implementation of an adaptor which may be used with the fluid characteristic measurement apparatus disclosed herein.

FIG. 91 is a side elevation view of a further implementation of a fluid characteristic measurement apparatus.

FIG. 92 is a simplified cross-section view of a further implementation of a fluid characteristic measurement apparatus, taken across the major longitudinal axis thereof, showing the relative placement of certain components.

FIG. 93 is a simplified cross-section view of a further implementation of a fluid characteristic measurement apparatus, taken across the major longitudinal axis thereof, showing the relative placement of certain components.

DETAILED DESCRIPTION

One embodiment of a nasogastric tube insertion system 100 constructed according to the present invention is shown generally in FIGS. 1-20. The nasogastric tube insertion system 100 is intended for use with a patient who is conscious, alert, and able to swallow.

Figure 1:
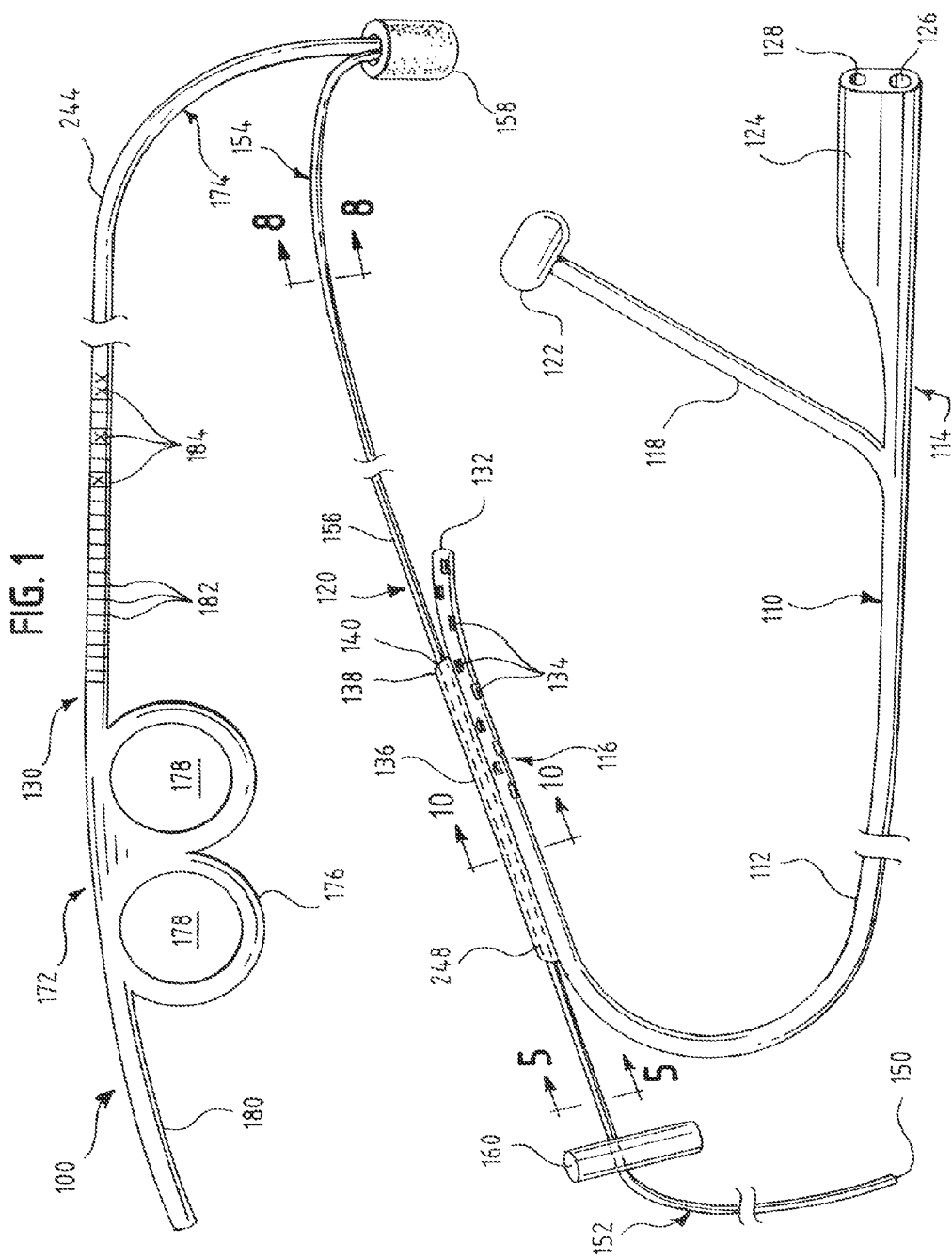
FIG. 1 is an overall side view of an exemplary embodiment of a nasogastric tube insertion system 100 constructed according to an aspect of the present invention.

As best seen in FIG. 1, the nasogastric tube insertion system 100 comprises a nasogastric tube 110, a guide element 120, and an inserter element 130. The function of the inserter element 130 is to aid in the initial placement of a portion of the guide element 120 in the patient's oropharynx.

The function of the guide element 120 is to establish a desired path for passage of nasogastric tube 110 through the patient's nasal passages, the oropharynx, the esophagus, and the stomach, and to guide the nasogastric tube 110 along that path during the tube's insertion.

FIGS. 24-28, discussed further in greater detail, depict alternate embodiments of a nasogastric tube which may be used in conjunction with the guide element 120 and inserter elements of the present invention. One of skill in the art will appreciate that although several embodiments of nasogastric tubes are described herein as examples by which aspects of the present invention may be implemented, the inserter element, guide element, and associated methods could be used for other types of nasogastric tubes and for other similarly configured objects which are desired to be inserted through the patients nostrils.

FIG. 1 depicts a configuration in which the nasogastric tube 110, guide element 120, and inserter element 130 are simultaneously connected to or engaged with one another, and a commercial embodiment of the nasogastric tube insertion system 100 could be so constructed. However, it will be appreciated that is not necessary that these components ever actually be arranged in that configuration. It is sufficient that the guide element 120 be attached to the inserter element 130 during the insertion of a portion of the guide element into the patient's oropharynx. In a subsequent step, it is sufficient that the guide element 120 be partially enveloped by or threaded through a portion of the nasogastric tube 110 during the insertion of the tube 110 in order that the tube 110 follow the path established by the guide element 120.

As best seen in FIGS. 1 and 11, the inserter element 130 is constructed as a generally thin, longitudinal member having predominantly straight, slender, and elongate main body section 172 and a curved insertion section 174 which is adapted to engage an end of guide element 120 to enable insertion of the guide element into the patient's nasal passage or oropharynx. The insertion section 174 shown and described in connection with these figures is a first exemplary embodiment constructed according to an aspect of the present invention. An alternative embodiment 270 of the insertion section, adapted for use with an alternative embodiment 250 of the leading section of guide element 120, is shown in FIGS. 21-22 and described further in greater detail.

The inserter element 130 preferably comprises a handle 176 to allow the inserter element 130 to be readily grasped and controlled by a user. An exemplary configuration for handle 176 is shown in FIGS. 1 and 11, in which the handle is formed as two loops of structural material attached to and extending downward from the main body 172. The loops form handle openings 178, which may, for example, receive the user's index and middle fingers and allow the inserter element 130 to be grasped. A stabilizing extension 180 extending from the main body section rearward of the handle 176 improves stability during handling of the inserter element 130. Other handle configurations could also be used.

The main body 172 of the inserter element 130 may be constructed of any suitable material having sufficient thickness and strength to be handled and to support the modest weight of the insertion section 174 and a portion of the guide element 120 which is attached thereto during the insertion process. For example, the insertion section 174 may be constructed of semi-flexible, biologically inert material, such as clear poly-vinyl chloride. Other materials could also be used. The cross section and exact dimensions of the main body 172 are non-critical but may be selected to optimize cost, user comfort, and compatibility with the insertion section 174.

The insertion section 174 preferably has one or more curved portions such that it generally conforms to the anatomy of a typical patient's nasal passages and oropharynx. The curved portions may cumulatively provide curvature in the range of approximately 70 to 100 degrees of arc in the direction of the handle 176.

The insertion section 174 is preferably constructed of a flexible, biocompatible material, providing sufficient stiffness to support the swallowable weight 158 of guide element 120, but also providing enough flexibility to deform as needed, during insertion of the insertion section 174 into the patient's nasal passages, to pass any obstacles encountered without injury or abrasion. For example, the insertion section 174 may be constructed of semi-flexible, biologically inert material, such as clear poly-vinyl chloride. Other materials could also be used. The insertion section 174 may have any suitable cross section, including without limitation a generally circular, semi-circular, oval, oblong, or rectangular cross section. The cross-section of insertion section 174 may permit more flexibility in the direction of curvature than in directions perpendicular thereto. As discussed further in greater detail, the insertion section 174 preferably has a groove or channel 194 (FIG. 13) along at least a portion of its dorsal surface to receive a portion of the guide element 120. The insertion section 174 is preferably free of sharp exterior edges or other structures that may cause injury or abrasion of tissues in the nasal passages.

The exact dimensions of the insertion section 174 are non-critical, but preferably are selected as appropriate for the material used, to provide a desired amount of stiffness and flexibility, and to allow the inserter to easily enter and pass through the nasal passages of a patient. The insertion section 174 should be long enough that, when inserted, the tip 186 can reach into the patient's oropharynx without requiring the handle 176 to impinge on the patient's face. It is believed that an insertion section 174 having a width less than or equal to about 0.75 cm, a thickness less than or equal to about 0.5 cm, and a length of approximately 25 cm or more, would be appropriate for use with an adult patient of typical size. Smaller dimensions may be needed for use with smaller patients, including children and infants. In addition, the dimensions could be varied to achieve desired variations in stiffness or other mechanical parameters. For example, if increased flexibility is desired toward the end of the insertion section 174, the thickness or width may be gradually reduced in that section. The main body 172 and insertion section 174 may be separately constructed and later assembled to form a unit. Alternately, the main body 172 and insertion section 174 may be constructed as a single unit, and there may be no visible structural characteristics that signal when one ends and the other begins.

The inserter element 130 preferably has measurement lines 182 or other suitable indicia to allow the user to readily ascertain when the inserter has been inserted to a predetermined insertion depth, corresponding to the placement of the end of the insertion section 174, and the swallowable weight 158 attached thereto, in a desirable location in the patient's oropharynx.

For most patients, an optimal predetermined insertion depth may be found by measuring the distance between the patient's earlobe and the tip of the patient's nose. The inserter element 130 may also have measurement legend indicia 184 specifying units of measurement or other related information associated with measurement lines 182. However, the user may perform the distance measurement using the inserter element 130 itself, e.g., by marking the distance on the measurement lines 182.

Although it is normally expected that the desired inserter-assisted placement of the swallowable weight 158 be into the patient's oropharynx, it may be preferable in some situations to use the inserter element 130 to place the swallowable weight 158 only part way into the nasal passages. In those situations, the swallowable weight 158 would then be released from the inserter element 130, and the user would advance the guide element 120 into the oropharynx by applying longitudinal pressure, relying on the stiffness of the guide element to assist placement. A shorter inserter element 130 could be used for such situations, and the desired insertion distance could be measured using different benchmarks on the patient's face or body.

As best seen in FIG. 13, the insertion section 174 preferably has walls 196 forming a groove or channel 194 along at least a portion of its dorsal surface 244 to receive the guide element 120. An alternative embodiment 270 of the insertion section is shown in FIGS. 21-23 and described further in greater detail. Once the swallowable weight 158 of the guide element 120 is placed on the end of the inserter element 130, in order to retain the swallowable weight 158 in position, the user must apply light tension on the guide element 120. The channel 194 is adapted to retain the guide element 120 along the top surface of the inserter element 130 while tension is applied. This avoids undesirably deforming the insertion section 174 and prevents the guide element 120 from taking on a "bow string" configuration, which would interfere with the insertion process.

Although channel 194 is depicted in FIG. 13 as a generally U-shaped channel of considerable depth, other configurations could also be used provided they retain the guide element 120 along the dorsal surface 244 of the inserter element 130 while light tension is applied to the guide element 120. For example, the depth of the channel could be significantly less than depicted. For another example, the channel-forming walls 196 could be formed as two or more longitudinal ridges on the dorsal surface of the guide element 120, which might otherwise be flat. The ridges could be of any height that satisfactorily retains the guide element 120 while light tension is applied. The term "dorsal" is used here to refer to the upper surface 244 of the inserter element 130, as shown in FIGS. 1 and 11, without respect to the orientation in which the inserter element 130 is held.

As best seen in FIGS. 11-13, the tip 186 of the insertion section 174 has a stepped engagement section 188 of reduced thickness for loosely engaging the swallowable weight 158 of the guide element 120. As mentioned above, once the swallowable weight 158 is placed onto the tip 186 of the insertion section 174, the tip is preferably held in place by light tension on guide element 120. The loose engagement preferably allows the swallowable weight 158 to be released from the tip 186 by releasing tension on the guide element 120, allowing the swallowable weight 158 to fall away. FIGS. 12 and 13 depict the tip 186 and stepped engagement section 188 in alternate configurations. FIGS. 21 and 23 depict an alternative embodiment 270 of the insertion section and will be discussed further in greater detail.

In FIG. 12, there is shown a first embodiment in which the tip 186 has an angular chamfered section 190 adapted to engage a mating receptacle 168 of the swallowable weight 158 of the guide element 120. Substantially vertical step walls mark the boundary between the full-thickness portion of the insertion section 174 and the stepped engagement section 188. The stepped engagement section 188 extends a short distance from the step walls 198 to the tip 186. The leading section 154 of guide element 120 is retained in channel 194 (FIG. 13) when the swallowable weight 158 is placed on tip 186 and light tension is applied to guide element 120.

In FIG. 13, there is shown a second embodiment in which the tip 186 has a substantially vertical wall section 192 instead of the angular chamfered section 190 of FIG. 12. Angular step walls 242 mark the boundary between the full-thickness portion of the insertion section 174 and the stepped engagement section 188. The stepped engagement section 188 extends a short distance from the step walls 242 to the tip 186. The leading section 154 (FIG. 12) of guide element 120 is retained in channel 194 when light tension is applied to guide element 120.

As best seen in FIGS. 1-2, the guide element 120 is constructed as a thin, elongate or generally longitudinal element, which may be a cord or line, having a leading section 154 having sufficient flexibility to be easily inserted into and swallowed by the patient, and trailing section 152 having sufficient rigidity to guide the nasogastric tube 110 as the tube is inserted. The trailing section also functions as a tether. A swallowable weight 158 is attached to the leading section 154. A transition 156 joins the trailing section 152 and leading section 154. A stopper 160 may be provided near the end 150 of guide element 120 opposite the swallowable weight 158 to prevent the end from being swallowed by the patient. Alternatively, the trailing section 152 could be extremely long, such that it cannot be swallowed. An alternative embodiment 250 of the leading section of guide element 120 is shown in FIGS. 21-22 and described further in greater detail.

The trailing section 152 of the guide element 120 may be constructed of any suitable material having sufficient thickness, flexibility and strength to be handled and to reliably avoid breakage. The trailing section 152 is preferably be rigid enough to navigate over the trachea and into the esophagus, but flexible enough to be readily swallowed. For example, the trailing section 152 may be constructed of a silicone elastomer or of a polymer in the nylon family. Other highly-flexible, biologically inert materials could also be used.

The leading section 154 is preferably constructed of any suitable biocompatible material, having sufficient thickness, flexibility and strength to be handled and to reliably avoid breakage. The leading section 154 is preferably flexible enough to be very easily swallowed. Because the leading section 154 will be swallowed and will be subject to digestive acids and enzymes for some period, the material from which the leading section 154 is constructed is preferably highly resistant to attack from such agents. For example, the leading section 154 may be constructed of a silicone elastomer or of a polymer in the nylon family. Other highly-flexible, biologically inert materials could also be used. Preferably, the trailing section 152 is free of sharp edges and has suitable outer surface features and finish to avoid injury or abrasion of tissues when the leading section 154 is swallowed and removed. In some situations, it may be desirable to use the inserter element 130 to assist the insertion of the leading section 154 of guide element 120 only part way into the patient's nasal passages, and then to use longitudinal pressure on the guide element 120 to further advance the leading section 154 into the patient's oropharynx without the continued assistance of the inserter element 130.

In such situations, it is desirable that leading section 154 possess sufficient stiffness accommodate advancement of the leading section into the oropharynx, while retaining sufficient flexibility to avoid damaging tissues during insertion and removal.

As best seen in FIGS. 5-7 and 8-9, the longitudinal elements 152, 154 of the guide element 120 may be constructed as a unitary or monofilament line or piece, or as a string or cord, or similar form of stranded or woven multifilament line. FIGS. 5 and 8 depict in cross section a first exemplary embodiment of the guide element 120 in which the trailing section 152a is formed as an element of generally oval or oblong cross section, and the leading section 154a is also formed as an element of generally oval or oblong cross section of somewhat reduced size.

FIGS. 6 and 9 depict in cross section a second exemplary embodiment of the guide element 120 in which the trailing section 152b is formed as an element of generally circular cross section, and the leading section 154b is also formed as an element of generally circular cross section of somewhat reduced size. FIG. 7 depicts in cross section a third exemplary embodiment of the guide element 120 in which both the trailing and leading section 152c are formed as a twisted bifilar cord.

The elements may be formed by molding, extrusion, drawing, or any other suitable method of manufacture. These particular configurations are provided by way of example, not limitation, and it will be appreciated that other cross sections, number of filaments, stranding configurations, and the like could also be used, and that the configuration used for the leading section 154 may differ from that used for the trailing section 152.

The exact dimensions of the leading section 154 and the trailing section 152 of guide element 120 are non-critical but may be selected to optimize cost, compatibility with one another, and with a guide element retaining structure 136 of nasogastric tube 110 (FIGS. 1, 10), discussed further in greater detail. A leading section 154 having a width in the range of approximately 0.1-2.5 mm and a thickness in the range of approximately 0.1-2.5 mm, would be appropriate, but the necessary dimensions may vary depending on material choices, the flexibility or stiffness desired, and other factors. A trailing section 152 having a width in the range of approximately 0.1-3.5 mm, and a thickness in the range of approximately 0.1-3.5 mm would be appropriate, but the necessary dimensions may vary depending on material choices, the flexibility or stiffness desired, and other factors. The trailing section 152 and leading section 154 may be separately constructed and later assembled to form a unit. Alternately, the trailing section 152 and leading section 154 may be constructed as a single unit.

A transition area 156 designates the area at which trailing section 152 is joined to leading section 154. If these components are formed as an integrated unit of the same size and cross-section throughout, the transition area may not be apparent. If the trailing section 152 and leading section 154 are dissimilar, the leading section 154 is preferably long enough to allow the patient to swallow the swallowable weight 158 into the stomach without ingesting part of the trailing section 152. Also, the change from leading section 154 to the trailing section 152 may be gradual rather than abrupt.

As best seen in FIGS. 3, 4, and 12, the swallowable weight 158 is attached to the leading section 154 of guide element 120. The swallowable weight 158 preferably comprises a resilient body 246 and an interior attachment structure 164 for affixing the shell to the leading section 154 of the guide element 120. An alternative embodiment 252 of the swallowable weight is shown in FIGS. 21 and 22, and described further in greater detail.

The body 246 is preferably soft and resilient so that it may be easily swallowed with minimal discomfort to the patient and so that it avoids abrading or irritating tissues when it is inserted through the patient's nasal passages into the oropharynx. The body 246 is preferably constructed from a flexible, absorbent, biocompatible material, which may, for example, be a spongiform material such as open-cell foam. Other materials could also be used. Because the body 246 will be swallowed and will be subject to digestive acids and enzymes for some period, the material from which the body 246 is constructed is preferably highly resistant to attack from such agents. Although the swallowable weight 158 is referred to as a weight, it need not be heavy or constructed of dense materials. It is sufficient that the weight be easily swallowed. The dimensions of the swallowable weight 158 are not critical, but the weight is preferably of a size that can be easily swallowed and can easily pass through the patient's nasal passages. A diameter in the range of approximately 0.4-1.25 cm, and a length in the range of approximately 0.7-1.7 cm are believed to be suitable for most adult patients. Other sizes could also be used; a smaller weight may be required for smaller patients, such as children and infants.

The interior attachment structure 164 may be any suitable structure that can be securely affixed to the body 246. For example, the attachment structure 164 may be formed as a cup-like element having a cylindrical attachment wall 166. However, other structures could also be used. The attachment structure 164 may be secured to the body 246 using any suitable fastening technology, including but not limited to glue, ultrasonic or chemical bonding or welding, structural features such as barbs or hooks, or a tight friction fit.

The leading section 154 of guide element 120 extends outward from the attachment structure 164 through an opening 162 in the body 246. The leading section 154 may be secured to the attachment structure 164 using any suitable fastening technology, including but not limited to glue, ultrasonic or chemical bonding or welding, or interlocking structural features.

Alternatively, the attachment structure 164 may be formed as an integrated part of the leading section 154. As best seen in FIG. 3, the bottom 168 of the attachment structure 164, the attachment wall 166, and the leading section 154 form an evacuated-toroid-shaped space to receive the tip 186 of the insertion section 174 of the inserter element 130. This configuration enables the tip 186 to be held against the attachment structure 164 without piercing the resilient material of the body 246, which would undesirably produce a frictional engagement of these components. A loose engagement between swallowable weight 158 and tip 186 of leading section 154 of inserter element 130 is desirable to allow the swallowable weight 158 to be released from the tip 186 by releasing tension on the guide element 120, causing the swallowable weight 158 to fall away.

As best seen in FIGS. 1 and 8, the nasogastric tube 110 is preferably constructed as an elongate, generally tubular, body structure comprising a main tubular section 112, a proximal end section 114, and a distal end section 116. The distal end section 116 is intended to be inserted into the patient. The proximal end section 114 is intended to remain outside of the patient. The nasogastric tube 110 includes one or more interior bores or lumina extending approximately the length of the tube 110. As best seen in FIG. 10, an exemplary embodiment of nasogastric tube 110 has three interior bores or lumina 144, 146, and 148, but more or fewer lumina could be used depending on the application and the permissible thickness of the nasogastric tube 110. For example, nasogastric tube 110 may have a single lumen for use as a feeding tube to allow the direct introduction of food or nutritional supplements into the patient's stomach. Nasogastric tube 110 may also comprise a radiopaque tracer strip 142 to allow the position of the nasogastric tube 110 to be verified using radiographic or fluoroscopic examination.

The proximal end section 114 may separate into two or more breakout segments, each including one or more of the lumina 144, 146, 148. As best seen in FIG. 1, in an exemplary embodiment, proximal end section 114 separates into a first breakout tube 118, carrying lumen 144, and a second breakout tube 124 carrying lumina 146 and 148. Second breakout tube 124 provides openings 126 and 128 into lumina 146 and 148 to allow connection of the lumina to a source of fluid to be introduced into the stomach, or a vacuum "supply to remove fluid from the stomach, or to allow the lumen to be vented to the atmosphere. First breakout tube 118 has an opening (not shown) into first lumen 144. As best seen in FIG. 1, a one-way valve 122 may be connected to one of the lumina to control ventilation of the stomach.

The distal end section 116 has a leading end 132. Adjacent the leading end 132, there is provided a plurality of openings 134 leading to the interior bores or lumina 144, 146, and 148 and allowing fluid and gas communication between the lumina 144, 146, and 148 and the exterior space surrounding the leading end 132. The opening or openings leading to a particular one of the lumina may be spaced from the openings leading to other lumina as required by the application. For example, if one lumen is assigned to introduce fluids into the stomach, and another lumen is assigned to remove fluids from the stomach, it may be desirable to separate the corresponding openings so that the fluids newly introduced are not immediately removed.

The distal end section 116 of nasogastric tube 110 further comprises a guide element retaining structure 136 adapted to move slidably along guide element 120. As best seen in FIGS. 1 and 10, the guide element retaining structure preferably comprises a generally tubular protrusion or intrusion attached and parallel to proximal end section 114 having a tubular opening 140 to receive the guide element 120. Once the guide element has been inserted, the guide element retaining structure 136 allows the nasogastric tube 110 to move slidably and telescopically along the guide element 120. Thus, the guide element 120 may serve to establish a path for the nasogastric tube 110 to follow as it is inserted through the patient's nasal passages, oropharynx, esophagus, and into the patient's stomach. The leading end 138 and a trailing end 248 of the guide element retaining structure 136 are preferably chamfered to avoid abrading or irritating tissues which are encountered as the nasogastric tube 110 is inserted and removed.

Although the guide element retaining structure 136 is shown in FIGS. 1 and 10, and described herein as a tubular element attached to the distal end section 116, other structures could also be used to form the guide element retaining structure 136 adapted for slidable and/or telescopic movement along the guide element 120. For example, the guide element retaining structure 136 could be formed as one or more loops or retaining tabs attached to the distal end section 116. For another example, the guide element retaining structure 136 could be formed as a tunnel-style bore through an unused portion of the cross section of the nasogastric tube 110. This configuration has the advantage that no enlargement of the cross-sectional size of the nasogastric tube 110 is needed, but it may not be possible to implement if the tube is crowded. As a further alternative to a separate structure 136 dedicated to retaining the guide element 120, features of the distal end 116 of the nasogastric tube 110 may be used to form a guide element retaining structure. For example, guide element 120 could be threaded or telescoped through an aperture placed at or adjacent the tip 132 of the distal end section 116 of the nasogastric tube 110, extend through one of lumina 144, 146, or 148, and could exit through one of the openings or apertures 134 in communication with such lumen and spaced from the tip 132.

The dimensions of the nasogastric tube 110 are non-critical, but must be selected to allow the tube to be inserted through the nasal passages and into the stomach, and to remain there without interfering with the patient's respiration. A smaller diameter, if permitted by the requirements for the lumina inside the tube, is generally preferable in that it minimizes patient discomfort. A nasogastric tube 110 having a diameter of approximately 0.25 inches is believed to be suitable for most adult patients. The length of the nasogastric tube 110 should be long enough to extend into the patient's stomach, with some additional length outside the patient to allow for convenient external connections and to prevent the patient from inadvertently swallowing the proximal end section 114 of the nasogastric tube 110.

The nasogastric tube 110 is preferably constructed of any suitable biocompatible material, having sufficient thickness, flexibility and strength. Because the nasogastric tube 110 will be swallowed and will be subject to digestive acids and enzymes for some period, the material from which the nasogastric tube 110 is constructed is preferably non-porous and highly resistant to attack from such agents. For example, the nasogastric tube 110 may be constructed of a silicone elastomer. Other flexible, biologically inert materials could also be used. The nasogastric tube 110 is preferably transparent or translucent to allow visual inspection of the lumina for proper operation.

FIGS. 14-19 depict several steps in exemplary methods 310, 310a (FIG. 20) according to an aspect of the present invention for use in conjunction with the nasogastric tube insertion system 100 of FIGS. 1-13.

Figure 20:
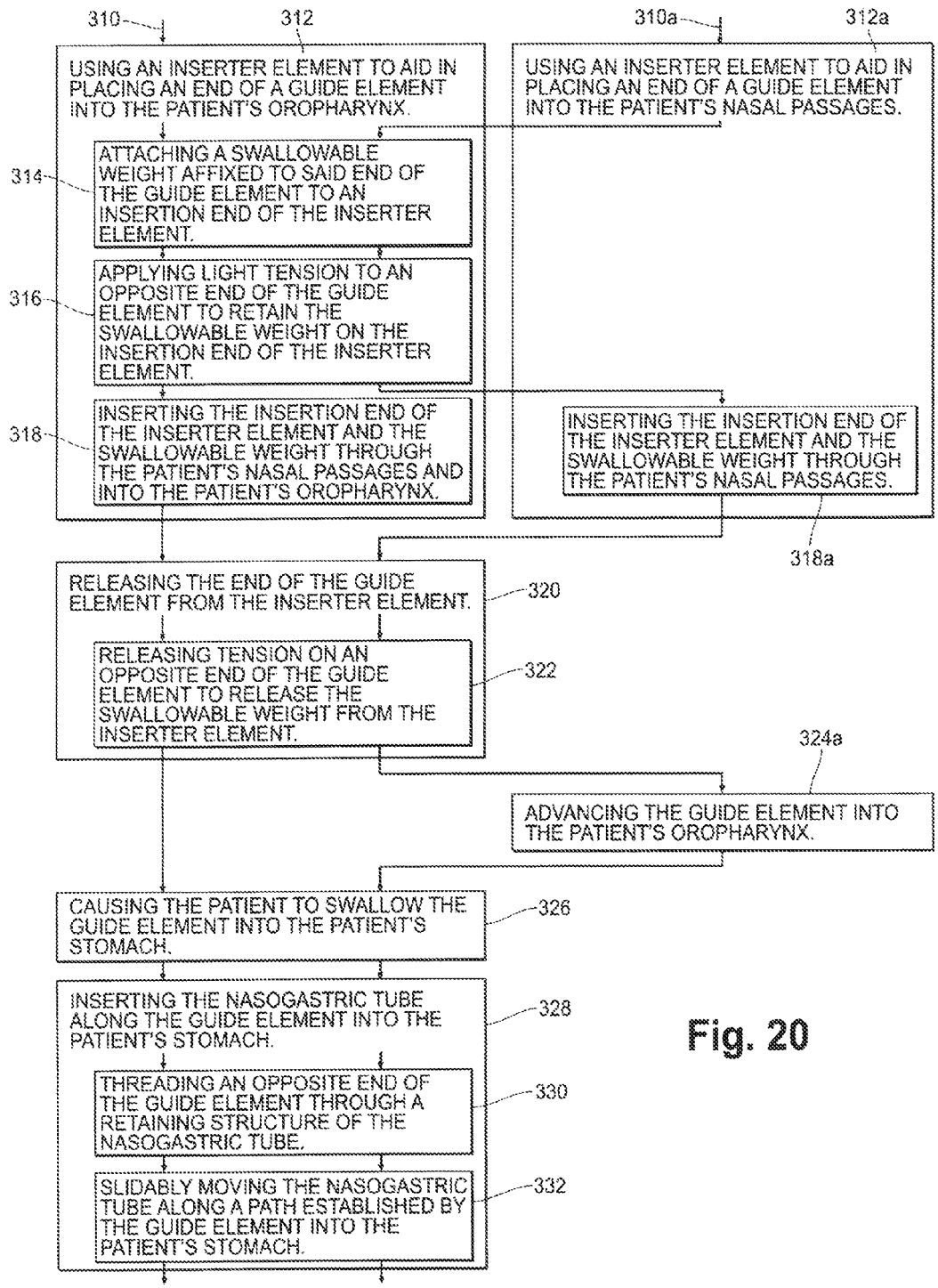
FIG. 20 is a flow diagram depicting steps of exemplary methods 310, 310a of inserting the nasogastric tube insertion system 100 into the patient.

FIG. 20 is a flow diagram depicting steps of exemplary methods 310, 310a. In method 310, the inserter element 130, with the swallowable weight 158 engaged to the insertion end thereof, is used to insert the swallowable weight through the patient's nasal passages and into the oropharynx.

In method 310a, the inserter element 130 is used to insert the swallowable weight through the patient's nasal passages. Then the swallowable weight 158 is released from the end of inserter element 130 and is advanced into the patent's oropharynx, by, for example, gentle longitudinal pressure on the guide element 120 in the direction of the patient's oropharynx.

In other respects, the methods 310 and 310a are similar. The term "step" is used herein to refer to both the general steps associated with one of methods 310, 310a, and to more detailed substeps which may be comprised as part of a more general step. Some steps are optional.

Figure 15:
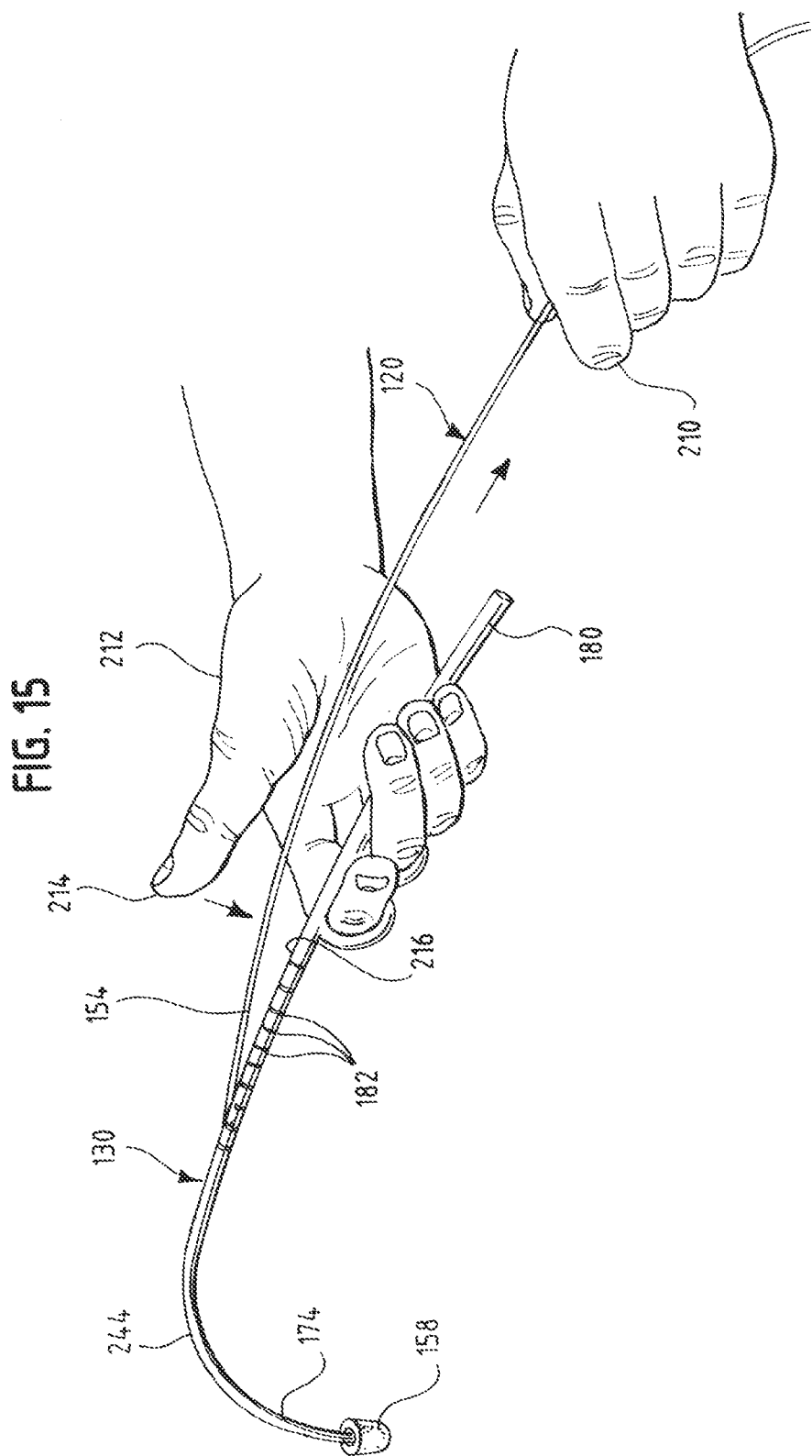
FIG. 15 is a side view showing the guide element 120 of FIGS. 1-4 attached to the inserter element 130 of FIGS. 1, 11, and 12, and depicting another stage in the method of inserting the nasogastric tube insertion system 100 in which the swallowable weight 158 is held on the tip 186 of inserter element 130 by tension on the guide element 120 provided by the user.

A first group of steps 312, 314, 316 is generally depicted in FIG. 14. The user grasps the handle 176 (FIGS. 1 and 11) of inserter element 130 using a first hand 212. The user places the swallowable weight 158 on the tip 186 of insertion section 174 of inserter element 130 (step 314). The user then uses a second hand 210 to apply light tension on guide element 120, thereby maintaining the swallowable weight 158 in position on the end of inserter element 130 (step 316) A second group of steps is generally depicted in FIG. 15. The user uses the second hand 210 to gently pull the guide element 120 rearward, in order to position the guide element 120 in channel 194 (FIG. 13) on the dorsal surface of inserter element 130. The user must allow controlled slippage of the guide element 120 to allow the second hand to move rearward while maintaining light tension on guide element 120. The user then uses the thumb 214 of the first hand to trap the guide element 120 under light tension against the dorsal surface of the inserter element 130. This prevents the swallowable weight 158 from falling off of the inserter element 130.

In an optional step, the user may transfer the inserter element 130 and guide element 120 from the first hand to the second hand. Subsequent steps assume this has been done.

In another optional step, the user may apply one or more of an anesthetic (such as lidocaine), and a vasoconstrictor (such as epinephrine), to the absorbent material of the swallowable weight 158. The anesthetic numbs the passage to the stomach. The vasoconstrictor causes vasoconstriction of the nasal mucosa allowing for easier passage and decreased bleeding. This step may be performed, for example, by dipping the swallowable weight 158 into a container of these substances.

The anesthetic and vasoconstrictor agents may be packaged with the nasogastric tube insertion system 100, to promote their use. Also, the swallowable weight 158 may be pre-moistened with the anesthetic and vasoconstrictor agents by a manufacturer or distributor, to relieve the user of the burden of applying the agents, and to minimize the risk of contamination which might occur in bulk containers of the agents in a clinical environment.

Figure 16:
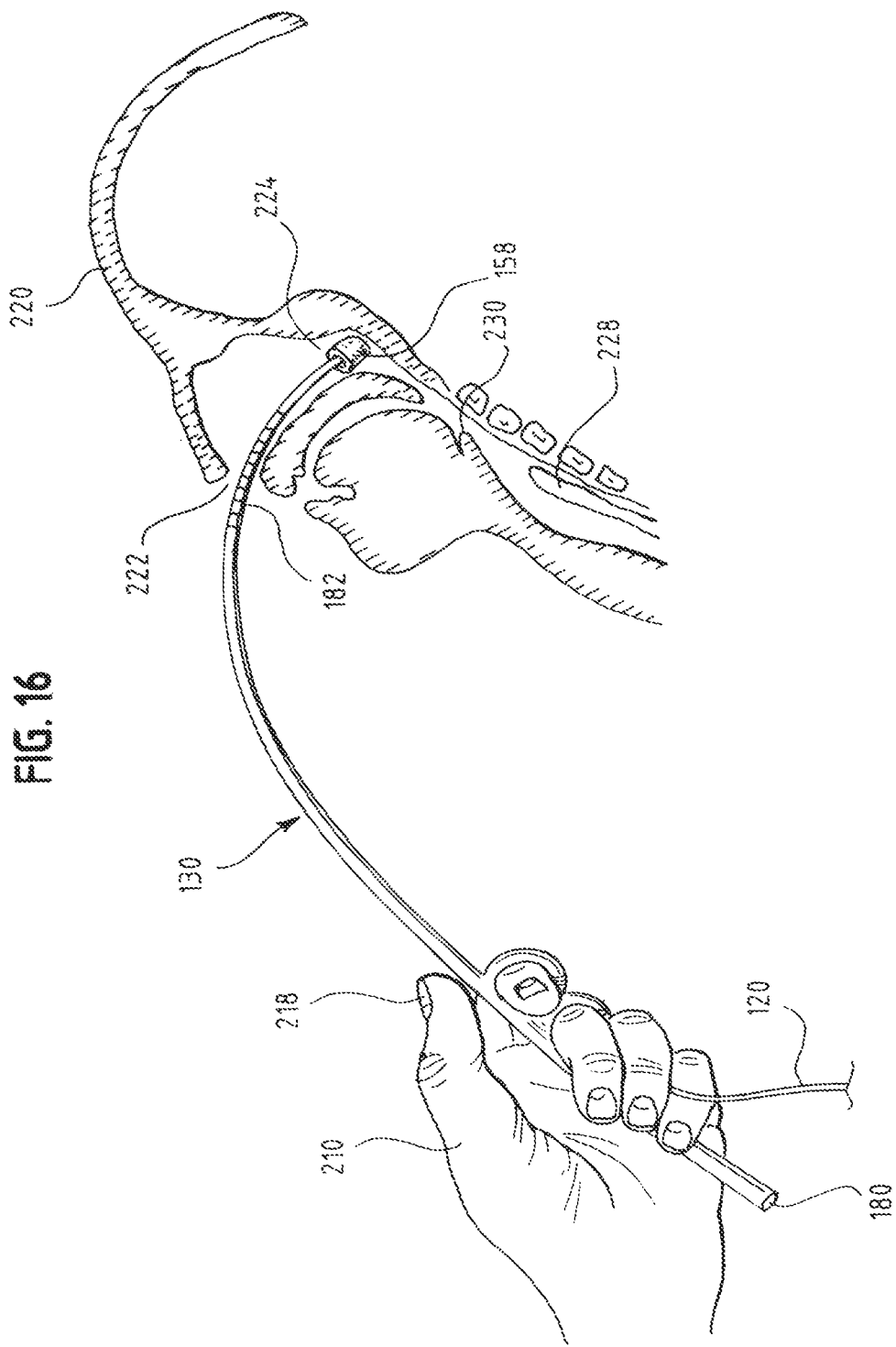
FIG. 16 is a side view and stylized partial cross-section view showing the inserter element 130 and guide element 120, depicting another stage in the method of inserting the nasogastric tube insertion system 100, in which the inserter element 130 and guide element 120 are being inserted through the patient's nasal passages to the nasopharynx or oropharynx.

A third group of steps 318 is generally depicted in FIG. 16. The user inserts the inserter element 130 and guide element 120 through the nostril 222 of patient 220, through the nasal passages, and into the oropharynx 224 (step 318). The user maintains pressure on guide element 120 using the thumb 218 during this process to keep the swallowable weight 158 in position. The user is preferably guided by measurement indicia 182 to insert the inserter element 130 to a predetermined insertion depth measured earlier. For most patients, an optimal predetermined insertion depth may be found by measuring the distance between the patient's earlobe and the tip of the patient's nose.

Figure 17:
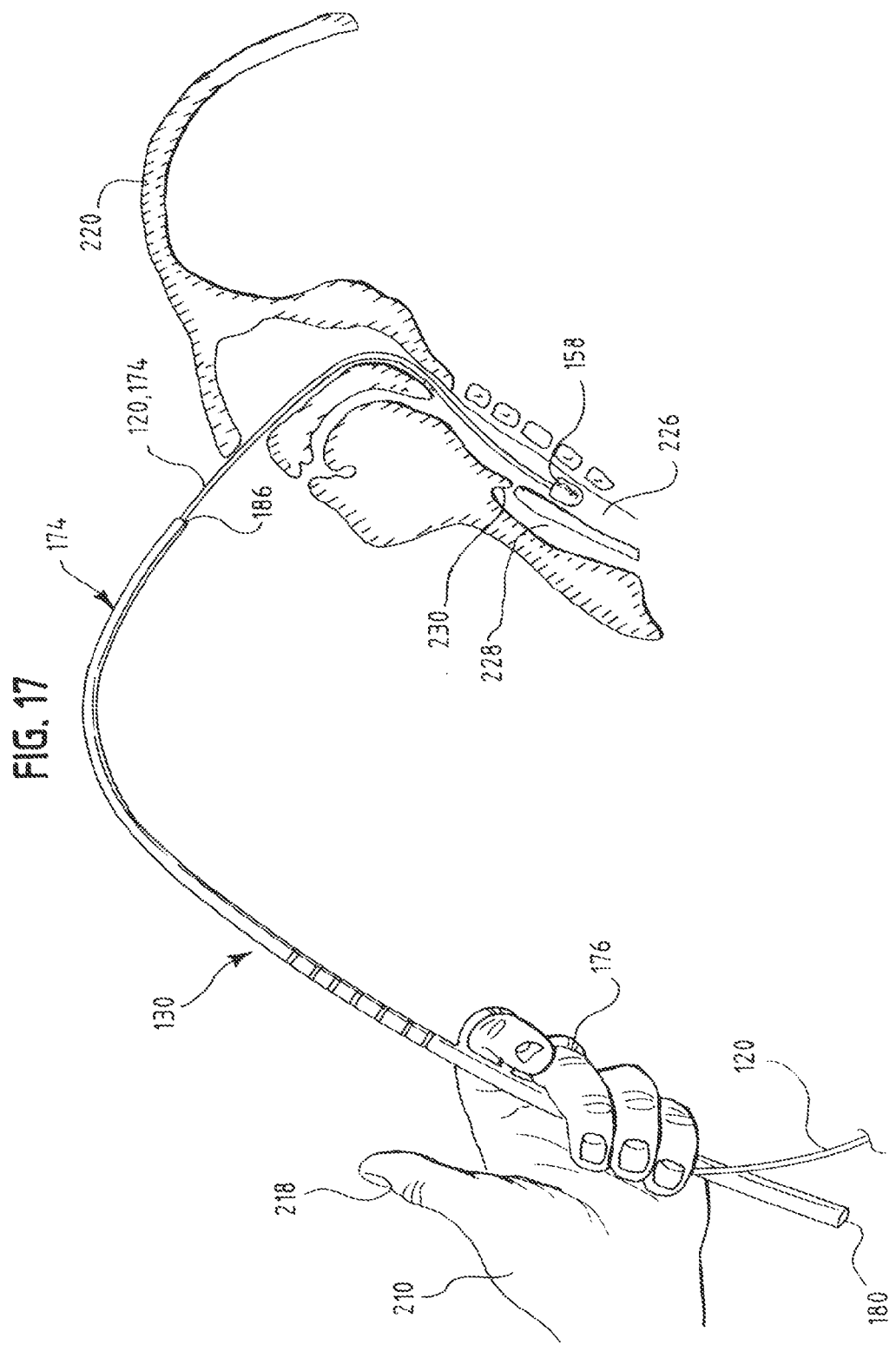
FIG. 17 is a side perspective view and stylized partial cross-section view showing the inserter element 130 and guide element 120, depicting another stage in the method of inserting the nasogastric tube insertion system 100, in which the inserter element 130 is removed and the swallowable weight 158 of the guide element 120 is being swallowed past the epiglottis.

A fourth group of steps 320, 322, 326 is generally depicted in FIG. 17. The user releases thumb 218, thereby relieving pressure on the guide element 120, and freeing the swallowable weight 158, allowing it to fall (steps 320, 322). At approximately the same time, the patient 220 is instructed to swallow the swallowable weight 158 (step 326). The patient may be given some water to sip to assist in swallowing. As a consequence of swallowing, the patient's epiglottis 230 covers the trachea 228, ensuring that the swallowable weight 158 is carried into the esophagus 226, and then into the stomach. The trailing section 152 and proximal end 150 of guide element 120 remains outside the patient. The user then removes the inserter element 130, which is no longer required for this procedure.

Although the steps heretofore described in connection with FIGS. 16-17 contemplate that the inserter 130 be used to place the swallowable weight 158 all the way into the patient's oropharynx 224, it may be preferable in some situations to use the inserter element 130 to place the swallowable weight 158 only part way into the nasal passages—that is, between the nostril 222 and the oropharynx 224. In an alternative submethod 310*a* according to an aspect of the present invention for use in conjunction with the nasogastric tube insertion system 100 of FIGS. 1-13, the steps of FIGS. 16-17 may be modified as follows: The user inserts the inserter element 130 and guide element 120 through the patient's nostril 222, and into a predetermined location in the nasal passages, but not as far as the oropharynx 224 (step 312*a*-318*a*). The user maintains pressure on guide element 120 using the thumb 218 during this process to keep the swallowable weight 158 in position (step 316).

The user is preferably guided by measurement indicia 182 to insert the inserter element 130 to a predetermined insertion depth measured earlier. For most patients, an optimal predetermined insertion depth may be found by measuring the distance between selected benchmarks on the patient's face or body. A shorter inserter element 130 may be used. The user releases thumb 218, thereby relieving pressure on the guide element 120, and freeing the swallowable weight 158 (steps 320, 322). The inserter element 130 may optionally be retracted, or it may be temporarily left in place to support the guide element 120 during advancement of the swallowable weight into the oropharynx.

The user applies gentle longitudinal pressure to guide element 120 to further advance the swallowable weight 158 into the oropharynx 224, noting by feel or by patient reaction when the weight has arrived in the desired position (step 324*a*). The patient is then instructed to swallow the swallowable weight 158 (step 326). The patient may be given some water to sip to assist in swallowing. As a consequence of swallowing, the patient's epiglottis 230 covers the trachea 228, ensuring that the swallowable weight 158 is carried into the esophagus 226, and then into the stomach. The trailing section 152 and proximal end 150 of guide element 120 remains outside the patient. The user then removes the inserter element 130, if present. The remaining steps of methods 310 and 310*a* are similar.

Figure 18:
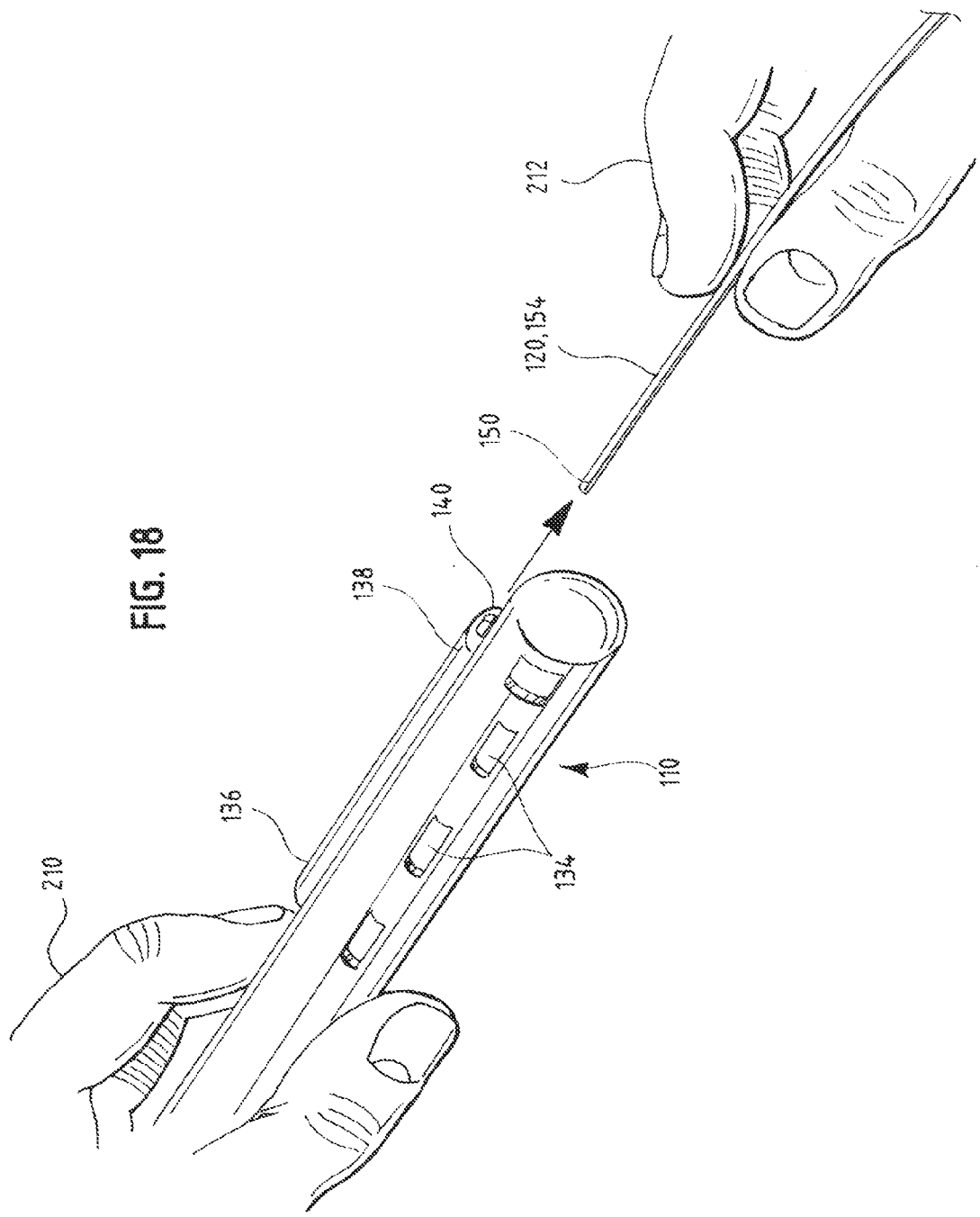
FIG. 18 is a side view showing the nasogastric tube 110 and the guide element 120, depicting another stage in the method of inserting the nasogastric tube insertion system 100, in which the guide element 120 is threaded through an opening of the guide element retaining structure 136 of the nasogastric tube 110.
Figure 19:
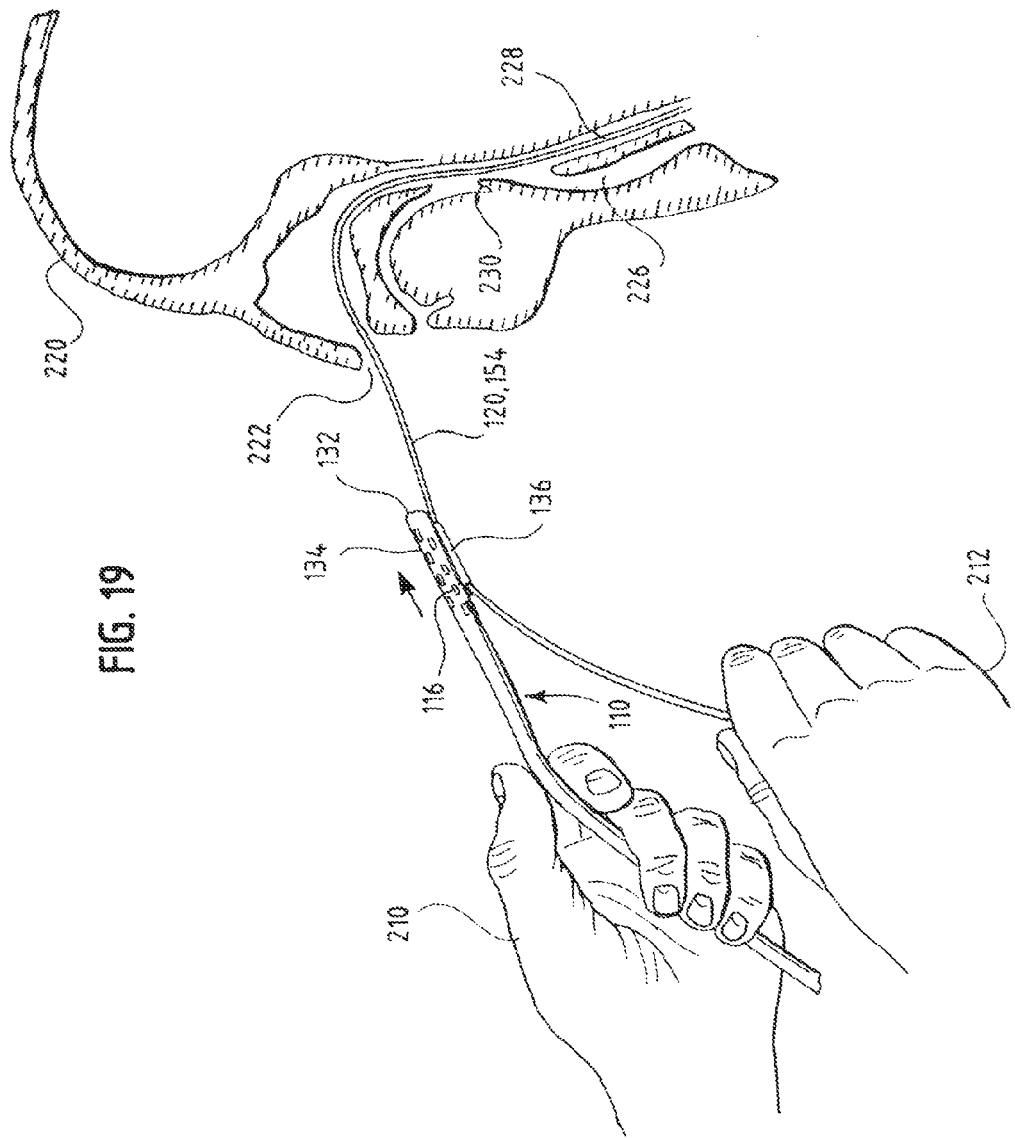
FIG. 19 is a side view and stylized partial cross-section view showing the nasogastric tube 110 and the guide element 120, depicting another stage in the method of inserting the nasogastric tube insertion system 100, in which the nasogastric tube 110 is pushed along the guide element 120 as the tube is inserted into the patient's nasal passage.

A fifth group of steps 328, 330 is generally depicted in FIG. 18. The user threads the proximal end 150 of the guide element 120 through the retaining section opening 140 of the guide element retaining structure 136 of nasogastric tube 110 (step 330). This step is optional; the nasogastric tube 110 may be supplied by the manufacturer, or otherwise distributed to the user, in the condition in which the guide element 120 is already telescoped through the guide element retaining structure 136.

A sixth group of steps 328, 332 is generally depicted in FIG. 20. Holding the guide element 120 firmly in a first hand 212, and the nasogastric tube 110 in a second hand 210, the user pushes the nasogastric tube 110 telescopically along the guide element 120. The user inserts the nasogastric tube 110 through the nostril 222 and the tube safely follows the path established by the guide element 120 into the patient's stomach (step 332). The guide element 120 and nasogastric tube 110 remain together until the nasogastric tube 110 is to be removed. Then, the nasogastric tube 110 and the guide element 120 are removed together. As described further in greater detail, in other embodiments, the guide element 120 may be removed prior to removing the nasogastric tube 110.

Although the shape of the swallowable weight 158 has been shown in FIG. 1 and as generally cylindrical, there may be situations in which a different shape is advantageous. Especially upon removal of the nasogastric tube 110 and guide element 120, a gentler transition from the thin leading section 154 of the guide element to the full diameter of the swallowable weight 158 may ease passage of the swallowable weight through the patient's esophagus, nasal passages, and the like, and may minimize damage to tissues and deterioration of the weight. FIG. 21 is an enlarged side view of an alternative embodiment 250 of the leading section of guide element 120. FIG. 21 also depicts an alternative embodiment 270 the insertion section of inserter element 130 which may advantageously be used in conjunction with the alternative leading section 250 of guide element 120. FIG. 22 is an enlarged cross-section view of the alternative leading section 250.

FIG. 23 is an enlarged perspective view of the tip 272 of the alternative insertion section 270 of inserter element 130 portion of the alternative leading section 250 of guide element 120. The features of these FIGS. 21-23 will generally be described together. Except for the points of departure mentioned in connection with FIGS. 21-23, guide element 120 and inserter element 130 may be constructed in the same manner, and may have the same properties, as generally described earlier.

As best seen in FIGS. 21-22, alternative leading section 250 preferably has a slender longitudinal portion similar to that of leading section 154 (FIG. 1). Alternative leading section 250 preferably also has a body 252 which may include a first section 254 of generally cylindrical shape adjacent to a second section 258 of generally conical shape at a transition 262. The front or leading edge 256 of body 252 may have a rounded or partially-spherical contour to aid insertion. It is not essential that the shape of the first section 254 be cylindrical, but it is preferable that it have sufficient diameter that the body 252 serve as a weight and be acted upon by the patient's swallowing mechanism, and it may be preferable that the contour be relatively free from large topological features that may interfere with anatomical structures during insertion. It is not essential that the shape of the second section 258 be conical, but is it preferable that its diameter gradually increase from that of the slender longitudinal portion of alternative leading section 250 to the full diameter of the body 252. The transition 262 from the first section 254 to the second section 258 may be so gradual as to be invisible, and these sections may be integrally constructed.

The body 252 is preferably securely attached to the slender longitudinal portion of alternative leading section 250 using an attachment structure 260. For example, the longitudinal portion of the alternative leading section 250 may extend into the body, and an attachment structure 260 may be formed as an anchor or other structure for securely mechanically engaging the body 252. However, the attachment structure 260 may also be formed as any part of leading section 250 in contact with body 252 and fastened thereto using any suitable fastening technology, including but not limited to glue, ultrasonic or chemical bonding or welding, structural features such as barbs or hooks, or a tight friction fit. The body 252 and the alternative leading section 250 may be constructed of materials and attached as described in connection with the swallowable weight 158 of the earlier-described embodiment.

As best seen in FIGS. 21 and 23, alternative insertion section 270 of inserter element 130 may include a relatively slender longitudinal portion 270 and a flared end portion 272 for engaging the body 252 of the swallowable weight of the alternative leading section 250 of guide element 130. The terminal end 276 of the flared end portion 272 may have a conical-concave shape to receive and engage the conical second section 258 of the alternative leading section 250 of the guide element 120. A slot extending along the dorsal surface of the alternative insertion section 270, formed by walls 280, and leading to a central lumen 282 forms a channel for receiving the longitudinal portion of alternative leading section 250, similar in structure and operation to channel 194 of insertion section 174 (FIG. 13).

Although slot 270 and central lumen 282 are shown as separate structures, they could also be formed as an integral U-shaped channel or any other appropriate structure for receiving the longitudinal portion of alternative leading section 270.

It is not essential that the shape of the terminal end 276 exactly mate with the second section 258 of alternative leading section 250, but it is important that the shape be compatible so that when light tension is provided on guide element 120, the body 252 of the alternative leading section 250 is retained on the end of the alternative insertion section 270, and when such tension is released, the body 252 of the alternative leading section falls away. The alternative leading section 250 may be constructed of materials as described in connection with leading section 174 the earlier-described embodiment.

One of skill in the art will appreciate that nasogastric tubes of various designs and functions may be inserted using the inserter element 130, the guide element 120, and the associated methods described earlier. In accord with a further aspect of the present invention, a nasogastric tube adapted for use as a feeding tube may be advantageously used with the aforementioned elements. Feeding tubes are used by medical practitioners in a number of situations, including those where the patient is unable to feed himself or herself, and those where the patient lacks desire to feed.

A nasogastric feeding tube is generally similar to the earlier-described nasogastric tube 110, but has several differences to accommodate its use as a feeding tube. A nasogastric feeding tube generally has a distal end intended for placement into the patient's stomach, a proximal end intended to remain outside the patient, and a main tubular section joining the distal and proximal ends. Because feeding tubes are often left in position in the patient for an extended period, and the tubes are typically used to deliver fluid under slight positive pressure but are not subject to suction, the main tubular section is usually constructed of very flexible material having thin walls to minimize damage and discomfort to the patient. The feeding tube diameter is often smaller than that of other types of nasogastric tube. Typical feeding tubes have a single lumen, but some feeding tubes have more lumina and some feeding tubes are adapted to permit suction to be used to remove material from the stomach.

Figure 24:
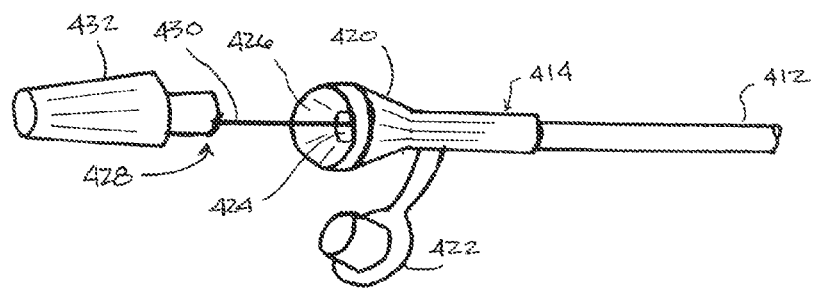
FIG. 24 is a side perspective view of a first embodiment of a proximal end section of an alternate nasogastric tube, in the form of a nasogastric feeding tube, for use in conjunction with the guide element 120 and inserter element 130 of the present invention.
Figure 25:
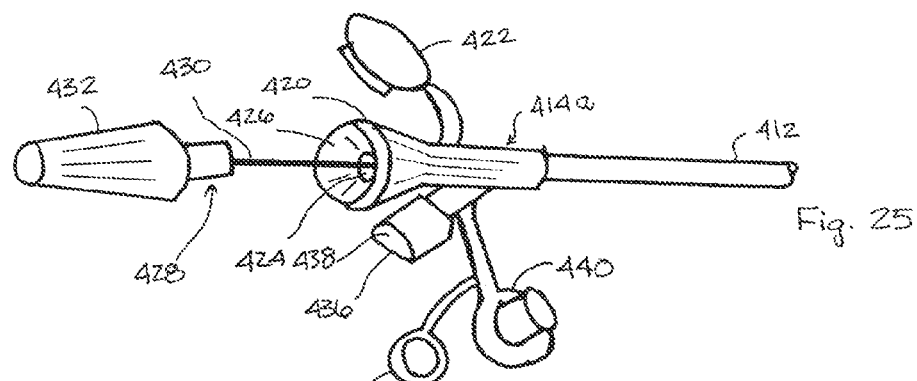
FIG. 25 is a side perspective view of a second embodiment of a proximal end section of an alternate nasogastric tube, in the form of a nasogastric feeding tube, for use in conjunction with the guide element 120 and inserter element 130 of the present invention.
Figure 26:
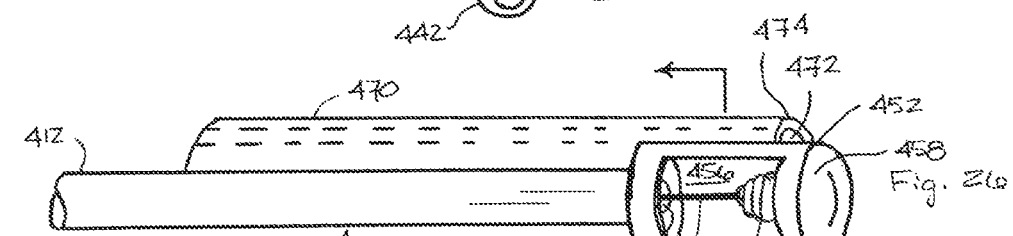
FIG. 26 is a side perspective view of a first embodiment of a distal end section of an alternate nasogastric tube, in the form of a nasogastric feeding tube, for use in conjunction with the guide element 120 and inserter element 130 of the present invention.
Figure 27:
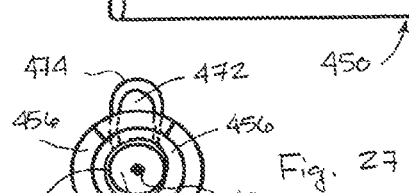
FIG. 27 is a cross section view of the distal end section of FIG. 26, taken along the section lines 27-27 thereof.
Figure 28:
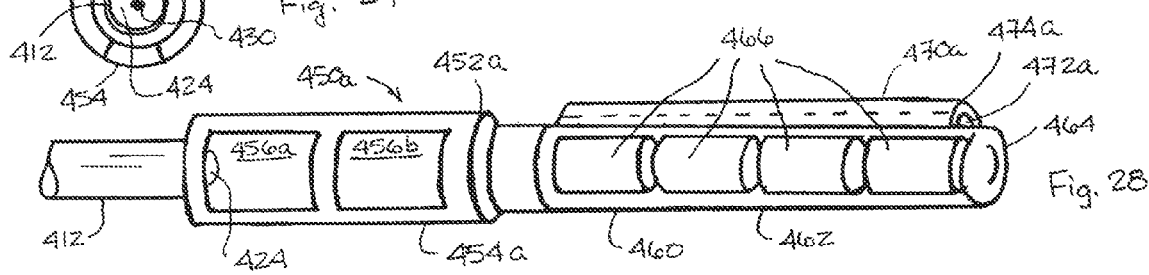
FIG. 28 is a side perspective view of a second embodiment of a distal end section of an alternate nasogastric tube, in the form of a nasogastric feeding tube, for use in conjunction with the guide element 120 and inserter element 130 of the present invention.
Figure 29:
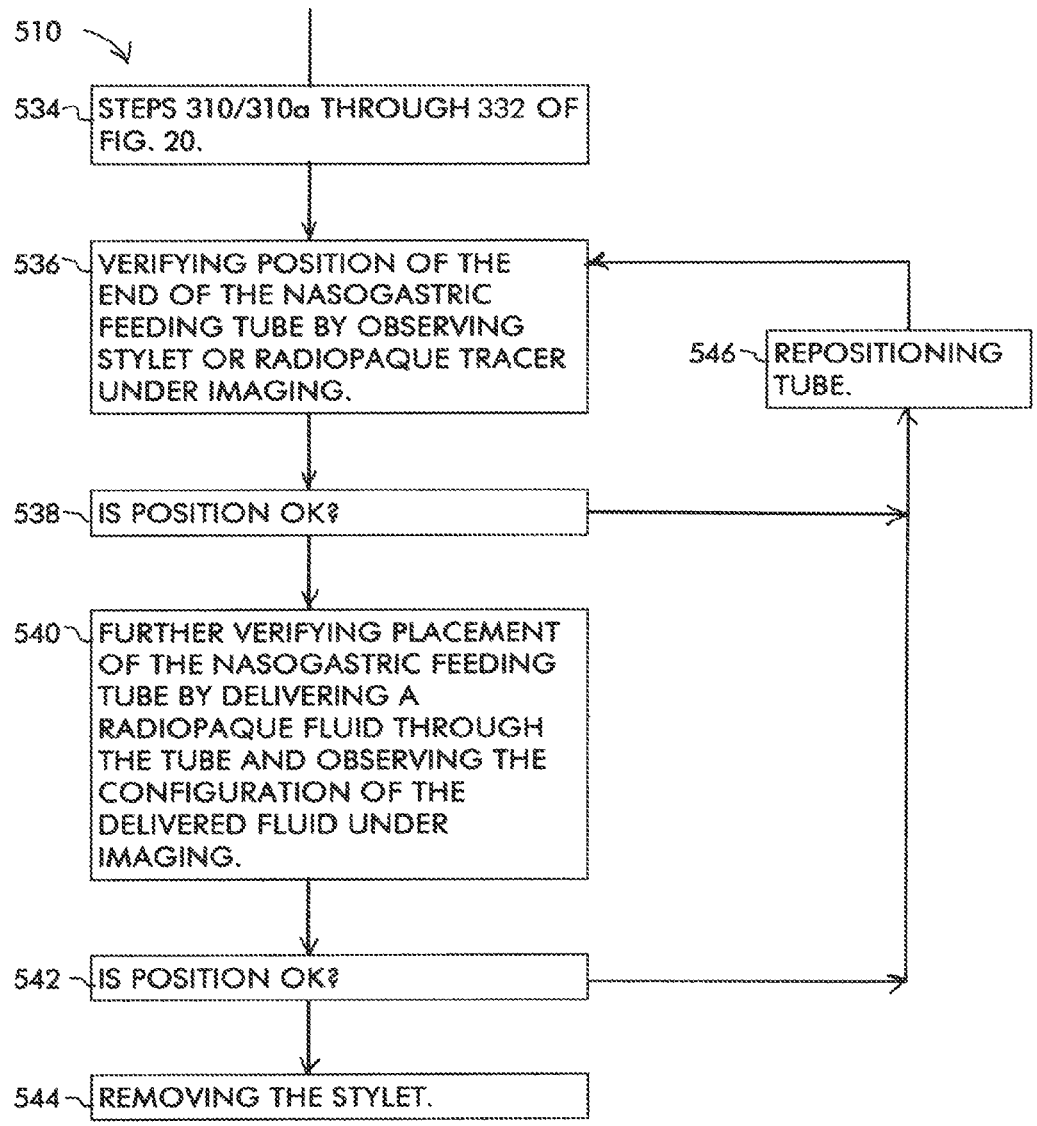
FIG. 29 is a flow diagram depicting steps of exemplary methods 510, 510a of inserting the nasogastric tube insertion system 100 into the patient using a nasogastric feeding tube of the type shown in FIGS. 24-28.

FIGS. 24 and 25 are side perspective views of first and second embodiments 414 and 414a, respectively, of proximal end sections of a nasogastric feeding tube which may be used as the nasogastric tube portion of a nasogastric tube insertion system, similar to the nasogastric tube insertion system 100 earlier described. FIGS. 26 and 28 are side perspective views of first and second embodiments 450 and 450a, respectively, of distal end sections of a nasogastric feeding tube which may be used as the nasogastric tube portion of a nasogastric tube insertion system. That is, a feeding tube having any of the proximal ends 414 or 414a, and any of the distal ends 450 or 450a, may be substituted for the feeding tube 110 of nasogastric tube insertion system 100, and used in conjunction with the guide element 120 and inserter element 130 the present invention. FIG. 27 is a cross section view of the distal end section of FIG. 26, viewed toward the proximal end.

Although not shown in the drawings as an integrated unit, the proximal end of the feeding tube is connected to its distal end by the main tubular section 412, and that section is sufficiently long that the distal end may rest in the patient's stomach while the proximal end extends a distance from the patient's nostril to accommodate a connection to a source of nutritional material or other fluid. The main tubular section 412 may be formed as a single integrated component or may be constructed as an assembly of longitudinally mated subsections. Similarly, the main tubular section 412, proximal end 414 or 414a, and distal end 450 or 450a may be formed as an integrated unit, or may be constructed as separate components and mated together prior to use. The assembly of separate sections may be performed during manufacturing or by the user.

As best seen in FIG. 24, a first embodiment 414 of a feeding tube proximal end includes at least one terminal port housing 420 coupled to the main tubular section 412. The port housing 420 has an opening 426 that forms a port adapted for connection to a source of fluid material (e.g., any appropriate nutritional, hydration, irrigation, or drug product material in fluid form), via appropriate tubing or a connector thereon (not shown). The opening 426 communicates with a lumen 424 of the main tubular section 412, which lumen extends to the distal end of the feeding tube. The opening 426 may have a concave or funnel shape or other appropriate shape for mating with the tubing or connector from the fluid source. A flexible cap 422 is preferably tethered to the housing 420 to allow the opening 424 to be closed to avoid entry of foreign matter.

In feeding tubes which are not designed for use with suction, the walls of the main tubular section 412 may be quite thin and extremely flexible. As a result, it is difficult or impossible to insert the feeding tube though the nasal passages, oropharynx, esophagus, and the like, because any forward pressure on the tube causes it to bend. As best seen in FIG. 24, an optional stylet 428 may be provided to temporarily stiffen the feeding tube to facilitate insertion. The stylet 428 has a handle 432 and a thin wire 430 attached thereto. The stylet wire 430 extends through the lumen 424 of main tubular section 412 to the distal end of the feeding tube. The wire 430 adds stiffness, so that forward pressure may be applied to the tube to advance it into the patient. Where a stylet is used, it may be installed into the feeding tube by a medical professional performing the insertion procedure, or may preferably be installed by the device manufacturer.

If the main tubular structure 412 is constructed of a soft, flexible material, the terminal port housing 420 and related elements are preferably constructed of a suitable stiffer material. Also, if the feeding tube is intended for additional uses, including suction, the walls of the main tubular section 412 may be thicker and constructed of a stiffer, less flexible material. Further, the terminal port housing 420 could be formed integrally with the main tubular section 412 by incorporating one more ports at or near the proximal end thereof.

As best seen in FIG. 25, a second embodiment 414a of a proximal end of a feeding tube is generally constructed in a manner similar to that of the first embodiment, and therefore, only the differences between the two will be described.

The second embodiment 414a has a second port extension 436 that forms a port adapted for connection to an additional source of fluid material via appropriate tubing or a connector thereon (not shown). The second port extension 436 has an opening 438 in communication with the lumen 424 of main tubular section 412. A cap 440 is preferably tethered to the housing 420 to allow the opening 438 to be closed. An adaptor 442 may also be tethered to the housing 420 or to the cap 440. The adaptor 442 may be optionally inserted into the opening 438 to accommodate a second size or configuration of tubing or connector from the additional fluid source. The second port allows additional fluid to be introduced without disconnecting the first source from the first port. For example, an irrigating fluid may be introduced to clear blockage in the main tubular section.

As best seen in FIGS. 26-27, a first embodiment 450 of a distal end section of a feeding tube has an exit port housing 452 coupled to the main tubular section 412. The housing 452 may have a generally hollow cylindrical shape including a blunt convex tip 458 and cylindrical walls 454 forming a chamber in communication with lumen 424 of the main tubular section 412. Other shapes for housing 452 could also be used. At least one exit "window" or opening 456 is provided in the housing 452 to allow fluid carried by main tubular section 412 to escape the chamber. As best seen in FIG. 27, two opposed window openings may be provided, but any other appropriate configuration could also be used.

Stylet wire 430 extends into the housing and terminates in an end structure 434. The end structure 434 is preferably shaped to removably engage a portion of the housing during feeding tube insertion and to avoid puncturing the feeding tube when the stylet is withdrawn after the feeding tube has been successfully inserted into a desired position. For example, the end structure 434 may be constructed as a tight helical winding of the end of wire 430 into a conical shape. Other shapes and structures could also be used. The stylet may be radiopaque to allow it to be seen using an appropriate imaging procedure.

The distal end section 450 of the feeding further comprises a guide element retaining structure 470 adapted to move slidably along guide element 120, similar to that the guide element retaining structure 136 of FIGS. 1 and 10. The guide element retaining structure 470 preferably comprises a generally tubular protrusion or intrusion attached and parallel to the exit port housing 452 and a portion of the main tubular section 412. The guide element retaining structure 470 has a tubular opening 472 to receive the guide element 120. Once the guide element has been inserted, the guide element retaining structure 470 allows the feeding tube to move slidably and telescopically along the guide element 120. Thus, the guide element 120 may serve to establish a path for the feeding tube to follow as it is inserted through the patient's nasal passages, oropharynx, esophagus, and into the patient's stomach. The leading end 474 and the trailing end of the guide element retaining structure 470 are preferably chamfered to avoid abrading or irritating tissues which are encountered as the feeding tube is inserted and removed.

Although the guide element retaining structure 470 is shown in FIG. 26 and described herein as a tubular element attached to the exit port housing 452 and a portion of the main tubular section 412, the guide element retaining structure could extend only along the exit port housing 452. In addition, structures could also be used to form the guide element retaining structure 470 adapted for slidable and/or telescopic movement along the guide element 120. For example, the guide element retaining structure 470 could be formed as one or more loops or retaining tabs attached to the exit port housing 452. For another example, the guide element retaining structure 470 could be formed as a tunnel-style bore through an unused portion of the cross section of the exit port housing. This configuration has the advantage that no enlargement of the exit port housing 452 is needed, but it may not be possible to implement if the housing is crowded. As a further alternative to a separate structure 470 dedicated to retaining the guide element 120, features of the exit port housing 452 or the main tubular section 412 may be used to form a guide element retaining structure. For example, guide element 120 could be threaded or telescoped through an aperture placed at or adjacent the tip 458 of the exit port housing 452 of the feeding tube, extend through the chamber, and could exit through one of exit "window" openings 456.

If the main tubular section 412 is constructed of a soft, flexible material, the exit port housing 450 and related elements are preferably constructed of a stiffer material.

Also, if the feeding tube is intended for additional uses, including suction, the walls of the main tubular section 412 may be thicker, and a channel or lumen may be formed therein. Further, the exit port housing 452 could be formed integrally with the main tubular section 412 by incorporating one more exit ports at or near the end thereof.

As best seen in FIG. 28, a second embodiment 450a of a distal end of a feeding tube is generally constructed in a manner similar to that of the first embodiment, and therefore, only the differences between the two will be described.

The second embodiment 450a of a distal end section comprises an exit port housing 452a coupled to the main tubular section 412 and a weight section 460 attached to the exit port housing 452a. The housing 452a may have a generally hollow cylindrical shape with cylindrical walls 454a forming a chamber in communication with lumen 424 of the main tubular section 412. Because the weight section 460 is attached to the end of the housing 452a, any suitable end configuration of the housing may be used. A plurality of exit "windows" or openings 456a, 456b, etc., may be provided in the housing 452a to allow fluid carried by main tubular section 412 to escape the chamber. The stylet wire is not shown. The weight section 460 is a generally tubular structure having a cylindrical wall 462 and a blunt tip 464. Other appropriate structural configurations could also be used. One or more weights may be provided interior of walls 462 to facilitate insertion and to maintain the position of the distal end section thereafter. The weights are preferably radiopaque to allow them to be seen under an appropriate imaging procedure. Any other appropriate configuration of exit openings and weights could also be used. For example, a single section could incorporate the weights in the chamber, using a plurality of smaller exit opening to allow escape of fluid while retaining the weights.

A guide element retaining structure 470a is preferably formed on the outside of the weight section 460. The guide element retaining structure 470a preferably comprises a generally tubular protrusion or intrusion attached and parallel to the weight section 460. The guide element retaining structure 470a has a tubular opening 472a to receive the guide element 120. The guide element retaining structure 470a may also be located on the exit port housing 452a, or any of the aforementioned alternatives for the configuration of the guide element retaining structure 470 could also be used.

Although the feeding tube has been described herein as having a single lumen, multiple lumina could be used by providing appropriate terminal and exit ports at proximal and distal ends, respectively. For example, some feeding tubes are used simultaneously to introduce nutritional, hydrating, or irrigational materials, while withdrawing other fluids. If suction is used, it is necessary to select suitable materials and thickness for the walls of the corresponding lumen to avoid collapse. The main tubular section 412 may be provided with a radiopaque tracer strip, wire, or other markings, to allow the position of the feeding tube to be verified even if no stylet or weights are used.

The nasogastric feeding tube may be inserted using a method similar to that described earlier in connection with nasogastric tube 110, but preferably incorporates additional steps of verifying correct positioning of the distal end of the tube. The patient must be cooperative and must be able to swallow. Determining this is a clinical decision that must be made by a medical professional at the time the feeding tube is needed.

According to a further aspect of the invention, FIG. 20 is a flow diagram showing the steps of an example method 510 for inserting a nasogastric feeding tube in conjunction with the a nasogastric tube insertion system described herein. Step 534 encompasses all the steps of either method 310 or 310a of FIG. 20, with corresponding elements of a nasogastric feeding tube substituted for the elements of nasogastric tube 110. At the end of step 534, the feeding tube is believed to have been initially placed into position in the patient's stomach.

In practice, feeding tubes are often incorrectly placed in the patient's duodenum, esophagus, or lungs. Improper placement of a feeding tube in the lungs is extremely dangerous, because the nutritional material can fill the lungs, preventing the patient from breathing, causing permanent lung damage, and in a significant fraction of cases, causing death. Accordingly, it is usually appropriate to verify correct placement using a conventional X-Ray or fluoroscopy. In step 536, a medical professional verifies the position of the distal end section 450 or 450a by observing the position of the stylet end, weights, or the radiopaque tracer using an appropriate imaging modality, such as conventional X-Ray or fluoroscopy. In step 538, the medical professional determines whether the position is acceptable, and if so, the method continues in step 538. If the position is wrong, the method continues in step 546.

Step 540 is a further optional position check. In step 540, a radiopaque substance, such as gastrografin may be delivered through the tube, while the patient is examined under fluoroscopy or another appropriate imaging modality. The pattern of diffusion of the radiopaque substance may be observed to determine whether the distal end section 450 or 450a has been properly inserted into the stomach, or improperly, e.g., into the duodenum or the esophagus. In step 542, the medical professional determines whether the position is acceptable, and if so, the method continues in step 544. In step 544, the stylet is removed, and the feeding tube is ready for use. If the position is determined to be wrong, the method continues in step 546.

If, in steps 538 or 542, the position is determined to be wrong, the method continues in step 546. The tube is repositioned, and the method returns to step 536, where the position is again verified.

In some instances, it may be desirable to remove the guide element, while the nasogastric tube remains in position in the patient.

According to a further aspect of the invention, a guide element may be provided having a swallowable weight which may be retracted while the nasogastric tube remains in position. The weight may, for example, be constructed in a way that allows it to change shape or form to enable its retraction through a guide element retaining structure or through the nasogastric tube itself. A nasogastric tube that is adapted to facilitate the withdrawal of the guide element may also be provided.

Figure 30:
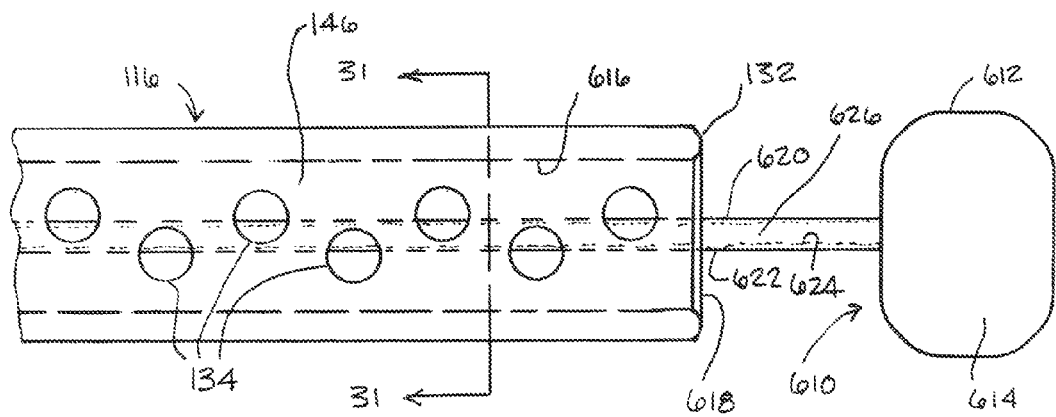
FIG. 30 is a side view showing the leading section of an alternate embodiment of a guide element, and the distal end of an alternate embodiment of a nasogastric tube, constructed according to an aspect of the present invention.
Figure 31:
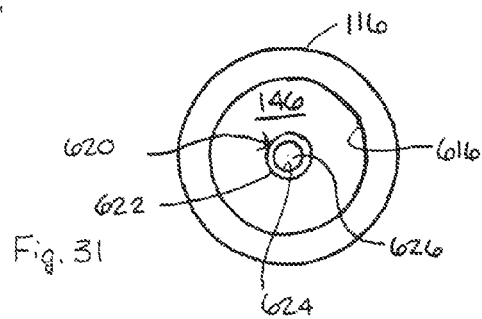
FIG. 31 is a cross section view of the alternate embodiments of the guide element and nasogastric tube of FIG. 30, taken along the section lines 31-31 of FIG. 30.
Figure 32:
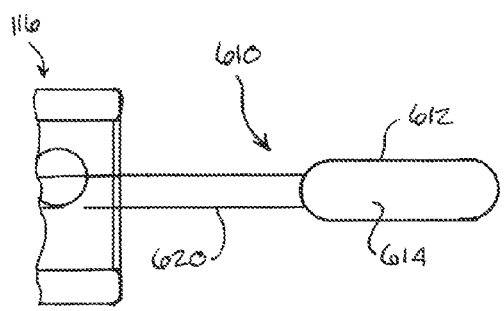
FIG. 32 is a side view showing the alternate embodiments of the guide element and nasogastric tube of FIGS. 30 and 31, showing a weight element thereof in a deflated condition.

According to an aspect of the invention, there is shown in FIG. 30 a side view of the leading section of an alternate embodiment of a guide element, and the distal end of an alternate embodiment of a nasogastric tube, in which the weight is formed as an inflatable sac or balloon, showing the weight in an inflated condition. FIG. 31 is a cross section view of the alternate embodiments of the guide element and nasogastric tube of FIG. 30. taken along the section lines 31-31 of FIG. 30; FIG. 32 is a side view showing the alternate embodiments of the guide element and nasogastric tube of FIGS. 30 and 31, showing the weight a deflated condition.

As best seen in FIGS. 30-32, the distal end section 116 of an alternate embodiment of a nasogastric tube may be formed having at least one lumen 146. The alternate embodiment of the nasogastric tube may generally be constructed as heretofore described in connection with nasogastric tube 110, with modifications as described in this section. Lumen 146 has an inner wall 616, an end opening 618, and a number of side openings or apertures 134. The end and side openings 618 and 134 allow communication of fluids between the lumen and the exterior of the tube. The surfaces of the leading end 132 of the nasogastric tube in the area of the end opening 618 are preferably rounded or smoothed to avoid abrasion or other injury to the patient during insertion of the tube. The particular configuration, including size and arrangement, of the openings shown is an example and may vary in different embodiments. Although only a single lumen is shown, the nasogastric tube could have any appropriate number and size of lumina.

An alternate embodiment 610 of a guide element preferably comprises an inflatable guide element swallowable weight body envelope 612 coupled to a substantially hollow guide element tube 620. The body envelope 612 encloses an interior space 614 for containing fluid, which may be any appropriate gas, such as air, or liquid, such as water. The guide element tube 620 preferably has an exterior wall 622 and inner wall 624 forming a guide element tube lumen 626, which is preferably arranged for fluid communication between the lumen 626 and the interior 614. Swallowable weight body envelope 612 may be inflated by introducing fluid into lumen 626 at the proximal end (not shown) of the guide element 610, as depicted in FIG. 30. The swallowable weight body envelope 612 may be deflated by withdrawing fluid (or allowing the fluid to withdraw) from lumen 626, as depicted in FIG. 32.

The distal end of alternate guide element 610 preferably extends through lumen 146. Lumen 146, or at least one of the lumina if there are several, is preferably large enough to allow passage, for example via slidable movement therethrough, of the alternate embodiment of guide element 610, including the guide element tube 620 and the swallowable weight in its deflated form. Thus, the alternate embodiment of guide element 610 may be withdrawn from the patient while the nasogastric tube remains in a desired position therein.

The body envelope 612 may be constructed of any suitable flexible material which is bio-compatible for insertion in a patient (human) or subject (animal) and compatible with stomach fluids, including but not limited to latex. The body envelope 612 may be formed from an expandable resilient material, similar to that of a conventional balloon, or from a material that does not resiliently expand, such as a bag or pouch. The materials considered appropriate may vary depending on locality-specific practice and regulation. Guide element tube 620 may be constructed from any suitable flexible material which is bio-compatible for insertion in a patient and compatible with stomach fluids, and which has sufficient strength and rigidity to allow its safe insertion into and withdrawal from the patient. For example, guide element tube 620 may be constructed of a silicone elastomer, but other materials could also be used. The materials considered appropriate may vary depending on locality-specific practice and regulation.

The alternate embodiment of the nasogastric tube system, including the alternate embodiment of the guide element, of FIGS. 30-32 may be inserted in the same manner as earlier-described embodiments. Although the alternate embodiment 610 of the guide element is depicted in FIG. 30-32 as extending through the main lumen of the nasogastric tube, which thus serves as a guide element retaining structure, any lumen, or a guide element retaining structure similar to the retaining structure 136 of FIG. 1, could also be used.

According to a further aspect of the invention, the swallowable weight of the guide element may be constructed from a material which ablates, e.g., via dissolution, disintegration, melting, etc., in the presence fluids present in the patient's stomach to allow the remainder of the guide element to be withdrawn without disturbing the position of the nasogastric tube.

According to an aspect of the invention, there is shown in FIG. 33 the leading section of an alternate embodiment 630 of a guide element with a swallowable weight thereof having a first example configuration. The alternate embodiment 630 of the guide element of FIG. 33 may generally be constructed as heretofore described in connection with guide element 120, with modifications as described in this section. The guide element 630 preferably comprises a guide element leading section 154 generally constructed as earlier described. A swallowable weight in a first example configuration 640 is attached to the guide element leading section 154 near the end 648 thereof. In the first example configuration, swallowable weight 640 preferably has a generally cylindrical body section 642, an end section 644 having rounded or smoothed corners, and a conical tail section 646. However, other configurations could also be used. The rounded or smoothed corners help avoid abrasion or other injury to the patient during insertion, removal, or swallowing of the guide element 630. The conical tail section 646 may mate or engage a corresponding structure on the insertion section 174 of inserter element 130. This prevents the swallowable weight 640 from falling off the end of inserter element 130 if some slack occurs in the guide element 120.

Swallowable weight 640 is preferably constructed from a material that ablates in the presence of stomach fluids or the temperature present in the body. The term "ablate" and terms derived therefrom are used herein to refer to any process where the material of the swallowable weight 640, initially in a solid or cohesive form, dissolves, disintegrates, melts, sublimates, decomposes, falls away, erodes, softens to allow reshaping with minimal force, or the like, when exposed to stomach fluids or to the temperature present in the body, such that thereafter, the weight either no longer exists as a relatively solid mass attached to the guide element 120 or no longer provides a barrier or resistance to withdrawal of the guide element without disturbing the nasogastric tube. The ablation preferably occurs within a short time after arrival of the swallowable weight 640 in the stomach, and does not require digestion of the weight. The time acceptable for the ablation to occur may depend on the application but may, for example, be less than about five minutes. The material is preferably bio-compatible for insertion in the patient. Prior to exposure to stomach fluids, the material is preferably substantially solid; however, the material may exhibit a rigidity within a range extending from completely rigid to a rubbery or gelatinous flexibility. The swallowable weight 640 may be formed using any appropriate method and technology, including but not limited to molding, casting, depositing, precipitating, compressing, or sintering the material about the end 648 of guide element leading section 154. The swallowable weight 640 may be formed, for example, from a liquid or fluid material which sets due to chemical action or temperature, including a gelatin. An example of such a material which is known for use for pharmaceutical formulations and approved in the U.S. is a gelatin compound, which may include glycerin. The swallowable weight 640 may also be formed from a powder which is compressed or sintered to form a generally solid mass. An example of such a material which is known for use for pharmaceutical formulations and approved in the U.S. is compressed glucose. Other materials could also be used, and any appropriate manner of coupling or attaching the swallowable weight 640 to the guide element leading section 154 could be used. The leading section 154 could also be constructed of a material that is soluble in stomach fluids, or disintegrates or becomes extremely soft when exposed to stomach fluids, or changes from a solid to liquid state when exposed to stomach fluids.

According to an aspect of the invention, there is shown in FIG. 34 the leading section of an alternate embodiment 632 of a guide element with a swallowable weight thereof having a second example configuration. The guide element 632 of FIG. 34 may generally be constructed as heretofore described in connection with guide element 630, with modifications as described in this section. The guide element 632 preferably comprises a guide element leading section 154 generally constructed as earlier described. A swallowable weight in the second example configuration 650 is attached to the guide element leading section 154 near the end 648 thereof. In the second example configuration, swallowable weight 650 preferably has a generally cylindrical body section 652, an end section 644 having rounded corners, and a tail section 654 also having rounded corners. However, other configurations could also be used. Swallowable weight 650 may be constructed and may use materials as earlier described for swallowable weight 640.

According to an aspect of the invention, there is shown in FIG. 35 the leading section of an alternate embodiment 634 of a guide element with a swallowable weight thereof having a third example configuration. The guide element 634 of FIG. 35 may generally be constructed as heretofore described in connection with guide element 630, with modifications as described in this section. The guide element 634 preferably comprises a guide element leading section 154 generally constructed as earlier described. A swallowable weight in the third example configuration 656 is attached to the guide element leading section 154 near the end 648 thereof. In the third example configuration, swallowable weight 656 preferably has a generally cylindrical body section 658, an end section 644 having rounded corners, and a tail section having a concave conical wall 660 forming a generally conical opening 662. The opening 662 facilitates a loose engagement of the swallowable weight 656 with the insertion section 174 of inserter element 130 in a manner similar to that shown in FIG. 12 and described in connection therewith. This prevents the swallowable weight 656 from falling off the end of the inserter element 130 if some slack occurs in the guide element 120. Other configurations of swallowable weight 656 could also be used. Swallowable weight 656 may be constructed and may use materials as earlier described for swallowable weight 640.

According to an aspect of the invention, there is shown in FIG. 36 the leading section of an alternate embodiment 636 of a guide element with a swallowable weight thereof having a second example configuration. The guide element 636 of FIG. 34 may generally be constructed as heretofore described in connection with guide element 630, with modifications as described in this section. The guide element 636 preferably comprises a guide element leading section 154 generally constructed as earlier described. A swallowable weight in the fourth example configuration 664 is attached to the guide element leading section 154 near the end 648 thereof. In the fourth example configuration, swallowable weight 664 preferably has a generally cylindrical body section 666, an end section 644 having rounded corners, and a tail section having an end wall 668, a cylindrical inner wall 670, and a base wall 672, forming a generally cylindrical depressed opening 674. The opening 674 facilitates a loose engagement of the swallowable weight 664 with the insertion section 174 of inserter element 130 in a manner similar to that shown in FIG. 12 and described in connection therewith. This prevents the swallowable weight 664 from falling off the inserter element 130 if some slack occurs in the guide element 120. The corner between body section 666 and tail section end wall 668 is preferably rounded or smoothed to avoid abrasion or other injury to the patient during insertion, removal, or swallowing of the guide element 636. However, other configurations of swallowable weight 664 could also be used. Swallowable weight 650 may be constructed and may use materials as earlier described for swallowable weight 640.

According to a further aspect of the invention, retaining structures may be provided on the guide element leading section 154 near the end 648 thereof to improve engagement between the leading section 154 and the swallowable weight, e.g., 640, 650, 656, 654. The retaining structures may be needed or helpful if the material from which the swallowable weight is constructed is not completely rigid, or if the material does not adhesively attach to the surface of guide element leading section 154.

According to an aspect of the invention, there is shown in FIG. 37 a side view of an example embodiment 676 of the leading section 154 of the guide element 120 having retaining structures 678 constructed thereon. In this example embodiment 676, the retaining structures 678 are formed as disk-shaped elements extending transversely from the leading section 154 near the end 648 thereof. Any appropriate swallowable weight (not shown) may be used with the retaining structures 678, and the weight preferably surrounds the retaining structures, at least until the weight arrives in the patient's stomach.

According to an aspect of the invention, there is shown in FIG. 38 a side view of an example embodiment 680 of the leading section 154 of the guide element 120 having retaining structures 682 constructed thereon. In this example embodiment 680, the retaining structures 682 are formed as generally conical cup-shaped elements extending from the leading section 154 near the end 648 thereof. Any appropriate swallowable weight (not shown) may be used with the retaining structures 682, and the weight preferably surrounds the retaining structures, at least until the weight arrives in the patient's stomach.

Figure 39:
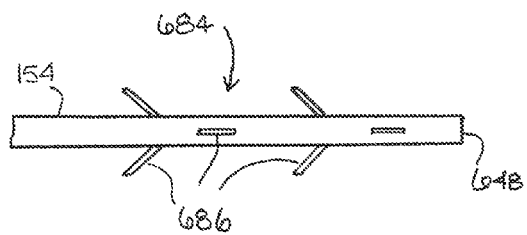
FIG. 39 is a side view showing the leading section of an alternate embodiment of a guide element before the weight element thereof is installed, depicting a third example configuration of members for retaining the weight element.

According to an aspect of the invention, there is shown in FIG. 39 a side view of an example embodiment 684 of the leading section 154 of the guide element 120 having retaining structures 686 constructed thereon. In this example embodiment 684, the retaining structures 686 are formed as spike-shaped elements extending from alternate radial positions of the leading section 154 near the end 648 thereof. Any appropriate swallowable weight (not shown) may be used with the retaining structures 686, and the weight preferably surrounds the retaining structures, at least until the weight arrives in the patient's stomach.

Figure 40:
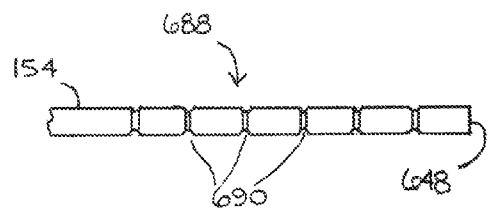
FIG. 40 is a side view showing the leading section of an alternate embodiment of a guide element before the weight element thereof is installed, depicting a fourth example configuration of members for retaining the weight element.

According to an aspect of the invention, there is shown in FIG. 40 a side view of an example embodiment 688 of the leading section 154 of the guide element 120 having retaining structures 690 constructed thereon. In this example embodiment 688, the retaining structures 690 are formed as a plurality of small spaced indentations in the leading section 154 near the end 648 thereof. The retaining structures 690 may be ring-like indentations extending around the entire circumference of the leading section 154, but could also extend less than the entire circumference or could take the form of dimples. The retaining structures 690 may be regularly or irregularly spaced. Any appropriate swallowable weight (not shown) may be used with the retaining structures 690, and the weight preferably surrounds the retaining structures, at least until the weight arrives in the patient's stomach The retaining structures 678, 682, 686, 690 may also be formed in other appropriate shapes. The retaining structures 678, 682, 686, 690 may be formed integrally with the guide element leading section 154, for example by molding, or may be applied to leading section 154 after its formation. The retaining structures 678, 682, 686, 690 may be constructed of any appropriate material, and are preferably flexible and adapted to minimize any abrasion or injury to the patient during insertion, removal, or swallowing of the guide element. The retaining structures are preferably sized to permit removal of the guide element through either the nasogastric tube (if the guide element is threaded through a lumen thereof as depicted in FIGS. 30-32), or the guide element retaining structure 136 (if the guide element is threaded through such a structure as depicted in FIG. 1).

Figure 41:
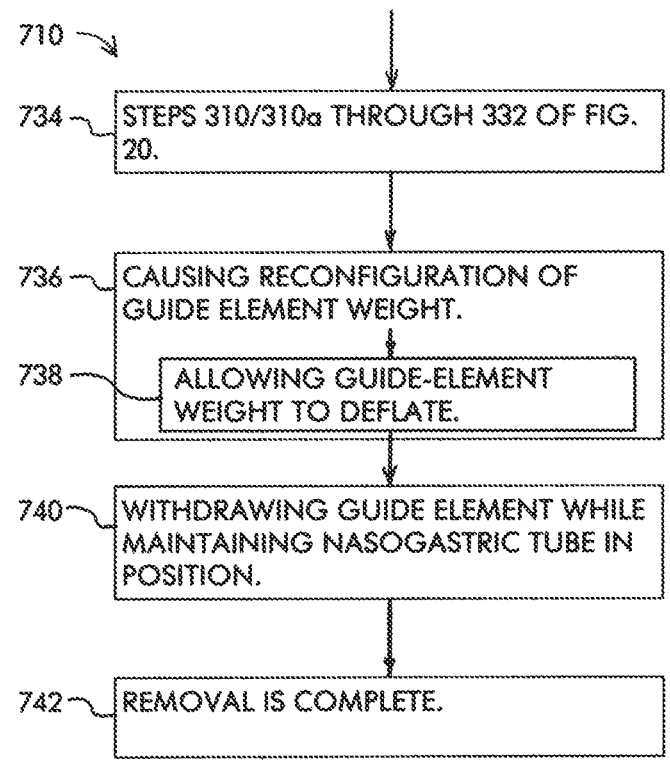
FIG. 41 is a flow diagram showing an example method according to an aspect of the invention for reconfiguring the shape of a guide element, such as that shown in FIGS. 30-32, and removing the guide element while the nasogastric tube remains in place.

According to a further aspect of the invention, there is shown in FIG. 41 a flow diagram of a method 710 for use in removing a guide element of the type shown in FIGS. 30-32 when used in conjunction with a nasogastric tube of the type shown in FIGS. 30-32. Step 734 incorporates steps 310 or 310a through step 332 of FIG. 20, at the end of which, the guide element, including the swallowable weight thereof, in its inflated condition, has been positioned in the patient's stomach, and the nasogastric tube has been inserted into the patient's stomach using the guide element. The swallowable weight may be inflated as part of the manufacturing process or may be inflated by the user in preparation for its introduction into the patient.

In step 736, the user causes reconfiguration of the swallowable weight to enable its withdrawal from the patient while the nasogastric tube remains in position. The implementation of step 736 may be further defined by optional substep 738, in which the user allows the guide element to deflate. The user may accomplish this by allowing fluid to exit the lumen 626 of the guide element, or by actively withdrawing fluid through the lumen.

Figure 42:
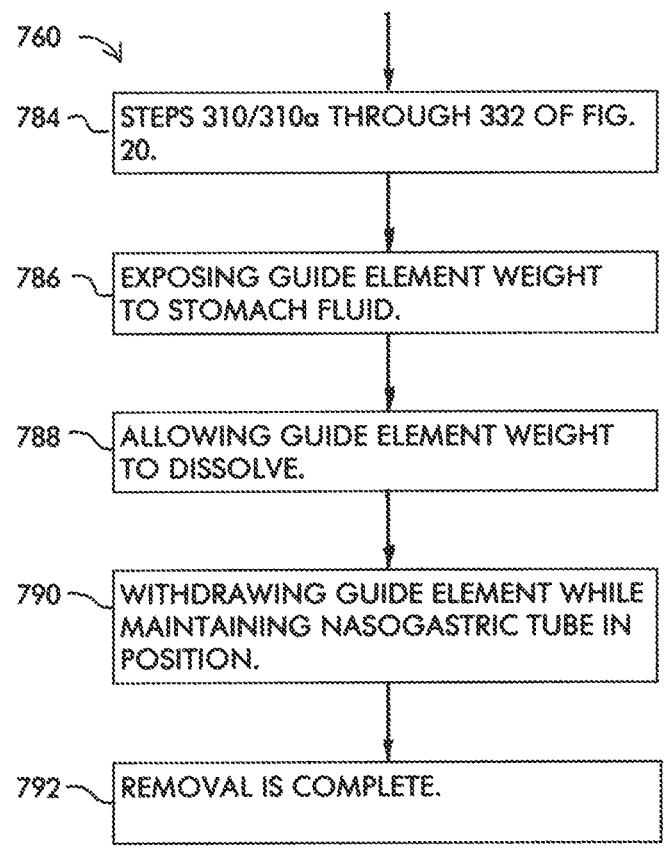
FIG. 42 is a flow diagram showing an example method according to an aspect of the invention for reconfiguring the shape of a guide element, such as that shown in FIGS. 33-40, and removing the guide element while the nasogastric tube remains in place.

In step 740, the user withdraws the guide element from the patient while maintaining the nasogastric tube in position. In step 742, removal of the guide element is complete. According to a further aspect of the invention, there is shown in FIG. 42 a flow diagram of a method 760 for use in removing a guide element of the type shown in FIGS. 33-36, when used in conjunction with a nasogastric tube of the type shown in FIG. 1 or FIGS. 30-32. Step 784 incorporates steps 310 or 310a through step 332 of FIG. 20, at the end of which, the guide element, including the swallowable weight thereof, has been positioned in the patient's stomach, and the nasogastric tube has been inserted into the patient's stomach using the guide element.

In step 786, the guide element weight is exposed to stomach fluid. In step 788, the guide element weight is allowed to dissolve, disintegrate, soften, melt, or the like, enabling the guide element leading section 154 to be withdrawn without disturbing the position of the nasogastric tube. In step 790, the user withdraws guide element from the patient while the nasogastric tube is retained in position. In step 792, removal of the guide element is complete.

According to a further aspect of the invention, the nasogastric tube or the guide element may incorporate a chemical-property indicating medium to facilitate verification that the nasogastric tube has been inserted properly into the patient's stomach, and has not been inserted into the lung or other undesirable location. The fluids present in a patient's stomach have an acidic pH below 5.0, while fluids present in locations into which it is possible to erroneously insert the nasogastric tube generally have pH above 5.0. By exposing the indicating medium to the fluids surrounding the distal end of the nasogastric tube, the indicating medium enables the user to verify that the pH of those fluids is below 5.0, thus confirming correct insertion of the nasogastric tube. If the indicating medium is incorporated in the nasogastric tube, the fluids surrounding the distal end of the tube may be aspirated through the tube and into contact with the medium, the condition of which may then be observed by the user. If the indicating medium is incorporated in the guide element, the fluids surrounding the distal end of the tube will come in contact with the medium without additional overt action by the user, although the guide element must subsequently be withdrawn from the patient so that the condition of the medium may be observed. The indicator may generally be used to obtain a measurement of the gastric pH. This measurement may be employed for purposes in addition to establishing correct insertion of the nasogastric tube, including determination that the stomach is prepared to receive a therapeutic agent, or that an appropriate quantity of a therapeutic agent affecting pH, has been introduced. As an alternative to a pH-sensitive medium, media indicating chemical properties other than pH, which may verify correct insertion of the nasogastric tube, signal incorrect insertion of the nasogastric tube, or verify correct or sufficient introduction of a therapeutic, buffering, or irrigation agent, could also be used.

According to an aspect of the invention, there is shown in FIG. 43 a side view of an example embodiment 810 of a nasogastric tube in which a chemical-property indicating medium is incorporated near the proximal end section 114 thereof. FIG. 44 is a cross section view of the example embodiment 810 taken along section lines 44-44 of FIG. 43. The example embodiment 810 may be generally constructed in a manner similar to the nasogastric tube 110 of FIG. 1, with modifications described in this section.

As best seen in FIGS. 43-44, nasogastric tube 810 preferably comprises a generally tubular proximal end section 114 having an interior wall 814 forming at least one lumen 146. If plural lumina are provided in tube 810, the lumen 146 is preferably the one adapted for use in aspirating fluid near the distal end of the tube. The nasogastric tube 810 preferably includes a section 812 for housing a chemical property indicating medium 820. Section 812 may be enlarged, compared to the diameter of other sections of the nasogastric tube. A channel 822 is preferably provided in which the chemical property indicating medium 820 is captured. Several openings 816 are preferably provided between the main bore of lumen 146 and the channel 822 to allow communication of fluid between the lumen 146 and the channel 822. The openings 816, channel 822, and medium 820 are preferably adapted such that when fluid is present in lumen 146, it inundates channel 822 and exposes medium 820.

Medium 820 preferably furnishes a visual indication of a chemical property, such as pH, which may, for example, be manifested as a change in color, reflectivity, or the like. Section 812 is preferably clear or translucent to allow the medium 820 to be viewed externally. The shape of section 812 may act as a magnifying lens to allow a small medium to be easily viewed. Any appropriate chemical-property indicating medium, including but not limited to litmus, pH indicating strips, paper, cloth, or any other substrate impregnated with or bearing a pH indicator, or the like, may be used to implement medium 820. The position and size of section 812 is preferably selected such that the condition of the indicator strip is visually apparent when fluids are initially aspirated through lumen 146 so that the user need not take any additional steps in order to confirm correct insertion of the nasogastric tube in the patient's stomach.

According to a further aspect of the invention, there is shown in FIG. 45 a side view of an additional example embodiment 830 of a nasogastric tube in which a chemical-property indicating medium is incorporated near the proximal end section 114 thereof. There is shown in FIG. 46 a side view of an additional example embodiment 840 of a nasogastric tube in which a chemical-property indicating medium is incorporated near the proximal end section 114 thereof. FIG. 47 is a cross section view of the embodiment 830 taken along the section lines 47-47 thereof. FIG. 48 is a cross section view of the embodiment 840 taken along the section lines 48-48 thereof. The example embodiments 830 and 840 may be generally constructed in a manner similar to the nasogastric tube 110 of FIG. 1, with modifications described in this section.

As best seen in FIGS. 45-48, each of nasogastric tubes 830 and 840 preferably comprises a generally tubular proximal end section 114 having an interior wall 814 forming at least one lumen 146. If plural lumina are provided in tube 830 or 840, the lumen 146 is preferably the one adapted for use in aspirating fluid near the distal end of the tube. Nasogastric tube 830 comprises a chemical-property indicating medium applied to the interior wall 814 in the form of a plurality of indicating elements 832 spaced circumferentially along the interior wall 814. Nasogastric tube 840 comprises a chemical-property indicating medium applied to the interior wall 814 in the form of an indicating element 842 that covers the circumference of the interior wall 814. These particular configurations of the indicating elements 832 and 842 are examples. Other configurations could also be used.

The indicating elements 832 and 842 may be formed using any suitable chemical-property indicating medium or substance, including but not limited to a coating, litmus, pH-indicating strips, paper, cloth, or the like. For example, the medium may be formed as a coating or gelatin bearing phenolphthalein. The term medium is also intended to refer to any indicating substance, regardless of whether or not the indicating chemical or component is carried in or on a substrate, matrix, or similar carrier. Other indicating media could also be used. If the medium is integrated with a substrate such as a paper strip, such substrate is preferably applied to the interior wall 814 using an appropriate adhesive or fastening technology, which may include infrared or ultrasonic bonding. The positions and sizes of the indicating elements 832 and 842 are preferably selected such that the condition of the indicating elements is visually apparent when fluids are initially aspirated through lumen 146, so that the user need not take any additional steps in order to confirm correct insertion of the nasogastric tube in the patient's stomach. In some applications, aspirated fluid that contacts the indicating medium may be reintroduced into the patient or may otherwise come in contact with the patient.

Also, the indicating medium must be firmly attached or adherent to the interior wall 814, or particles or fragments of the indicating medium itself may be inadvertently introduced into the patient through the nasogastric tube or may otherwise contact the patient. In such applications, an indicating medium is preferably selected for bio-compatibility to avoid any potentially toxic effects.

Figure 49:
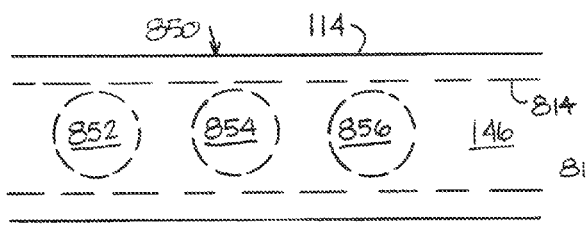
FIG. 49 is a side view of the further alternate embodiment of a nasogastric tube, showing a chemical-property indicating medium thereof in a third example configuration.

According to a further aspect of the invention, there is shown in FIG. 49 a side view of an additional example embodiment 850 of a nasogastric tube in which a chemical-property indicating medium is incorporated near the proximal end section 114 thereof.

As best seen in FIG. 49, a plurality of distinct indicating elements, such as 852, 854, and 856 are provided, each having a medium for visually and distinctly indicating a different chemical property or a different value of a chemical property. The indicating elements 852, 854, and 856 may, for example, change appearance to indicate different pH thresholds have been sensed, or may change appearance to indicate the presence or absence of specific chemicals, proteins, or other detectable components in the fluid aspirated from the vicinity of the distal end of the nasogastric tube. This would give a measurement of gastric pH, as well as verify proper placement of the nasogastric tube. The activated appearance of each of the indicating elements 852, 854, 856 may be visually distinctive. For example, they may appear as distinguishably different colors, thereby minimizing ambiguity as to which indicators are activated. Although the indicating elements are shown in the shape of dots, any suitable shape could also be used, and the elements may be provided in any practical size and number. Any suitable indicating media could be used to implement the indicating elements 852, 854, and 856, such as those described in connection with the embodiments 830 and 840 of FIGS. 45-46.

Figure 50:
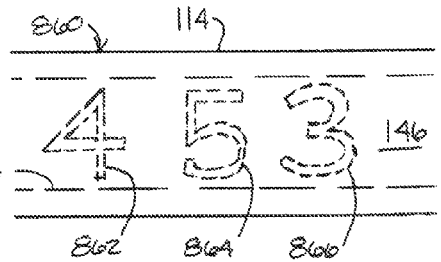
FIG. 50 is a side view of the further alternate embodiment of a nasogastric tube, showing a chemical-property indicating medium thereof in a fourth example configuration.

According to a further aspect of the invention, there is shown in FIG. 50 a side view of an additional example embodiment 860 of a nasogastric tube in which a chemical-property indicating medium is incorporated near the proximal end section 114 thereof. As best seen in FIG. 50, a plurality of distinct indicating elements, such as 862, 864, and 866 are provided, each having a medium for visually and distinctly indicating a different chemical property or a different value of a chemical property, and each having a different shape, size, or other characteristic so that there is no ambiguity as to which indicators are activated. The indicating elements 862, 864, and 866 may, for example, change appearance to indicate different pH thresholds have been sensed, or may change appearance to indicate the presence or absence of specific chemicals, proteins, or other detectable components in the fluid aspirated from the vicinity of the distal end of the nasogastric tube. The shape, size, or other characteristics of the indicating elements may be selected to correspond to the property indicated. By way of example but not limitation, the indicating elements 862, 864, and 866 may be designed to change appearance when fluid pH crosses specific pH thresholds of 4.0, 5.0, and 3.0, respectively, and the indicating elements may be formed as recognizable characters, symbols, or glyphs corresponding to these thresholds. Other distinctive shapes and forms and other schemes defining correspondence between the visual distinctiveness of the indicating element and the property being sensed could also be used. The activated appearance of each of the indicating elements 862, 864, 866 may be visually distinctive in ways in addition to their shape, for example, they may appear as distinguishably different colors, to further minimize ambiguity as to which indicators are activated. Any suitable indicating media could be used to implement the indicating elements 862, 864, and 866, such as those described in connection with the embodiments 830 and 840 of FIGS. 45-46.

Figure 51:
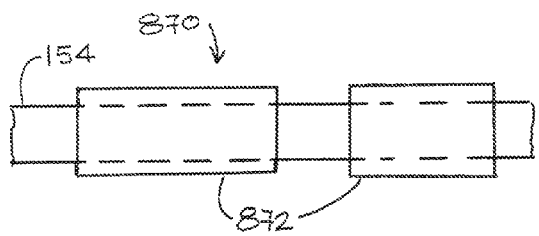
FIG. 51 is a side view of the leading section of a further alternate embodiment of a guide element, showing a chemical-property indicating medium thereof in a first example configuration.

According to a further aspect of the invention, there is shown in FIG. 51 a side view of an additional example embodiment 870 of a guide element with which a chemical-property indicating medium is incorporated on or near the leading section 154 thereof. Guide element 870 may generally be constructed as heretofore shown and described in connection with guide element 120 (FIG. 1), 610 (FIG. 30) or 630 (FIG. 33), with modifications as described in this section. As best seen in FIG. 51, one or more indicating elements 872 are provided on the outer surface of the leading section 154 of the guide element, each having a medium for visually indicating a chemical property. The indicating elements 872 are exposed to fluids in the vicinity of the end of the leading section 154. When the guide element is withdrawn from the patient, the indicating elements are visually apparent and can be used to confirm that the guide element and nasogastric tube were properly inserted in the patient's stomach. Different, visually distinctive indicating elements may be used to indicate different chemical properties or values thereof, as described more fully in connection with embodiment 850 of FIG. 49. Any suitable indicating media could be used to implement the indicating elements 872, such as those described in connection with the embodiments 830 and 840 of FIGS. 45-46.

Figure 52:
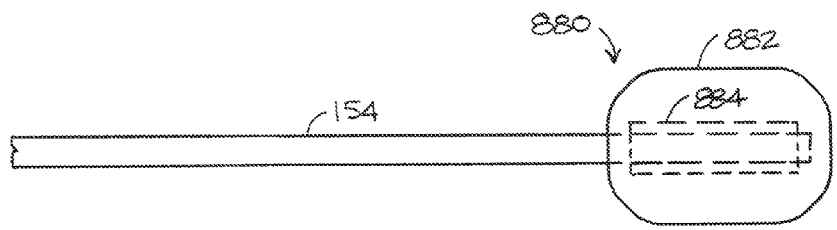
FIG. 52 is a side view of the leading section of a further alternate embodiment of a guide element, showing a chemical-property indicating medium thereof in a second example configuration.

According to a further aspect of the invention, there is shown in FIG. 52 a side view of an additional example embodiment 880 of a guide element with which a chemical-property indicating medium is incorporated on or near the leading section 154 thereof. Guide element 880 may generally be constructed as heretofore shown and described in connection with guide element 120 (FIG. 1), 610 (FIG. 30) or 630 (FIG. 33), with modifications as described in this section. As best seen in FIG. 52, one or more indicating elements 884 are provided on the outer surface of the leading section 154 of the guide element near the end thereof, each having a medium for visually indicating a chemical property. A swallowable weight 882 surrounds the indicating elements 884. Swallowable weight 882 is preferably constructed from a material that is soluble in stomach fluids, or disintegrates or becomes extremely soft when exposed to stomach fluids, or changes from a solid to liquid state when exposed to stomach fluids or to the temperature present in the body, as more fully explained in connection with the embodiment 630 of FIG. 33. After exposure to stomach fluids (or other fluids in the vicinity of the weight 882, the weight 882 dissolves, melts, ablates, or disintegrates, thereby exposing the indicating elements 884. When the guide element is withdrawn from the patient, the indicating elements are visually apparent and can be used to confirm that the guide element and nasogastric tube were properly inserted in the patient's stomach. Different, visually distinctive indicating elements may be used to indicate different chemical properties or values thereof, as described more fully in connection with embodiment 850 of FIG. 49. Any suitable indicating media could be used to implement the indicating elements 872, such as those described in connection with the embodiments 830 and 840 of FIGS. 45-46.

Figure 53:
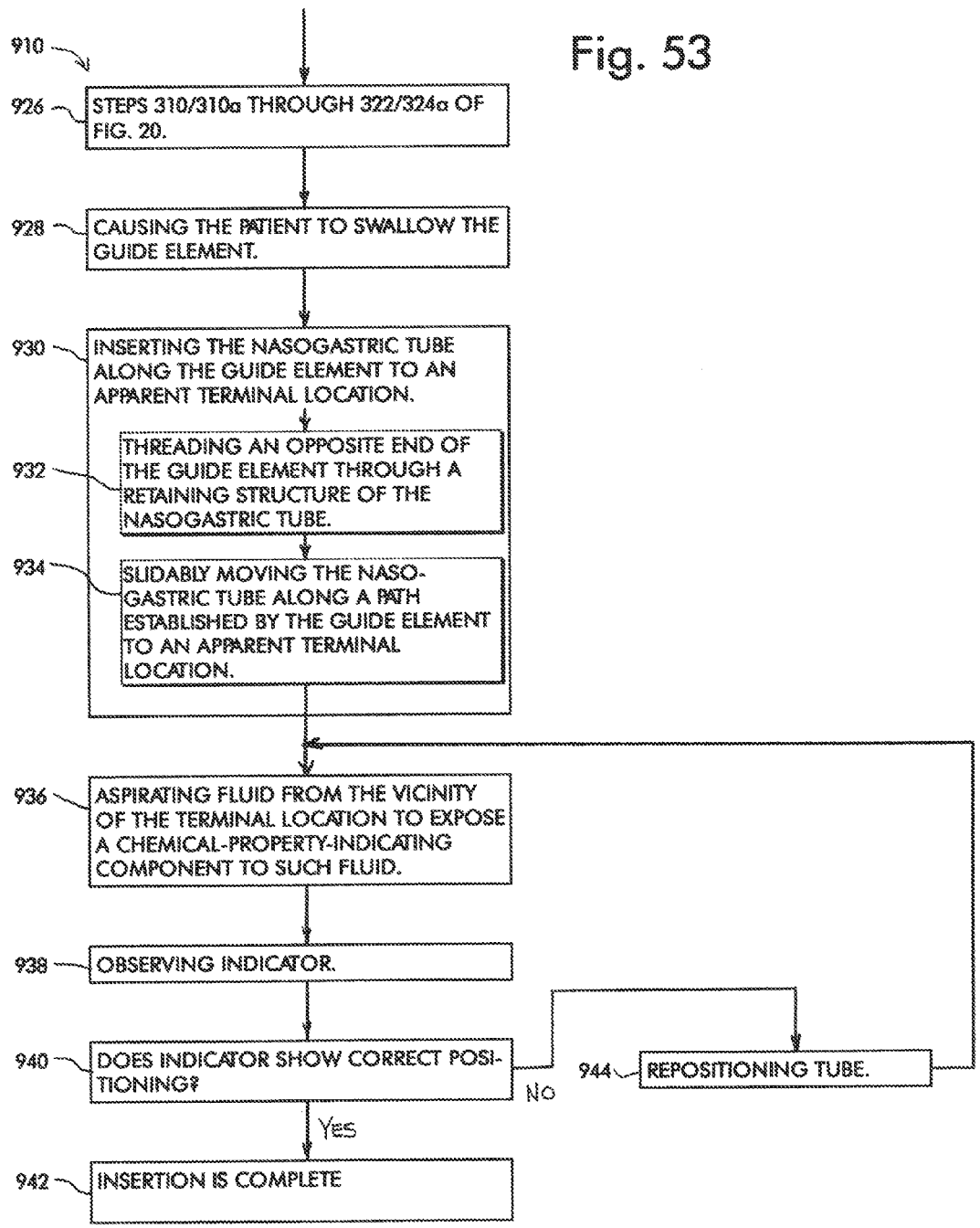
FIG. 53 is a flow diagram showing an example method according to an aspect of the invention for determining correct insertion of a nasogastric tube by exposing a chemical property indicator such as those shown in FIGS. 43-50.

According to a further aspect of the invention, there is shown in FIG. 53 a flow diagram of a method 910 for use in positioning a nasogastric tube of the types shown and described in connection with FIGS. 43-50. Step 926 incorporates steps 310 or 310a through step 322 or 234a of FIG. 20, at the end of which, the guide element has been inserted through the nostrils and is ready to be swallowed by the patient.

In step 928, the guide element is swallowed by the patient. In step 930, the nasogastric tube is inserted along the guide element to an apparent terminal location. The apparent terminal location may be in the patient's stomach, as desired, or may be in some other undesired location, such as the lung. The implementation of step 930 may be further defined by optional substeps 932 and 934. In substep 932, inserting the nasogastric tube along the guide element is partially implemented by threading an opposite end of the guide element through a retaining structure of the nasogastric tube. In substep 934, inserting the nasogastric tube along the guide element is partially implemented by slidably moving the nasogastric tube along a path established by the guide element to an apparent terminal location.

In step 936, fluid from the vicinity of the terminal location is aspirated to expose a chemical-property indicating component to the fluid. In step 938, the user observes the indicator. In step 940, the user determines whether the indicator shows correct placement of the nasogastric tube. If the placement is determined to be correct, the method ends at step 942. If the placement is determined to be incorrect, the method continues in step 944, in which the user repositions the tube. The method then returns to step 936 and steps following.

Figure 54:
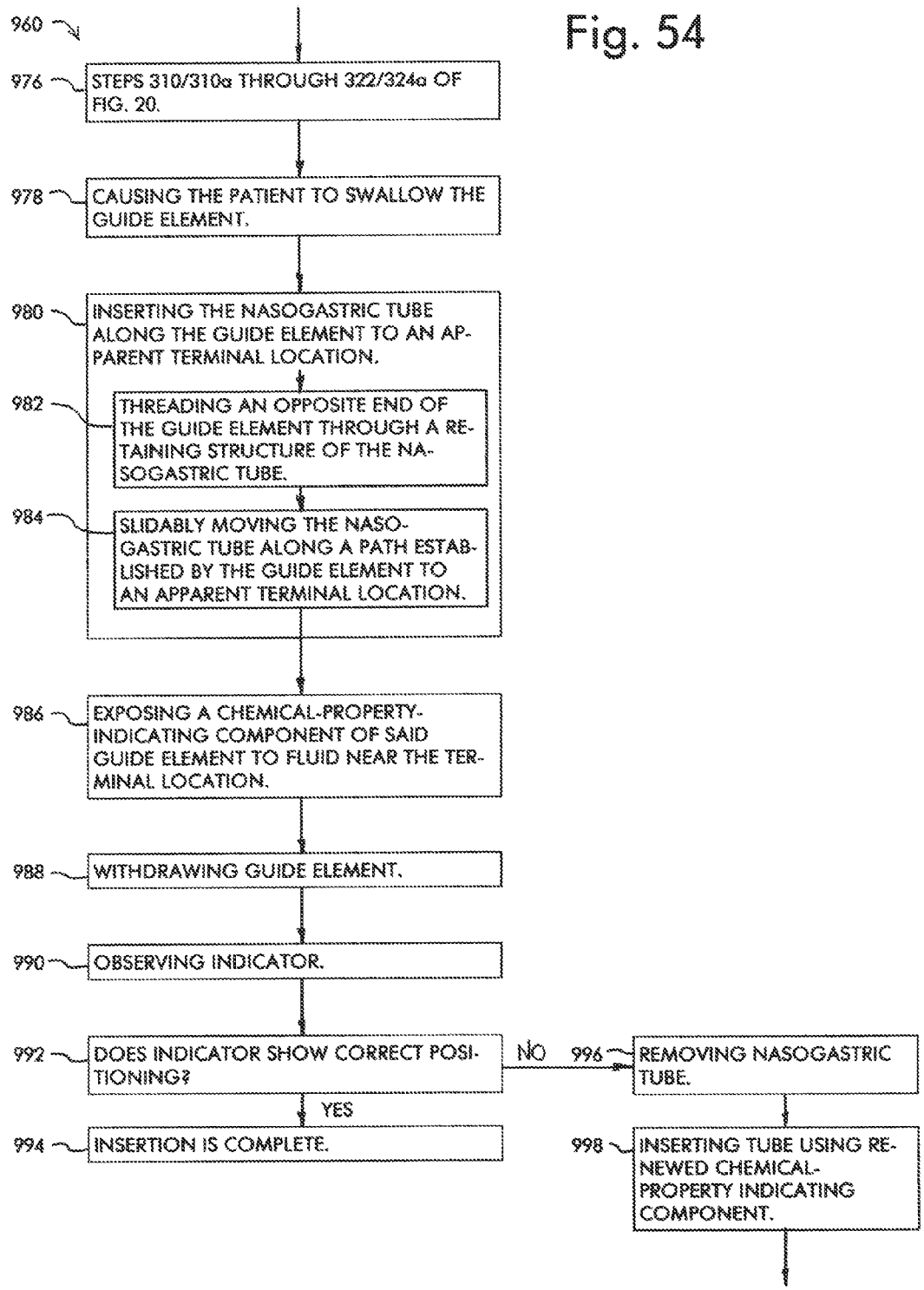
FIG. 54 is a flow diagram showing an example method according to an aspect of the invention for determining correct insertion of a nasogastric tube by exposing a chemical property indicator such as those shown in FIGS. 51-52.

According to a further aspect of the invention, there is shown in FIG. 54 a flow diagram of a method 960 for use in positioning a nasogastric tube in conjunction with a guide element of the types shown and described in connection with FIGS. 51-52. Step 926 incorporates steps 310 or 310a through step 322 or 234a of FIG. 20, at the end of which, the guide element has been inserted through the nostrils and is ready to be swallowed by the patient.

In step 978, the guide element is swallowed by the patient. In step 980, the nasogastric tube is inserted along the guide element to an apparent terminal location. The apparent terminal location may be in the patient's stomach, as desired, or may be in some other undesired location, such as the lung. The implementation of step 980 may be further defined by optional substeps 982 and 984. In substep 982, inserting the nasogastric tube along the guide element is partially implemented by threading an opposite end of the guide element through a retaining structure of the nasogastric tube. In substep 984, inserting the nasogastric tube along the guide element is partially implemented by slidably moving the nasogastric tube along a path established by the guide element to an apparent terminal location.

In step 986, a chemical-property indicating component of the guide element is exposed to fluid present near the terminal location. In step 988, the guide element is withdrawn, while the nasogastric tube remains in place. Removal of the guide element allows the indicating component to be viewed by a user.

In step 990, the user observes the indicator. In step 992, the user determines whether the indicator shows correct placement of the nasogastric tube. If the placement is determined to be correct, the method ends at step 994. If the placement is determined to be incorrect, the method continues in step 996, in which the nasogastric tube is removed. Then in step 998, the nasogastric tube is inserted again, using a guide element. Because the chemical-property indicating component will already have been exposed to fluids, it may be necessary to use a new guide element, or to renew the indicator on the previously-used guide element. Step 998 may incorporate steps 978 through 984, and the method may continue in step 986.

Figure 55:
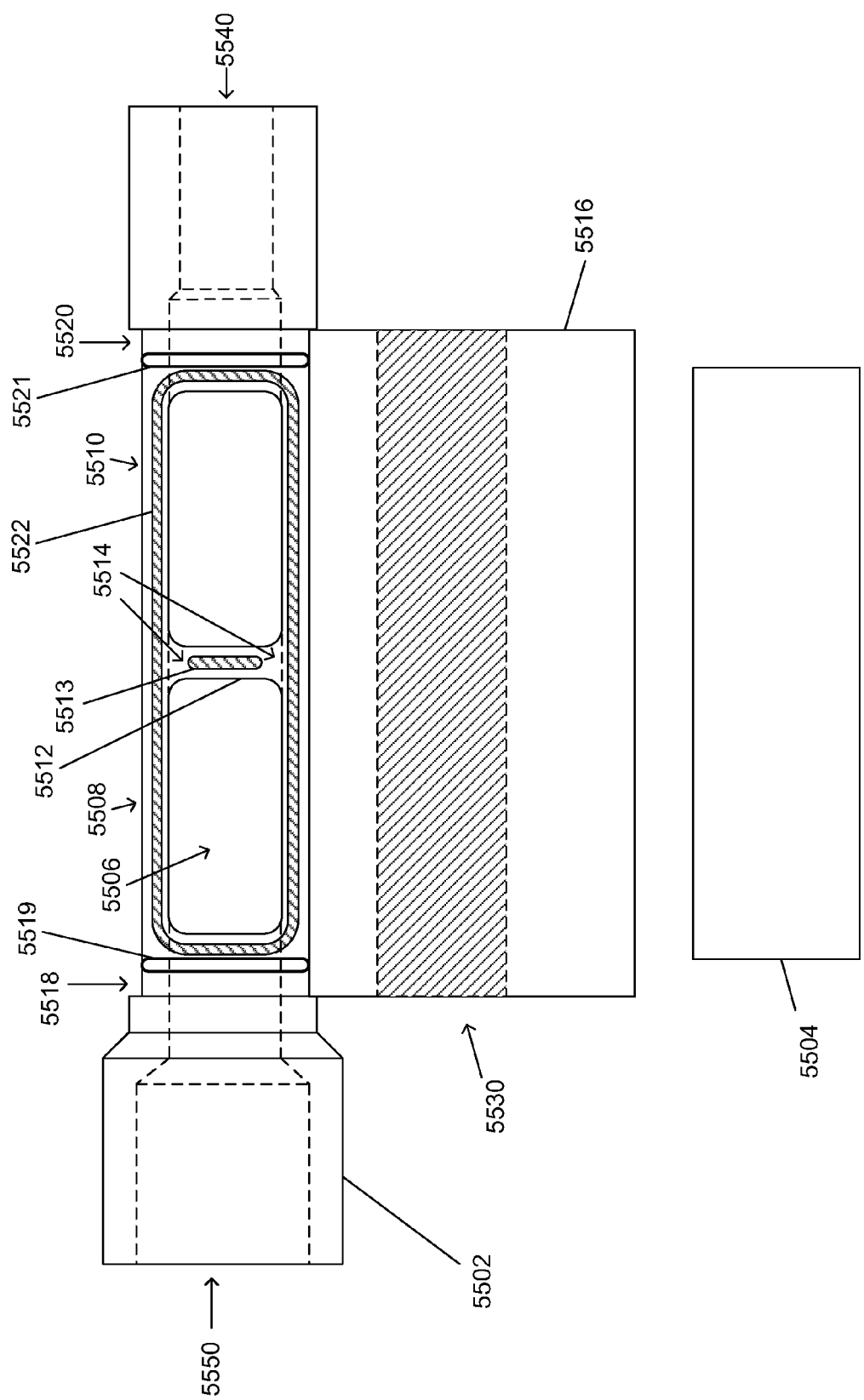
FIG. 55 is a top view of one implementation of a housing for a detection indicator.

Turning to FIGS. 55-56, an apparatus 5500 in one example comprises a housing 5502 and a detection indicator 5504. The detection indicator 5504 in one example is analogous to the chemical-property indicating medium or indicating elements described above. For example, the detection indicator is configured to change from a first visual indication to a second visual indication upon contact with a fluid or fluid sample based on a characteristic of the fluid. However, in the embodiment shown in FIGS. 55-56, the detection indicator 5504 is engaged or coupled with the housing 5502, which is separate from the nasogastric tube, the guide element, and the inserter element. The housing 5502 is configured to removably engage the proximal end of a lumen or tube inserted into the patient's body, such as the nasogastric tube. Accordingly, the apparatus 5500 provides a removable housing 5502 with the detection indicator 5504.

The housing 5502 comprises an interior chamber 5506 such as a channel, lumen, or reservoir that is configured to receive the fluid. The interior chamber 5506 provides sufficient contact between the fluid and the detection indicator 5504 to cause the visual change of the detection indicator 5504. In a first implementation, the detection indicator 5504 is located inside the interior chamber 5506. The detection indicator 5504 may be secured in place by adhering it to a surface in the interior chamber 5506, by a friction fit, or by placing the detection indicator 5504 in a matrix that is adherent to the surface in the interior chamber 5506. The surface may be an interior surface of the interior chamber 5506 or a face of a protrusion specifically designed to support the detection indicator 5504 within the interior chamber 5506. In another example, the interior chamber 5506 comprises a slot or engagement component configured to receive and/or secure the detection indicator 5504. The housing 5502 in one example is configured to removably secure the detection indicator 5504 to allow replacement of the detection indicator 5504, as will be appreciated by those skilled in the art.

In a second implementation, the detection indicator 5504 is located adjacent to and/or in fluid communication with the interior chamber 5506. For example, the housing 5502 may comprise at least one detection opening to the interior chamber 5506. The housing 5502 may comprise a fenestrated wall to provide the detection openings. Referring to FIG. 55, the housing 5502 comprises detection openings 5508 and 5510. In this implementation, the detection openings 5508 and 5510 are adjacent and partially separated by a support post 5512, which may provide structural integrity to the housing 5502. The support post 5512 in one example is configured with a raised rib 5513 to form at least one channel 5514 adjacent to the raised rib 5513. The channel 5514 provides a path for fluid communication between the detection openings 5508 and 5510. The channel 5514 promotes a flow of the fluid between the detection openings to provide a more thorough saturation of the detection indicator 5504 by the fluid and accordingly, a more complete or easily recognizable visual change in the detection indicator 5504, as will be appreciated by those skilled in the art.

The detection indicator 5504 is configured to abut the detection opening to provide the contact between the fluid and the detection indicator 5504. In one example, the detection indicator 5504 is configured to provide a seal against the detection opening to prevent leakage of the fluid to an exterior of the housing 5502. In another example, the housing 5502 comprises a sealing member 5516 configured to secure the detection indicator 5504 to the detection opening to provide the seal. The sealing member may be formed integrally with the housing 5502 or as a separate component that is secured and/or bonded to the housing 5502, such as by plastic welding, heat sealing, and/or with an adhesive. Examples of the adhesive include silicone based RTV adhesives such as Nusil MED3-4013 (Nusil Technology LLC; Carpinteria, Calif.). The housing 5502 may comprise one or more channels 5518 and 5520, adjacent to the detection openings, configured to receive the adhesive, epoxy, or other sealing components 5524 to secure the sealing member to the housing 5502. The channels 5518 and 5520 may extend partially or completely around the detection openings 5508 and 5510. The channels 5518 and 5520 in one example are formed by raised ribs 5519 and 5521, respectively. In alternate implementations, the sealing member 5516 and the housing 5502 may be configured with interlocking slots and tabs to provide the seal.

In one implementation, the sealing member 5516 comprises a flap configured to cover the detection indicator 5504 by wrapping over the detection indicator 5504 and around the housing 5502. In a further implementation, the detection indicator 5504 is coupled with the sealing member 5516.

The housing 5502 in one example comprises one or more raised ribs 5522 that surround the detection openings 5508 and 5510. The raised ribs 5522 and 5513 provide a raised point of contact which increases engagement pressure between the detection indicator 5504 and the sealing member 5516 for sealing the interior chamber 5506 from leaks, as will be appreciated by those skilled in the art. In alternative implementations, one or more of the raised ribs 5513 and 5522 may be formed on the sealing member 5516.

Referring to FIGS. 56A and 56B, in one implementation the detection indicator 5504 is placed over the detection openings 5508 and 5510. The detection indicator 5504 abuts the raised ribs 5513 and 5522. In one example, the detection indicator 5504 is sized to fit between the raised ribs 5519 and 5521 to aid positioning of the detection indicator 5504 on the housing 5502.

In one implementation, the housing 5502 comprises a tubular structure with a first opening 5540 configured to removably engage with the proximal end of the lumen. An adapter 5700 (FIG. 57) may be used between the housing 5502 and the lumen to ensure a sealed connection, as described herein. Advantageously, this implementation reduces a risk of contamination of the fluid sample and also exposure of the practitioner to bodily fluids. Additionally, results of the determination are readily available, typically within minutes and conveniently at the patient's bedside, which significantly reduces the typical time required to send a fluid sample to a lab for analysis. Examples of a housing 5502 for this implementation include a test tube 6200 (FIG. 62), vial, "vacutainer" 6300 (FIG. 63) or other evacuated chamber, or a needle/syringe 6100 (FIG. 61). The size of the first opening 5540 may be selected according to the lumen, tube, or adapter that the housing 5502 is intended to engage. Accordingly, various sizes of the housing 5502 are contemplated for nasogastric tubes, feeding tubes, catheters, and other variations such as those appropriate for adult or infant-sized tubes. The housing 5502 and/or adapter 5700 in one example includes a Y-fitting, T-fitting, or other juncture.

In a further implementation, the housing 5502 comprises a second opening 5550 configured to removably engage with a fluid retrieval component 5802 (e.g., a syringe, suction pump, wall suction or vacuum system) for retrieving the fluid from a distal end of the lumen into the interior chamber 5506. Another adapter, tube, and/or coupling element may be used between the housing 5502 and the fluid retrieval component. As with the first opening 5540, the size of the second opening 5550 may be selected according to the lumen, fluid retrieval component, or adapter size. The housing 5502 and/or adapters may be formed or molded from plastic, glass, or other medical-grade materials. The housing 5502 and/or adapters in one example are configured to be disposable and are formed from relatively inexpensive materials, as will be appreciated by those skilled in the art.

The detection indicator 5504 is configured to provide a visual indication of a characteristic of a fluid, upon contact with the fluid. In one example, the detection indicator 5504 is configured to change from a first visual indication to a second visual indication upon contact with the fluid based on a characteristic of the fluid (such as the pH). The first and second visual indications may be different colors, patterns, or other indicators. In another example, the first and second visual indications are within a range of possible colors. For example, a detection indicator 5504 may gradually change from red, to orange, to yellow or from yellow to brown to blue as an indication of different levels of pH, as will be appreciated by those skilled in the art.

The visual indication in another example comprises one or more dots or symbols that change color based on different pH readings. In another example, individual letters, numbers or symbols may change color or appearance (e.g., from low visibility to high visibility) to allow the practitioner to read or approximate the pH. As described above, the detection indicator 5504 may be any appropriate chemical-property indicating medium, including but not limited to litmus, pH indicating strips, paper, cloth, or any other substrate impregnated with or bearing a pH indicator, or the like. Other examples include nitrazine paper, pHydrion, Hydrion, and pHizatest paper (Micro Essential Laboratory, Inc.; Brooklyn, N.Y.).

The apparatus 5500 in a further example comprises one or more reference indicators 5530 configured to provide a reference visual indication for visual comparison with the detection indicator 5504. In one example, the reference indicator 5530 is coupled with the housing 5502. The reference indicator 5530 and/or the detection indicator 5504 in one example are configured and/or located such that the reference indicator 5530 and the detection indicator 5504 are simultaneously viewable from at least one viewpoint by the practitioner. For example, both the reference indicator 5530 and detection indicator 5504 are viewable by the practitioner without undue effort by the practitioner. In a first example, the detection indicator 5504 and reference indicator 5530 are located adjacent to each other. In another example, the detection indicator 5504 is located inside the housing 5502 and the reference indicator 5530 is located outside of the housing 5502. In this example, the detection indicator is visible through at least a portion of the housing 5502 (e.g., through a window, viewport, or with a clear/transparent housing) such that the detection indicator and reference indicator 5530 can be viewed simultaneously. An optically clear adhesive may be used to facilitate viewing of the detection indicator through the housing 5502.

In one example, the detection indicator, the reference indicator 5530, and the housing 5502 are configured such that the detection indicator and the reference indicator 5530 are viewable from multiple angles or positions. Accordingly, the detection indicator and reference indicator 5530 are viewable by the practitioner without a need to rotate the housing 5502 to a required viewing angle. The detection indicator and the reference indicator 5530 may be configured in a "wraparound" arrangement or wrapped around a portion of the perimeter of the housing 5502, such as half of the perimeter. In another example, the detection indicator and the reference indicator 5530 are wrapped or positioned around the entire perimeter of the housing 5502 to facilitate viewing from any angle or rotation of the housing 5502. For example, the reference indicator 5530 may be coupled with the sealing member or flap prior to wrapping the sealing member around the housing 5502. In alternative implementations, multiple detection indicators and reference indicators may be used with the housing 5502.

Figure 57:
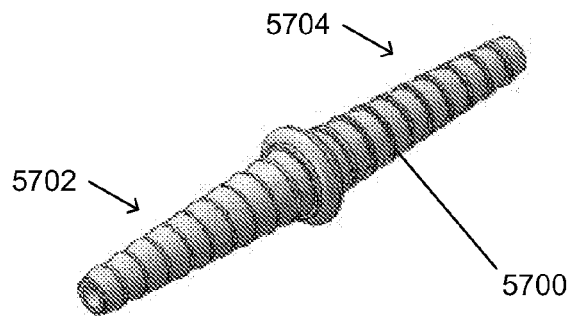
FIG. 57 is a perspective view of one implementation of an adapter configured for use with the housing of FIG. 55.

The adapters 5700 in one example comprise any of a barb fittings, cone-shaped fittings, fluid connectors, couplers, or the like. The adapter may be configured with multiple ribs or engagement surfaces of different diameters to facilitate engagement with a variety of tube or device sizes and shapes. Turning to FIG. 57, the adapter 5700 in one example may have barb fittings 5702 and 5704 on opposing ends. The adapter may be a separate component or integral with the housing 5502 and/or fluid retrieval component. Where two adapters are used for the first and second openings, the adapters may be identical or different. The adapters are configured to securely engage via a compression fit, interference fit, friction fit, or screw-type engagement.

In one implementation, one or more of the housing 5502, fluid retrieval device, adapters, and reference indicator 5530 are provided together in a kit. For example, a pre-packaged container may include the fluid retrieval device, two adapters, and a plurality of housings 5502 so that multiple readings can be taken with the contents of one kit. Advantageously, the contents of the kit can be sterilized prior to shipping to a hospital or clinic and provide a practitioner with necessary components for analysis of patient fluids. Other combinations of elements within the kit are possible and additional contents of the kit may be provided to facilitate use of the apparatus, such as extra tubing and/or adapters for coupling to a wall suction or vacuum system.

Figure 58:
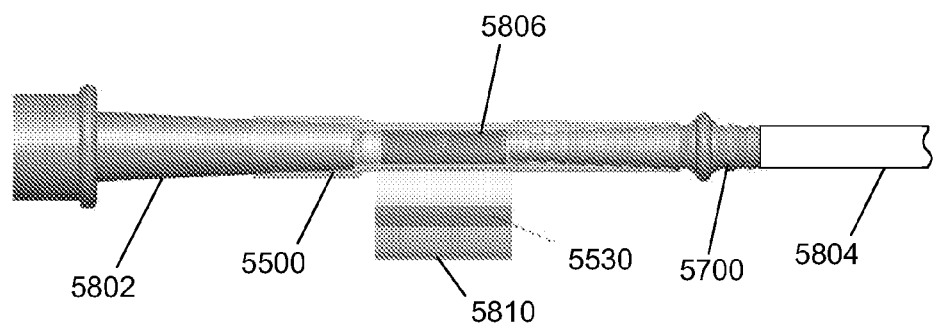
FIGS. 58 and 59 are top and side views of the housing of FIG. 55 engaged with a lumen at a first opening with the adapter of FIG. 57 and also engaged with a fluid retrieval component at a second opening.
Figure 59:
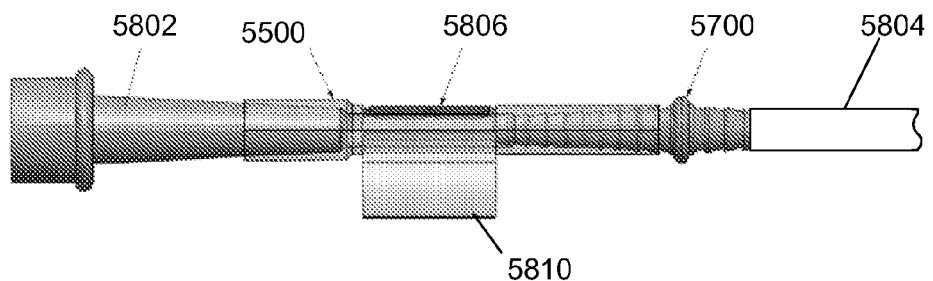

Turning to FIGS. 58 and 59, the apparatus 5500 is shown in one implementation engaged with the fluid retrieval component 5802 and engaged with a lumen 5804 via the adapter 5700. The detection indicator 5806 in this example comprises a strip of litmus paper that is placed over the detection openings 5508 and 5510 and secured in place by the flap 5810. The reference indicator 5530 is shown coupled with the flap 5810 such that when the flap 5810 is wrapped, closed, and/or sealed around the housing 5502, the reference indicator 5530 is near or adjacent to the detection indicator 5806. In other examples, the adapter 5700 or the housing 5502 may be coupled with a suction lumen of a nasogastric tube.

In alternative implementations, the fluid retrieval component 5802 and the housing 5502 may be integrally formed as a single piece. Turning to FIG. 60, in one example the housing 5502 and fluid retrieval component 5802 may be formed as a bulb-syringe 6000. The bulb-syringe comprises a bulb 6002 of a transparent, elastically deformable plastic, a nozzle 6004, and a one-way valve 6006. The detection indicator 6008 is shown embedded or attached to the bulb 6002, however in alternate implementations the detection indicator could be within the nozzle 6004. The practitioner may squeeze the bulb 6002 to expel air through the one-way valve 6006 (analogous to the second opening 5550) and then release the bulb to cause a suction force through a first opening 6010 of the housing 5502, as will be appreciated by those skilled in the art.

In yet another implementation, the housing 5502 is configured to engage a fluid retrieval component through the first opening 5540 (optionally, with an adapter). In this implementation, the fluid retrieval component is configured to expel the fluid sample into the interior chamber 5506 (through the first opening 5540) and the second opening 5550 is configured as a vent to relieve excess pressure as the fluid sample and/or any associated gases enter the housing 5502 while preventing the fluid sample from escaping the housing 5502. For example, the second opening 5550 comprises a "tortuous path" (e.g., with one or more corners or bends) that is sufficient to prevent the fluid sample from leaking or escaping the housing 5502 while allowing the escape of the associated gases or gases that are displaced from the housing 5502 by the fluid sample. Accordingly, the fluid sample is captured without an increase in pressure within the interior chamber 5506 and the fluid sample is prevented from escaping the housing 5502, as will be appreciated by those skilled in the art.

Turning to FIG. 61, the housing 5502 and fluid retrieval component are formed as a syringe 6100 that comprises a needle 6102, interior chamber 6104, and a plunger 6106. In a further example, a combination of fluid pressure (e.g., blood pressure) and pressure provided by the plunger are used to draw fluid into the interior chamber 6104 of the syringe 6100. The detection indicator 6108 in one example is adhered to the inside of the reservoir body 6104.

Turning to FIG. 62, the housing in one example comprises a test tube 6200 or vial with a first opening 6204. The detection indicator 6202 in this implementation comprises a color-change indicator and is adhered or affixed to an inside face of the test tube. A reference indicator 6206 is coupled with an outer surface of the test tube adjacent to the detection indicator 6202. Turning to FIG. 63, the housing in another example comprises a vacutainer 6300. The vacutainer has a small level of vacuum held by a membrane 6302 that is sealed against a tube 6304. A first end of a dual-ended needle (not shown) is inserted into the patient, then a second end of the dual-ended needle punctures the membrane 6302. The vacuum within the test tube then pulls blood or other fluid into the test tube where it contacts the detection indicators 6306. A reference indicator 6308 is affixed to an outer surface of the tube 6304. In the implementation shown in FIG. 63, the detection indicators 6306 are wrapped around a perimeter of the tube 6304 (e.g., wraparound configuration), as opposed to lengthwise as shown in FIGS. 61 and 62. The orientation of the detection indicator 6306 may be selected based on various design considerations. With the detection indicator 6306 located at one end of the tube 6304 in the wraparound configuration, a smaller fluid sample will be sufficient to saturate the various levels of the detection indicator 6306, as will be appreciated by those skilled in the art.

Turning to FIG. 64, another implementation of a housing 6400 has a detection indicator 6402 that is molded or partially encapsulated in a wall 6404 of the housing 6400. One or more passageways, capillaries, or openings 6406 allow the fluid sample to reach the detection indicator 6402. Turning to FIG. 65, in yet another implementation, a housing 6500 comprises an interior chamber 6502 with a divider 6504. The divider 6504 creates a separate channel 6506 where the detection indicator 6508 is located. The detection indicator in this example may be applied to an inner surface of the housing 6500, to a surface of the divider 6504, or placed in the separate channel 6506. An opening 6510 in the divider 6504 allows the fluid sample to reach the detection indicator 6508.

Figure 66:
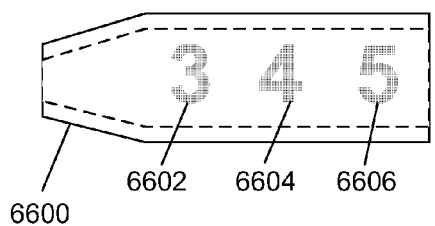
FIGS. 66-69 are partial side views of the housing with various implementations of the detection indicator.
Figure 67:
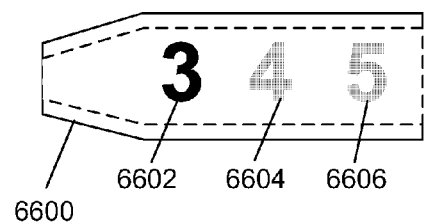

Turning to FIGS. 66 and 67, one implementation of the housing 6600 comprises detection indicators 6602, 6604, and 6606. The detection indicators 6602, 6604, and 6606 are configured to change from the first visual indicator (FIG. 66) to a second visual indication based on a pH of the fluid sample, for example, at pH levels of 3, 4, and 5, respectively. Referring to FIG. 67, upon contact with a fluid sample with a pH of 3, the detection indicator 6602 has changed to a second visual indication (i.e., a darker color relative to the first visual indication) to indicate the pH of the fluid sample.

Figure 68:
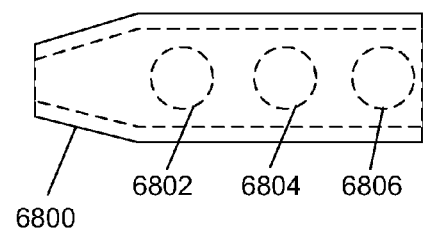
Figure 69:
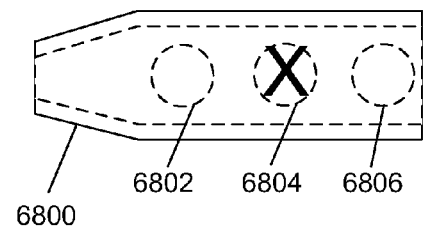

Turning to FIGS. 68 and 69, another implementation of the housing 6800 comprises detection indicators 6802, 6804, and 6806. Each detection indicator is configured to respond to a characteristic of the fluid sample. However, the detection indicators may be configured for the same characteristic to provide redundancy or for separate characteristics. Referring to FIG. 69, detection indicator 6804 has changed from a first visual indication that is clear (FIG. 68) to a second visual indication with a darkened "X".

Figure 70:
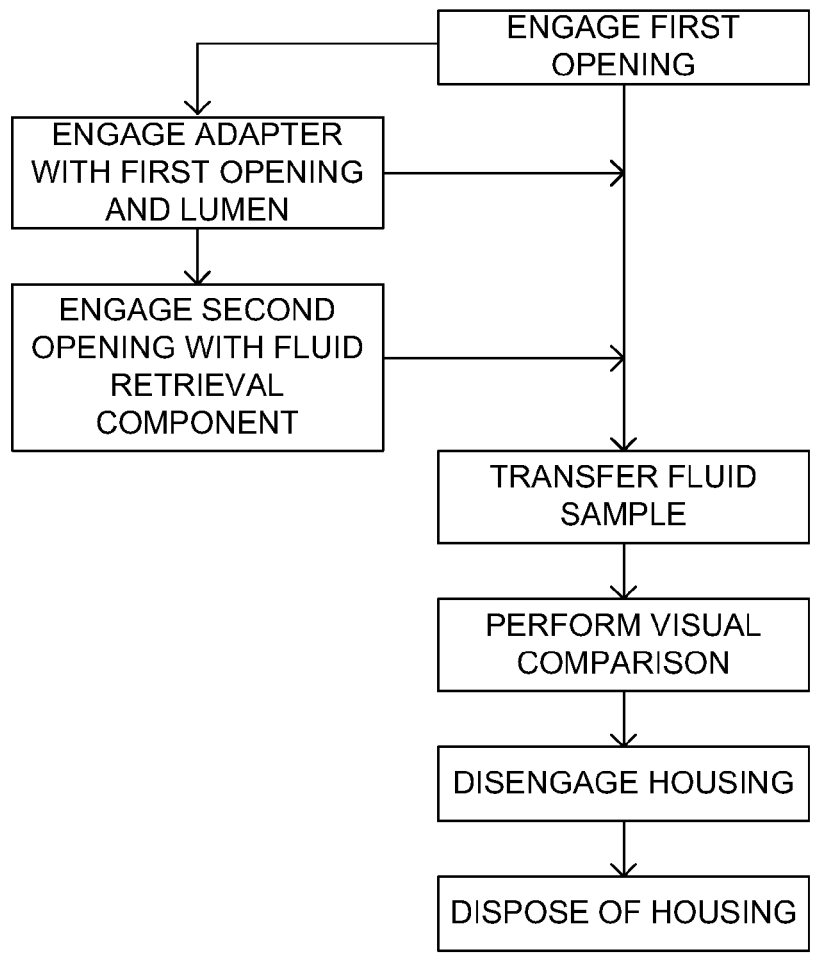
FIG. 70 is a logic flow for use of one implementation of the housing.

Turning to FIG. 70, a process flow shows one example of use for the apparatus 5500. The first opening of the removable housing is engaged with a proximal end of a lumen, such as a nasogastric tube. This may include engaging an adapter between the lumen and the first opening. Engagement of the first opening, the adapter, and the lumen creates a sealed channel between an interior of the lumen and an interior of the housing. Optionally, a second opening of the removable housing is engaged with the fluid retrieval component.

A transfer of a fluid sample from a distal end of the lumen, through the lumen, and into the removable housing through the first opening is then performed such that the fluid sample contacts the detection indicator 5504. For example, the practitioner activates the syringe or suction device to bring fluid from the distal end of the lumen (e.g., aspirate from the stomach) up through the lumen and into the interior chamber of the housing. The practitioner can then perform a visual comparison of the detection indicator 5504 with the reference indicator 5530 for determination of the characteristic of the fluid sample. For example, the practitioner observes the detection indicator 5504 for a change from a first visual indication to a second visual indication (e.g., from red to blue). After the observation, the practitioner disengages the removable housing by removing the first opening of the removable housing from the proximal end of the lumen. Optionally, the practitioner may dispose of the housing.

Figure 71:
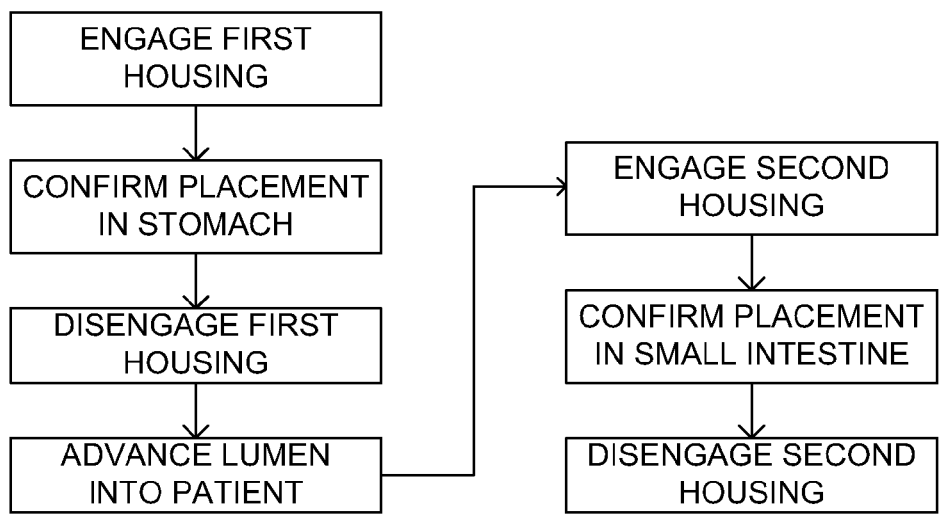
FIG. 71 is another logic flow for an alternate use of the housing.

Turning to FIG. 71, a process flow for determining placement of a lumen into the small intestine is shown. A first housing is engaged with the lumen, along with any necessary adapters or fluid retrieval component, as described above. Placement of the distal end of the lumen in the stomach is confirmed, for example, by reading a pH level of less than or equal to approximately 4.5 on the detection indicator 5504. The first housing is disengaged from the lumen and the distal end of the lumen is then advanced further into the patient, from the stomach into the small intestine. A second housing is engaged with the lumen. The pH of the small intestine is known to be approximately 6 and above and accordingly, placement of the distal end of the lumen in the small intestine can be confirmed with a second reading of the pH in or near this range. The second housing is then disengaged and optionally discarded. Additional readings or comparisons may be performed as needed to determine correct placement in alternate locations or to confirm that the lumen has not shifted or moved away from the desired location over a period of time.

FIG. 72 is a side elevation view of a further implementation of a fluid characteristic measurement apparatus 7200 according to an aspect of the invention. The apparatus 7200 may generally be constructed in a manner similar to the apparatus 5500 of FIG. 55-56, with certain variations from that construction noted hereinbelow. Accordingly, structures and features not specifically mentioned in connection with apparatus 7200 may be constructed or implemented in a manner similar to like structures and features of the apparatus 5500 of FIGS. 55-56. As best seen in FIG. 72, apparatus 7200 comprises a generally tubular body housing 7202 defining a central lumen 7236 between and in fluid communication with a first opening 7240 and a second opening 7250. In a clinical application, second opening 7250 of housing 7202 is configured to removably engage or couple to a conduit adapted for fluid-transfer coupling with a patient through which a fluid sample to be measured is obtained. The conduit may, for example but without limitation, be a nasogastric tube inserted into the stomach of a medical patient. Thus, fluids, such as bodily fluids from a medical patient, may flow between the openings 7420 and 7250 and through the central lumen 7236. The central lumen 7236 opens into and is in fluid communication with an interior chamber 7206, which in some implementations may be of larger diameter than the central lumen 7236. Apparatus 7200 further comprises a detection indicator 7204 which is disposed in the interior chamber 7206 or in fluid communication therewith. Thus, when fluid is present in central lumen 7236, the interior chamber 7206 provides contact between the fluid and the detection indicator in that the fluid also occupies the interior chamber 7206 and may saturate the detection indicator 7204. The detection indicator 7204 is configured to display or exhibit at least one visual indication, appearance or other externally detectable manifestation that is responsive to the fluid characteristic or characteristics being measured by the apparatus 7200. For examples but without limitation: the detection indicator 7204 may respond upon or when in contact with the fluid; the characteristic being measured or detected may be a chemical or physical property of the fluid, such as pH; the fluid may be a body fluid; and more particularly, the body fluid may be a liquid, such as gastric aspirate from a medical or veterinary patient.

In some implementations, the detection indicator 7204 may be constructed as generally shown in connection with apparatus 5500 of FIGS. 55-56. For example, the detection indicator 7204 may be formed as a strip of or containing an indicating medium or material responsive to the fluid characteristic being measured. In some implementations, the fluid characteristic being measured is pH, and the detection indicator 7204 is constructed from an indicating medium such as litmus paper or pH indicating paper, and may be disposed as a strip thereof oriented generally parallel to the major longitudinal axis of the housing 7202 (i.e., where the apparatus 7200 is used in a preferred vertical orientation, the detection indicator 7204 strip is similarly vertically oriented). However, the detection indicator 7204 is not limited to measuring pH, and could be used to measure any characteristic or property for which there is an available detection indicating component which exhibits a visual appearance or other externally detectable manifestation that is responsive to the detected characteristic or property, including but not limited to proteins, enzymes, the presence of specific gases, temperature, and the like, as earlier described in connection with apparatus 5500 of FIGS. 55-56.

Apparatus 5500 of FIGS. 55-56 includes structures to support the detection indicator in a desired location and to enable the detection indicator to be saturated by fluid present in the interior chamber. Apparatus 7200 may, for example, contain equivalent structures (not shown in FIG. 72). For example, the generally tubular structure of housing 7202 may be relieved by one or more detection openings (equivalent to 5508, 5510) allowing fluid in the interior chamber 7206 to exit. The detection indicator 7204 may be disposed outside and adjacent the openings, essentially outside the tubular envelope of the housing 7202. One or more support posts (equivalent to 5512) may be provided to maintain the structural integrity of the housing 7202 and to keep the detection indicator 7204 from migrating into the interior chamber 7206. One or more ribs (equivalent to 5513 and 5522) may be used to space the detection indicator 7204 diametrically to form one or more channels (equivalent to 5514) on the exterior of the principal housing structure to promote fluid flow among the detection openings and the detection indicator 7204.

A substantially optically transparent sealing member 7216 covers the detection indicator 7204 and forms a seal with the housing 7202 to prevent leakage of fluids. The term "seal" and related terms used herein denote a substantially fluid-impervious seal during the use and subsequent handling of the apparatus. In one implementation, the sealing member 7216 forms generally tubular fluid-impervious barrier around a portion of the housing 7202. Ribs (equivalent to 5519 and 5521) at opposite ends of the area of the detection openings provide structures or surfaces against which the sealing member 7216 may seal and diametrically space the sealing member 7216 to provide room for the detection indicator 7204. Sealing channels (equivalent to 5518 and 5520) are provided to receive a sealant, adhesive, or structural seal (for example, but without limitation, a thermal, pressure, or ultrasonic weld), to further seal the sealing member 7216 to the housing 7202.

In some embodiments, the sealing member 7216 is formed integrally with the principal structure of the housing 7202, for example, as a flap of material similar or identical to that used to construct the housing 7202 and arranged so as to allow the sealing member 7216 to be wrapped circumferentially around the principal structure of the housing 7202 forming the aforementioned tubular barrier. Any appropriate sealing technology could be used to create a seal involving any one or more of the ribs 7219, 7221, and the sealing channels 7218, 7220. In commercial production, the detection indicator 7204 may be attached, prior to the circumferential wrapping operation, to the interior surface of the sealing member 7216 using any appropriate attachment technology, including for example, but without limitation, an adhesive, or a structural attachment such as a thermal, pressure, or ultrasonic weld. This allows the detection indicator 7204 to be reliably located with respect to the detection openings. For example, where the detection indicator 7204 is implemented using an indicator medium of a pH sensitive paper strip, the strip may bear an optically clear adhesive that enables the strip adhere to a surface of the sealing member 7216. Alternatively, or in addition, an optically clear adhesive could be provided on a surface of the sealing member 7216 in the area where the detection indicator 7204 is to reside. The use of an optically clear adhesive allows the appearance of the strip to be viewed through the adhesive and sealing member 7216. However, the detection indicator 7204 could also be attached to other components of the housing or could be allowed to float. Sealing member 7216 could also be formed in other ways. For example, sealing member 7216 may be formed, for example, as a component discrete from the housing 7202 and could be wrapped circumferentially as earlier described, or could be formed as a tube into which the housing 7202 is telescoped or nested during assembly. If formed as a tube, sealing member 7216 could, for example, be made from a heat-shrinkable material and shrunk during assembly to form a substantially fluid-impervious seal. Other configurations and assembly steps could also be used.

Apparatus 7200 further comprises an exoskeletal member or outer shell 7226 ("exoskeleton") nestably disposed around the principal structure of the housing 7202 which provides additional stiffness to the housing 7202 and serves as additional barrier to fluid leakage, in case the primary seal provided by sealing member 7216 is inadequate during use. One of skill in the art will appreciate that leakage of liquid body fluids, including but not limited to gastric aspirate, from apparatus 7200 is undesirable, as such fluids may contain pathogens or other hazards, and the fluids may come in contact with personnel or require effort for containment and disposal. The exoskeleton 7226, or at least a portion thereof, is preferably substantially optically transparent to allow the detection indicator 7204, and any reference indicator 7230 which may be disposed within the exoskeleton 7226 to be simultaneously viewable. As best seen in FIG. 72, in one implementation, the right-hand end of the housing 7202 has a diameter narrow enough to allow the exoskeleton 7226 to be telescoped over that end, which the left-hand end of the housing has a diameter wide enough to stop the exoskeleton 7226 from telescoping past that end. A retaining ring 7228 also telescopes over the right-hand end of the housing 7202 to retain the exoskeleton 7226 in place on the housing 7202. The retaining ring 7228 may be attached to the housing any appropriate attachment technology, including for example, but without limitation, an adhesive, or a structural attachment such as a thermal, pressure, or ultrasonic weld. One or more sealing components 7232 may be provided to seal the exoskeleton 7226 to the housing 7202 and aid in preventing leakage. The sealing component 7232 may be a formed, for example, as a structure, such as a rib or ridge on the exterior of the housing 7202, the interior of the exoskeleton 7226, some cooperative combination of these, or as a sealant or adhesive, or as a weld. Exoskeleton 7226 could also be retained using different configurations. For example, if the housing 7202 has a narrow diameter at both ends, retaining rings could be provided on both ends. Alternatively, the exoskeleton 7226 could be attached to the housing 7202 using any appropriate attachment technology, including for example, but without limitation, an adhesive, or a structural attachment such as a thermal, pressure, or ultrasonic weld.

Apparatus 7200 may further comprise one or more adaptors 7234 for coupling the apparatus 7200 to a conduit or other apparatus, including but not limited to a nasogastric tube, a feeding tube, a suction or vacuum source, a syringe or vacuum bulb, or other tubing or piping. As best seen in FIG. 72, adaptor 7234 may be formed as a two-ended barb with a structure for secure but removable attachment to flexible tubing, or appropriate ports for fluid communication on other apparatus. However, this is merely one example of an adaptor, and adaptors of numerous different configurations, and combinations of adaptors, could also be used. For example but without limitation, a short piece of flexible tubing of appropriate size may serve as an adaptor for connecting to apparatus that has a barb or similar fitting for connection to tubing.

Figure 89:
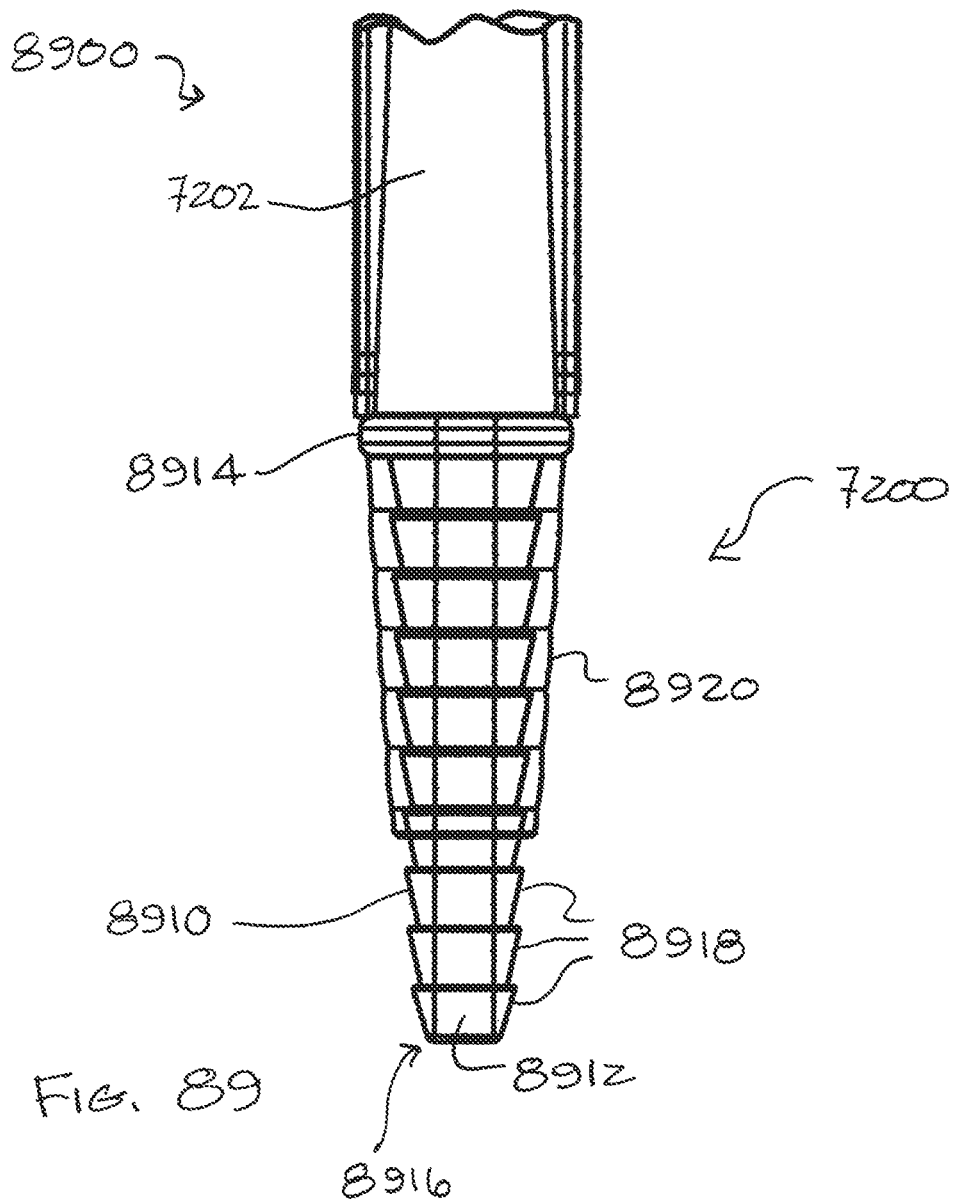
FIG. 89 is a side elevation view depicting in part one implementation of an adaptor for use with the apparatus of FIGS. 72-74 and other similar apparatus.

FIG. 89 is a side elevation view of a portion of an implementation of the adaptor 7234. Adaptor 7234 may comprise a generally rigid body 8910 having an interior lumen or channel 8912. The adaptor body 8910 meets the apparatus housing 7202 at about the middle 8914 of the adaptor; the remainder of the adaptor is inside the housing 7202 but may be symmetrically constructed. The diameter of the adaptor body 8910 tapers from a wider diameter at the middle 8914 to a tube connection end 8916. A series of conical ribs 8918, successive ones of which having successively smaller diameters as the tube connection end 8916 is approached, are provided to capture resilient tubing pushed over the ribs. A conformal sleeve 8920 extends a part of the distance from the middle 8914 to the tube connection end 8916 and covers circumferentially the exterior surface of at least some of the ribs. The sleeve 8920 may be formed, e.g., from a resilient silicone material that surrounds and conforms to the ribbed structure of the adaptor body 8910. The resilient sleeve aids in engagement of the adaptor with larger tubing or accessory openings.

Apparatus 7200 may further optionally comprise a filter 7242 to avoid fouling of the apparatus due to solids carried in the fluid being tested. When the apparatus 7200 is used with a nasogastric tube, for example, to measure characteristics of a patient's gastric fluids, it is typical that food solids may be present. Any solids may undesirably obstruct fluid flow in the region of the detection indicator 7204; filter 7242 may help prevent such obstruction. An appropriate filter configuration may vary with applications. In one example, a filter with approximately 1-mm openings could be used to ensure that the aspirate drawn into the interior chamber 7206 and the region of the detection indicator 7204 is free of large particles that may obstruct flow of fluid around the detection indicator 7204 so as to ensure complete saturation of the detection indicator 7204.

Apparatus 7200 may further optionally comprise a one-way valve 7244 to prevent fluids that have been aspirated into the apparatus 7200 from flowing out of the apparatus 7200 towards their source. This helps prevent leakage of bodily fluids and helps personnel avoid contact with the leaked fluids. The one-way valve 7244 allows fluid movement in a preferred direction (e.g., from the second opening 7250 toward the central lumen 7236 and interior chamber 7206 and substantially prevents fluid movement in the non-preferred direction. One-way valve 7244 may for example be constructed using a single flap, vane, or ball which is displaced by fluid pressure in the preferred direction of fluid movement to allow such movement, but which engages a seat when fluid pressure is present in the non-preferred direction. The flap, vane, or ball may be operated solely by fluid pressure or may be urged toward the seat by a resilient member or function, which may be embodied as part of the flap or vane, or may be provided by a separate spring or the like. One-way valve 7244 may also be constructed as a pair of opposed flaps or vanes having movable ends pointing toward the preferred fluid-flow direction, and under resilient pressure to urge the flaps or vanes together in the absence of fluid pressure in the preferred direction. Fluid pressure in the preferred direction forces the flaps or vanes apart to allow fluid flow. Fluid pressure in the non-preferred direction urges the flaps or vanes together to substantially prevent fluid movement in the non-preferred direction. Any other appropriate one-way valve structure could also be used to implement one-way valve 7244. A one-way valve similar to valve 7244 could also be provided in a barb or similar fitting for connection to tubing, or in an adaptor. Because the valve 7244 does not require manual operation, it may be considered an "automatic valve".

As a supplement to, or instead of the one-way valve 7244, a cap (not shown) may be applied to one or each end of the apparatus 7200 after its use to prevent leakage of bodily fluids and avoid exposure of personnel thereto.

As an alternative or supplement to the one-way valve 7244, apparatus 7200 may comprise a manually operated valve, as disclosed further in connection with FIG. 87.

The housing 7202, sealing member 7216, and retaining ring 7228 may be constructed of any suitable material which is compatible with the fluids being sampled, and is preferably optically transparent or translucent such that the detection indicator 7204 is visible therethrough. For example, housing 7202 and sealing member 7216 may be formed from a moldable silicone material. A suitable material is commercially available from Dow as type C6-570 silicone. Other materials could also be used. A similar material could be used for conformal sleeve 8920. The retaining ring 7228 may be formed from an extruded silicone material. A suitable material is commercially available from Dow as type as type Q7-4780 silicone. These components could also be formed from a harder plastic material, which may cure more rapidly than silicone materials. Other materials could also be used. The exoskeleton 7226 may be constructed of any suitable material which is compatible with the fluids being sampled and is preferably optically transparent or translucent such that the detection indicator 7204 is visible therethrough. The exoskeleton 7226 preferably has sufficient mechanical strength to avoid significant deformation under normal use, so that it may protect housing 7202 from damage that would disrupt any of the seals therein that are designed to prevent leakage of the sample fluid, and so that any of the seals between the exoskeleton 7226 and the housing 7202 are not disrupted during use. A suitable material for the construction of exoskeleton 7226 is glycol-modified polyethylene terephthalate (PETG), which may be obtained or formed as a tube. Although the several components may have various degrees of hardness, softness, rigidity, flexibility, resilience, and the like, it not necessary that they be constructed of different materials, as suitable characteristics may be obtained from a single material (and even a single piece of material), e.g., by curing them differentially using ultraviolet light. Thus, an implementation could be constructed using a single piece of material for the housing, and some portions thereof could be made softer, e.g., at the barb fitting, while other portions, such as the middle, may be made harder to provide desired structural integrity.

Apparatus 7200 may further comprise a reference indicator 7230 against which the appearance of the sealing member 7216 may be compared to enable the user to ascertain a measurement value or other useful information. For example, if detection indicator 7204 is implemented as a pH paper that exhibits a color responsive to the pH of the fluid to which it is exposed, the reference indicator 7230 may comprise one or more color samples which guide the user regarding how to interpret the color displayed by the detection indicator 7204 as a measurement or as an indication of some event or condition, regardless of whether such indication is considered a "measurement" in the traditional sense. The reference indicator 7230 is preferably disposed to be optically adjacent or juxtaposed with respect to the detection indicator 7204 so that the user can make an accurate comparison between them with minimal delay.

Some indicating media, such as pH indicator strips, are stable for only a short period of time after exposure to a sample. In addition, the measured or detected characteristic of the sample itself may change soon after being collected. Thus, the indicating appearance of detection indicator 7206, e.g., a change in color, may occur immediately upon exposure of the detection indicator 7206 to the sample, and should be read soon thereafter. In some cases, it is preferred to read the indicator within about one minute, and therefore, it is sometimes desirable to for measurement or detection of the characteristic of interest to occur bedside, immediately upon collection, and before instability in either the detection indicator 7206 or the sample invalidates the reading. Providing a reference indicator 7230 (which, in some examples may be a color chart) against which the appearance of the detection indicator 7206 may be compared, that accompanies or is integrated with the apparatus 7200, may aid in the rapid detection or measurement of the sample after collection, for example, at bedside. Taking the sample away from the patient and arranging the apparatus near a separate reference indicator for comparison could delay the comparison, thereby decreasing the accuracy of any measurement or detection, and could also increase the likelihood of exposure of personnel to bodily fluids.

If the apparatus 7200 is to be used by a person performing a visual inspection, it is believed that a reference indicator 7230 minimizes ambiguity in the result and helps avoid error. However, in some implementations, a reference indicator may not be necessary. For example, the detection indicator 7204 could provide a result that is unambiguous even without a reference for comparison. For another example, the sensing of the measurement result could be performed using equipment that includes an internal reference or standard or employs a sensor that produces reliable measurements without a reference or sensor.

Figure 73:
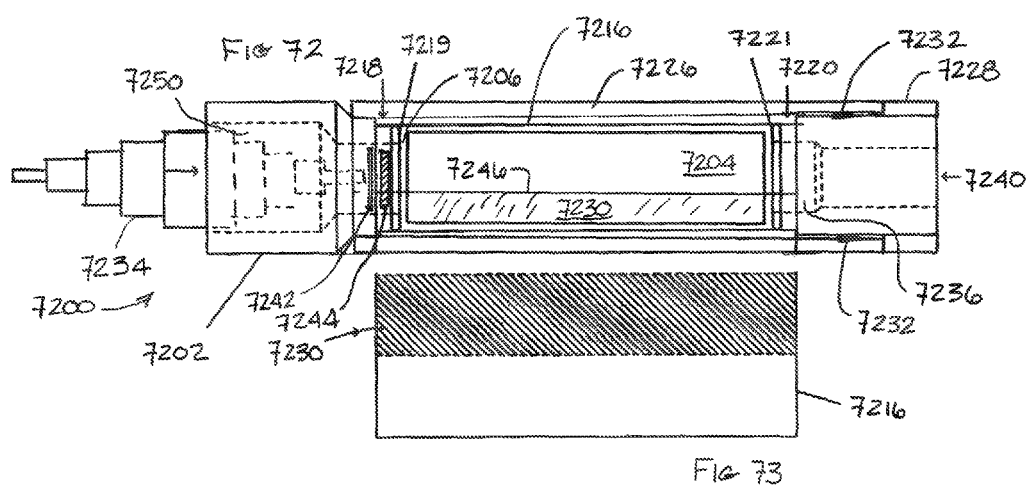
FIG. 73 is a plan view of a portion of a sealing member of the fluid characteristic measurement apparatus of FIG. 72.

FIG. 73 is a plan view of a portion of sealing member 7216 arranged in its flat configuration and bearing a reference indicator 7230 on a surface thereof. The reference indicator 7230 is preferably arranged such that when the sealing member 7216 is circumferentially wrapped around the principal structure of housing 7202, both the detection indicator 7204 and the reference indicator 7230 are optically adjacent or juxtaposed. For example, the reference indicator 7230 may be applied to what will become the outer surface of the sealing member 7216 after it is wrapped around the housing. The reference indicator 7230 may be formed from paper, plastic sheet, or other suitable material, and the samples and indicia may be printed or formed using any suitable method. The reference indicator 7230 could also be formed as a part of the housing 7202, for example, by molding or otherwise disposing materials displaying the sample colors or other representations, along with any necessary interpretive indicia, into the housing.

FIG. 75 is a simplified cross-section view taken across the major longitudinal axis of the apparatus 7200, showing the relative placement of the housing 7202, the interior chamber 7206, a support post 7512, the detection indicator 7204, the sealing member 7216, the reference indicator 7230, the reference indicator window 7246, and the exoskeleton 7226.

It will be appreciated that several other configurations of these various components can be used to construct suitable fluid characteristic measurement apparatus according to aspects of the invention.

Figure 74:
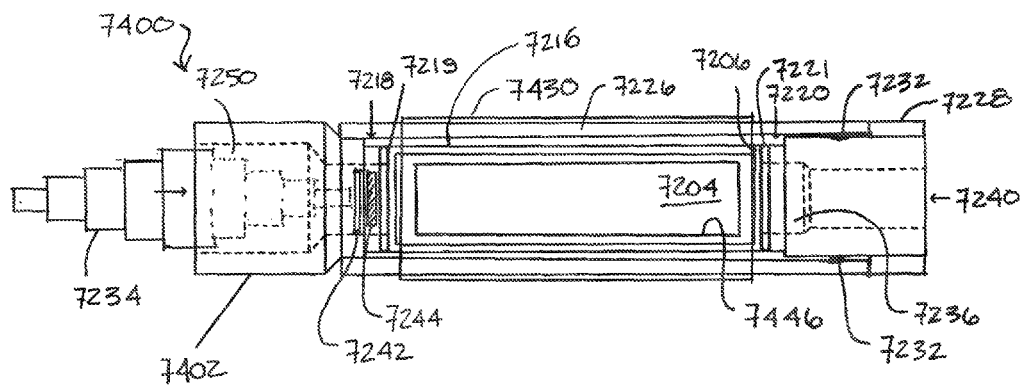
FIG. 74 is a side elevation view of a further implementation of a fluid characteristic measurement apparatus constructed according to an aspect of the invention.

FIG. 74 is a side elevation view of a further implementation of a fluid characteristic measurement apparatus 7400 in which certain components are arranged in an alternate configuration. The apparatus 7400 may generally be constructed in a manner similar to the apparatus 7200 of FIGS. 72-73 and 75, with certain variations from that construction noted hereinbelow. Items substantially the same as shown in FIGS. 72-73 and 75 retain the reference characters from those Figs. Accordingly, structures and features not specifically mentioned in connection with apparatus 7400 may be constructed or implemented in a manner similar to like structures and features of the apparatus 7200 of FIGS. 72-73 and 75. As best seen in FIG. 74, apparatus 7400 comprises a housing 7402, a exoskeleton 7226, and a reference indicator 7430. Reference indicator 7430 may be disposed around the outer circumference of exoskeleton 7226, instead of on a surface of sealing member 7216 as shown in FIGS. 72-73 and 75. For example, but without limitation, the reference indicator 7430 may be wrapped around some portion (such as half), or all, of the circumference or perimeter of the exoskeleon 7226. Reference indicator 7430 includes a reference indicator window 7446, through which detection indicator 7204 is generally visible. In connection with all instances of the reference indicator window herein, the term "window" is intended to refer to an optically clear region through which the detection indicator may be viewed. The window may be implemented, for example, as a transparent film, or as an aperture in the material of the reference indicator 7430. The detection indicator 7204 and the reference indicator 7430 are optically adjacent or juxtaposed, such that indication samples of the reference indicator 7430 and the detection indicator 7204 may be compared. Reference indicator 7430 may be formed from paper, plastic sheet, or other suitable material, and the samples and indicia may be printed or formed using any suitable method. Reference indicator 7430 may be attached to exoskeleton 7226 using any appropriate attachment technology, including for example, but without limitation, an adhesive, or a structural attachment such as a thermal, pressure, or ultrasonic weld. Reference indicator 7430 could also be formed, for example, as a tube of a heat-shrinkable material; in assembly, the rest of the apparatus 7400 may be telescoped inside the tube, and heat may then be applied to shrink the tube to securely engage the outer surface of exoskeleton 7226.

FIG. 78 is a simplified cross-section view taken across the major longitudinal axis of the apparatus 7400, showing the relative placement of the housing 7402, the interior chamber 7206, a support post 7812, the detection indicator 7204, the sealing member 7216, the reference indicator 7430, reference indicator window 7446, and the exoskeleton 7226. The reference indicator 7430 is disposed around the exterior of exoskeleton 7226.

Figure 76:
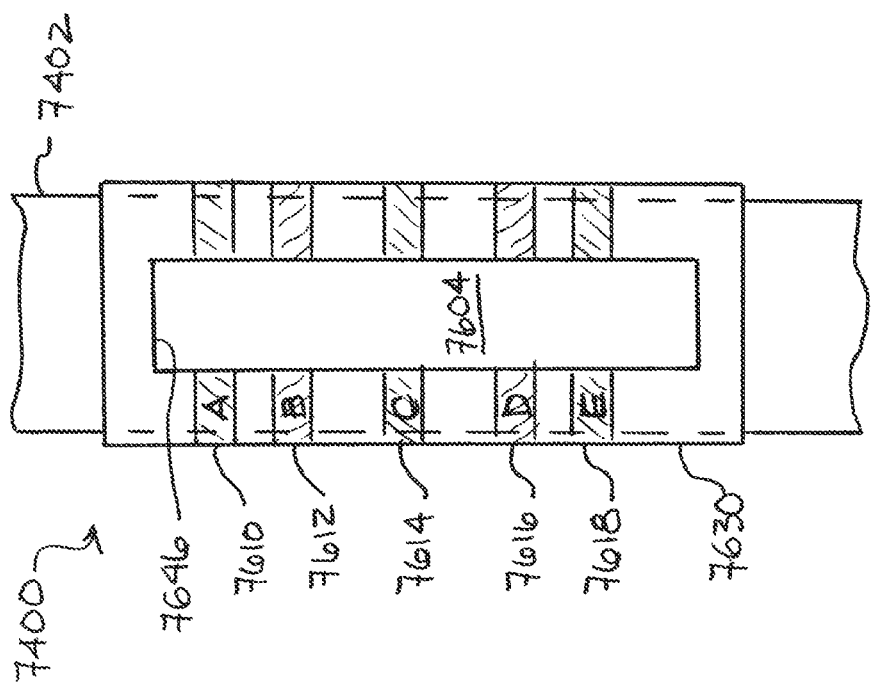
FIG. 76 is a side elevation view depicting an example implementation of the reference indicator of the fluid characteristic measurement apparatus of FIG. 74, showing an example configuration of several reference samples and measurement indicia.

FIG. 76 is a side elevation view depicting an example implementation of the reference indicator of apparatus 7400, showing an example configuration of several reference samples and measurement indicia. In use, the apparatus 7400 is preferably disposed such that its major longitudinal axis is substantially vertical. The reference indicator is denoted as 7630. Several reference samples 7610, 7612, 7614, 7616, and 7618 are disposed along the reference indicator window 7646, such that the detection indicator 7604 can be compared against each of the reference samples. Indicia A, B, C, D, and E are visible to provide measurement guidance for the reference samples 7610, 7612, 7614, 7616, and 7618 respectively, so that the user may report or record as the measurement result the indicium corresponding to the reference sample that most closely matches the indication provided by the detection indicator 7604. A reference indicator having only a single reference sample allows the user to discern that the characteristic being measured exceeds (or does not exceed) the threshold defined the reference indicator. The plurality of reference samples of reference indicator 7430 thus enables the user to discern and record a specific measurement of the characteristic of interest, subject to the resolution enabled by the number, range, and measurement "distance" between the several reference samples. Producing a specific measurement is needed in some applications, e.g., where knowing that a sample exceeds or does not exceed a simple threshold is inadequate for diagnosis or treatment decisions. The capability to obtain a specific measurement of, for example, pH, can eliminate the need for expensive instrumentation to measure gastric pH, or to send a sample to the laboratory. The ability to monitor pH using actual pH measurements, obtained rapidly, at low cost, and with little time investment by the practitioner, may encourage practitioners to employ such measurements in decision-making more often than they would otherwise, thereby improving patient outcomes.

Figure 77:
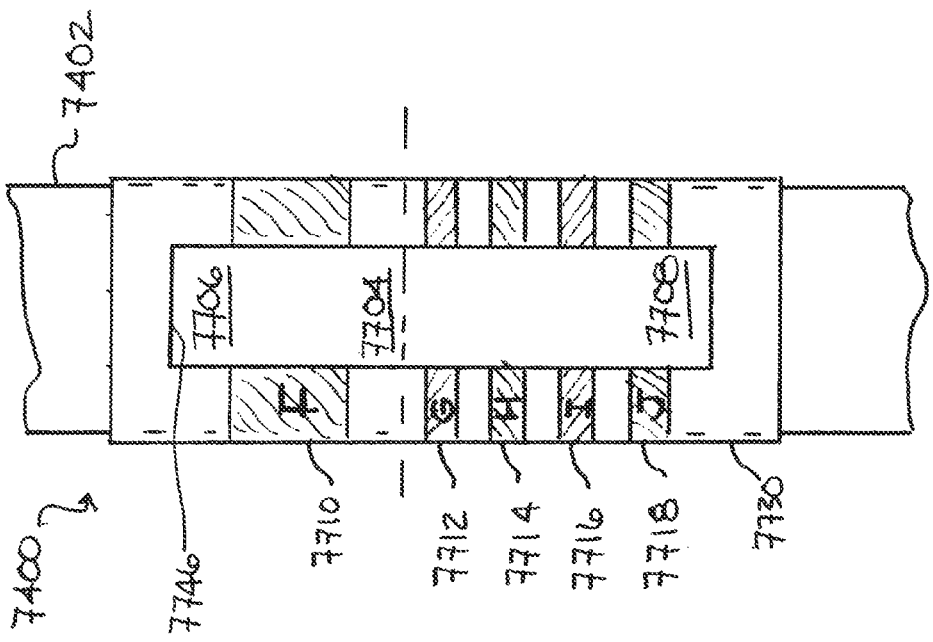
FIG. 77 is a side elevation view depicting a further example implementation of the reference indicator of the fluid characteristic measurement apparatus of FIG. 74, showing an further example configuration of several reference samples and measurement indicia.

FIG. 77 is a side elevation view depicting a further example implementation of the reference indicator of apparatus 7400, showing a further example configuration of several reference samples and measurement indicia. The reference indicator is denoted as 7730. Although a single monolithic detection indicator has been mentioned in connection with earlier-described implementations, the detection indicators herein could be implemented using plural detector media or zones or portions thereof, ones of which may detect or measure different characteristics or parameters, or may display results along different scales or in different manners. The detection indicator 7704 of FIG. 77 is divided into a first detection indicator section 7706 and a second detection indicator section 7708. In general, it is preferred that the several fluid characteristic measurement apparatus disclosed herein, when in operation, are oriented such that principal longitudinal axis is vertical or nearly so. It is believed that an orientation of the apparatus within about 25 degrees of vertical is optimum, but the apparatus will be operable for deviations greater than 25 degrees from vertical. The nearly vertical orientation allows for the interior chamber to fill with fluid and requires the aspiration of less fluid to reliably saturate the detection indicator than would be required for other orientations. Accordingly, as best seen in FIGS. 76 and 77, legends and other indicia which are provided on the reference indicators and which are expected to be read by a user during operation are at least oriented so that they are easily readable when the apparatus is used in a vertical orientation.

In one implementation, the first detection indicator section 7706 is equipped with a detector medium to provide a simple, unambiguous indication that fluid present in the apparatus has a pH below 4.5. When used with a nasogastric tube through which fluid has been aspirated, the presence of fluid of pH below 4.5 indicates that the nasogastric tube has been correctly inserted into the stomach, because the stomach is the only source of bodily fluid with pH below 4.5. The reference indicator 7730 comprises a reference sample 7710 adjacent to and juxtaposed with the first detection indicator section 7706 that exhibits the color or other appearance of the first detection indicator section 7706 when the pH is below 4.5. The indicium F corresponds to successful insertion and placement of the nasogastric tube in the stomach. Any appropriate indicator medium could be used to implement first detection indicator section 7706. For example, first detection indicator section 7706 may be implemented using a phenaphthazine paper sensor strip commercially available from Micro Essential Laboratory, Brooklyn, N.Y. 11210, under the designation pHizatest #934. This indicator medium could be used to implement any of the detection indicators described herein where the application requires an unambiguous indication that fluid present in the apparatus has a pH below 4.5. Other indicating media could also be used. Although in one implementation the fluid characteristic measurement apparatus is used to determine correct placement of a nasogastric tube in a patient's stomach, the fluid characteristic measurement apparatus could also be used to determine correct placement of a tube in other bodily-fluid-bearing locations, such as a patient's intestine, lungs, or esophagus. For locations other than a patient's stomach, it may be necessary to select a different detection indicator which is appropriate to sense a fluid characteristic unique to the location for which correct placement is to be determined.

The second detection indicator section 7708 is equipped with a detector medium to provide a measurement of pH along a defined range by providing a continuum of color indications responsive to pH within the range. In use, the second detection indicator section 7708 may be used, for example, to observe and record a measurement of pH once the practitioner has determined, using the first detection indicator section 7706 and corresponding reference indicator sample 7710, that the nasogastric tube has been correctly inserted. The reference indicator 7730 further comprises reference samples 7712, 7714, 7716, and 7718, disposed along the reference indicator window 7746, and adjacent to and juxtaposed with second detection indicator section 7708, corresponding to selected pH values represented by respective indicia G, H, I, and J, such that the second detection indicator section 7708 can be compared against each of the reference samples. The user may report or record as the measurement result the indicium corresponding to the reference sample that most closely matches the indication provided by the detection indicator reference samples. Any appropriate indicator medium could be used to implement second detection indicator section 7708. For example, second detection indicator section 7708 may be implemented using a pH paper sensor strip commercially available from Micro Essential Laboratory, Brooklyn, N.Y. 11210, under the designation Hydrion pH paper 1-6 #52. This indicator medium could be used to implement any of the detection indicators described herein where the application requires a pH measurement in the range of about 1 to 6. Other indicating media could also be used.

In another implementation, the first detection indicator section 7706 is equipped with an indicating medium to provide a simple, unambiguous indication that sufficient fluid has been aspirated into the apparatus to saturate both first detection indicator section 7706 and second detection indicator section 7708. Since the apparatus is preferably used in a near-vertical orientation, and sample fluid is drawn from the bottom of the apparatus, the position of the first detection indicator section 7706 above second detection indicator section 7708 means that in order for fluid to reach the first detection indicator section 7706, it must first substantially fill the interior chamber in the region of the second detection indicator section 7708. As a result, if any fluid reaches first detection indicator section 7706, it may be assumed that the second detection indicator section 7708 has already been thoroughly saturated. Thus, in this configuration, the appearance of the first detection indicator section 7706 provides an unambiguous signal or confirmatory indicator that the second detection indicator section 7708 is saturated and a reading taken therefrom will be valid. As one example, first detection indicator section 7706 may employ a detection medium that exhibits a significant color change, such as from white to black, when exposed to any liquid.

Any of the reference indicators disclosed herein may use a configuration of reference samples, indicia, and reference indicator window similar to that shown in FIG. 76 or 77, and described in connection therewith. Other configurations could also be used depending on the requirements of the application. Where the fluid characteristic measurement apparatus is intended to provide a binary indication, e.g., of success or failure in nasogastric tube placement, rather than an indication of a closest one of several possible measurement values, a simpler configuration of the reference indicator may be used.

Still other configurations of the detection indicator, the reference indicator, and various structural components may be used to construct suitable fluid characteristic measurement apparatus according to aspects of the invention.

FIG. 79 depicts a further implementation of a fluid characteristic measurement apparatus 7900 in which certain components are arranged in an alternate configuration. FIG. 79 is a simplified cross-section view taken across the major longitudinal axis of the apparatus 7900. The apparatus 7900 may generally be constructed in a manner similar to the apparatus 7400 of FIGS. 74 and 78, with certain variations from that construction noted hereinbelow. Accordingly, structures and features not specifically mentioned in connection with apparatus 7900 may be constructed or implemented in a manner similar to like structures and features of the apparatus 7400 of FIGS. 74 and 78. Apparatus 7900 comprises a generally tubular housing 7902 defining an interior chamber 7906. A detection indicator 7904 is housed or disposed in a space adjacent interior chamber 7906. Detection openings in the housing 7902 provide a path for fluid communication between the interior chamber 7906 and the space in which the detection indicator 7904 resides. A support post 7912 has functions similar to the support post 7212 of FIGS. 72 and 74. A sealing member 7916 covers the space in which the detection indicator 7904 resides and forms a seal with the housing 7902 to prevent leakage of fluids. A generally tubular exoskeleton 7926 surrounds the housing 7902. Apparatus 7900 further comprises a reference indicator 7930 disposed on or adjacent the interior surface of the exoskeleton 7226 (as compared to the apparatus 7400 of FIGS. 74 and 78, in which the reference indicator is disposed on the outside of the exoskeleton 7226). A reference indicator window 7946 is provided to allow the detection indicator 7904 to be viewed. The reference indicator 7930 may be formed, and may be fixed or attached in place as described in connection with FIGS. 74 and 78.

FIG. 80 depicts a further implementation of a fluid characteristic measurement apparatus 8000 in which certain components are arranged in an alternate configuration. FIG. 80 is a simplified cross-section view taken across the major longitudinal axis of the apparatus 8000. The apparatus 8000 may generally be constructed in a manner similar to the apparatus 7200 of FIGS. 72-73 and 75, with certain variations from that construction noted hereinbelow. Accordingly, structures and features not specifically mentioned in connection with apparatus 8000 may be constructed or implemented in a manner similar to like structures and features of the apparatus 7200 of FIGS. 72-73 and 75. Apparatus 8000 comprises a generally tubular housing 8002 defining an interior chamber 8006. A detection indicator 8004 is disposed in a space adjacent interior chamber 8006. Detection openings in the housing 8002 provide a path for fluid communication between the interior chamber 8006 and the space in which the detection indicator 8004 resides. A support post 8012 has functions similar to the support post 7212 of FIG. 72. A sealing member 8016 covers the space in which the detection indicator 8004 resides and forms a seal with the housing 8002 to prevent leakage of fluids. A generally tubular exoskeleton 8026 surrounds the housing 8002. Apparatus 8000 further comprises a reference indicator 8030 disposed on or adjacent the interior surface of the sealing member 8016 (as compared to the apparatus 7200 of FIGS. 72-73 and 75, in which the reference indicator is disposed on the exterior surface of the sealing member 7216). A reference indicator window 8046 is provided to allow the detection indicator 8004 to be viewed. The reference indicator 8030 may be formed, and may be fixed or attached in place as described in connection with FIGS. 72-73 and 75.

FIG. 81 depicts a further implementation of a fluid characteristic measurement apparatus 8100 in which certain components are arranged in an alternate configuration. FIG. 81 is a simplified cross-section view taken across the major longitudinal axis of the apparatus 8100. The apparatus 8100 may generally be constructed in a manner similar to the apparatus 7400 of FIGS. 74 and 78, with certain variations from that construction noted hereinbelow. Accordingly, structures and features not specifically mentioned in connection with apparatus 8100 may be constructed or implemented in a manner similar to like structures and features of the apparatus 7400 of FIGS. 74 and 78. Apparatus 8100 comprises a generally tubular housing 8102 defining an interior chamber 7906.

Although earlier descriptions of apparatus herein have generally disclosed a detection indicator formed as a discrete element, such as a strip of indicating paper, other detection indicators could be used. For example but without limitation, the detection indicator may be impregnated or embedded in a matrix or coating, that may be applied or attached to a surface. As best seen in FIG. 81, a detection indicator 8104 is formed in such a manner and applied to an interior surface of housing 8102 in the area of interior chamber 8106. For example, detection indicator 8104 may be formed as one or more rings or bands of material coating or applied to the interior surface. The detection indicator 8104 may encircle the circumference of the interior surface entirely, or may be applied to only a portion of the circumference of the interior surface. This form of detection indicator may require less longitudinal distance along the housing 8102 than other forms, allowing a more compact device, and may require a smaller quantity of indicating medium than other configurations require. The detection indicator 8104 may be formed in distinctive patterns to enhance the ability of a user to recognize the state of the detection indicator 8104. The detection indicator 8104 could also be formed in multiple sections having sensitivity or responsiveness to plural fluid characteristics or properties, or plural ranges thereof. Separate interior chambers (not shown) may be provided, e.g., an independent interior chamber respectively associated with each of the detection indicator sections, to optimize saturation of or contact with the detection indicator sections by the sample fluid. In addition, detection indicator 8104 could also be formed as a discrete element (or plurality thereof) and affixed to the interior surface of the housing any appropriate attachment technology, including for example, but without limitation, an adhesive, or a structural attachment such as a thermal, pressure, or ultrasonic weld.

Because the detection indicator 8104 is affixed to the interior surface of housing 8102, the structures disclosed in connection with earlier-described implementations to retain the detection indicator in the form of a paper strip are not needed. Accordingly, apparatus 8100 does not require the detection openings, sealing member 7216 or support post 7212 of FIG. 72.

A generally tubular exoskeleton 8126 surrounds the housing 8102. Apparatus 8100 further comprises a reference indicator 8130 disposed on or adjacent the exterior surface of the exoskeleton 8126. A reference indicator window 8146 is provided to allow the detection indicator 8104 to be viewed. The reference indicator 8130 may be formed, and may be fixed or attached in place as described in connection with FIGS. 74 and 78.

A detection indicator impregnated or embedded in a matrix or coating, that may be applied or attached to a surface, is not limited in application to a housing 8102 of the type shown in FIG. 81. A detection indicator of this type could also be applied to an interior surface of another device, such as a test tube or a syringe.

The fluid characteristic measurement apparatus disclosed herein can be operated by connecting one end to a source of the fluid to be measured, the opposite end to a syringe or bulb, and using the bulb to draw fluid into the apparatus to saturate the detection indicator. However, it is desirable that the major longitudinal axis of the apparatus be vertical during use to ensure proper saturation of the detection indicator. When bodily fluids are being measured, it is further desirable for personnel to avoid contact with the fluids, and therefore it is desirable to operate the apparatus in a manner that prevents or minimizes leakage of the fluid.

FIG. 82 is a side elevation view of a tee adaptor or right-angle adaptor 8200 which may be used with any of the fluid characteristic measurement apparatus disclosed herein to promote their use in a vertical orientation and minimize leakage of fluids. As one example, nasogastric tubes generally leave the patient in a substantially horizontal orientation. But as earlier disclosed, it is normally preferred that any of the fluid characteristic measurement apparatus disclosed herein be used in a vertical orientation (or nearly so) to optimize coverage and saturation of the detection indicator, thereby providing an accurate measurement of the sample. The tee adaptor 8200 provides an efficient means to connect a horizontally oriented nasogastric tube, or the like, to a fluid characteristic measurement apparatus that is intended to be operated in a vertical orientation. Tee adaptor 8200 comprises a generally tubular body 8210 with a first end 8214, a first end tubing connector 8230 at the first end, a second end 8216, and a second end tubing connector 8234 at the second end. One or more removable, flexible adaptor tubes 8236 may be provided at one or more of the end tubing connectors to allow connection of the tee adaptor 8200 to a wider variety of tube and connector types. The body 8210 defines an interior lumen or conduit 8212 extending from a first end fluid opening 8218 second end fluid opening 8220, allowing fluid flow therethrough from one of the ends to the other.

An accessory port 8222 disposed intermediate the body 8210 and extending generally perpendicular thereto provides a fluid communication channel extending between an accessory port fluid opening 8224 and the interior lumen 8212. The accessory port 8222 may be adapted to receive a tubular member such as an end of a fluid characteristic measurement apparatus, a syringe nose, a needle, or other tube. Although the accessory port 8222 is characterized as extending generally perpendicular to the body 8210, the direction of accessory port 8222 may deviate from perpendicular; it is generally desirable that an accessory such as a fluid characteristic measurement apparatus be operable in a vertical or near vertical orientation when coupled to the port. For non-limiting examples, variations in the shape of the fluid characteristic measurement apparatus or use of the tee adaptor 8200 in applications where the body 8210 is in an orientation substantially different from the horizontal may require that the accessory port 8222 extend form the body 8210 in a direction other than perpendicular to allow the fluid characteristic measurement apparatus to be used in a vertical or near vertical orientation.

A self-closing valve member 8238 may be provided in the channel; the valve member 8238 allows fluid communication through the channel when an end of a fluid characteristic measurement apparatus, syringe nose, or similar tubular member is inserted into the accessory port fluid opening 8224, but automatically closes to prevent fluid communication when the syringe nose or tubular member is not present.

A cap (not shown) or other suitable cover may be provided as an alternative or in addition to the valve member 8238 to prevent communication of fluids, which may include bodily fluids, air, and the like, into or out of the port when no accessory is in use. A manual valve 8226 disposed intermediate the body 8210 allows user control of fluid flow between the second end 8216 and the remainder of the tee adaptor 8200, specifically the first end 8214 and the accessory port 8222. The manual valve 8226 may be operated using a valve handle 8228.

Figure 83:
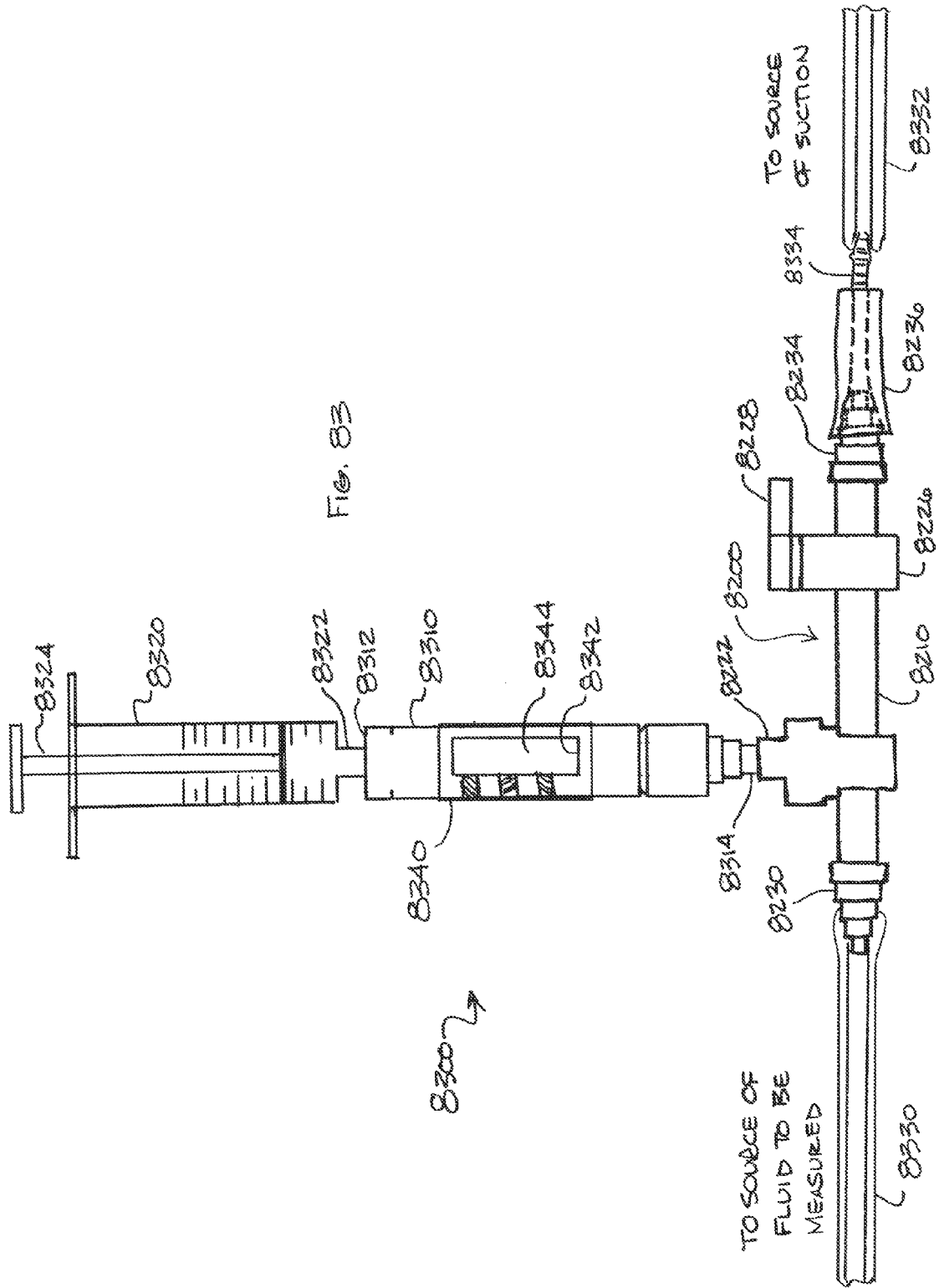
FIG. 83 is a side elevation view of a combination of apparatus for use in obtaining measurements of characteristics of a fluid, such as that which may be obtained through a nasogastric tube which has been inserted into a medical patient.

FIG. 83 is a side elevation view of a combination of apparatus 8300 comprising any of the fluid characteristic measurement apparatus disclosed herein (collectively denoted by reference number 8310), the tee adaptor 8200, and other equipment, for use in obtaining measurements of characteristics of fluid, such as that which may be obtained through a nasogastric tube which has been inserted into a medical patient. The first end tubing connector 8230 of tee adaptor 8200 is connected to a source 8330 of fluid to be measured, such as a nasogastric tube. The second end tubing connector 8234 of tee adaptor 8200 may be connected through flexible adaptor tube 8236 and connector 8334 to tubing 8332 leading to other equipment, such as a source of suction. As will be explained further in detail, the connection of the tee adaptor 8200 to suction allows aspirate to be disposed of, while avoiding leakage of the aspirate or exposure of personnel to the aspirate. The bottom end connector 8314 of fluid characteristic measurement apparatus 8310 is inserted into accessory port 8222 of tee adaptor 8200. A syringe 8320 is coupled to fluid characteristic measurement apparatus 8310 by inserting its fluid port 8322 into the top end port 8312 of the apparatus 8310. Plunger 8324 may be raised to aspirate fluid from fluid source tube 8330 into fluid characteristic measurement apparatus 8310. When aspirated, the fluid saturates the detection indicator 8344. The detection indicator 8344 may be compared to reference samples of reference indicator 8340 by viewing it through reference indicator window 8342. The tee adaptor 8200 may be reused for multiple measurements by connecting a new fluid characteristic measurement apparatus, e.g., using the accessory port 8222, for each measurement. The user of the tee adaptor 8200, and its reuse for multiple measurements, may help retain bodily fluids within the adaptor, fluid characteristic measurement apparatus and related accessories and tubing, thereby helping to avoid exposure of personnel to bodily fluids.

Figure 84:
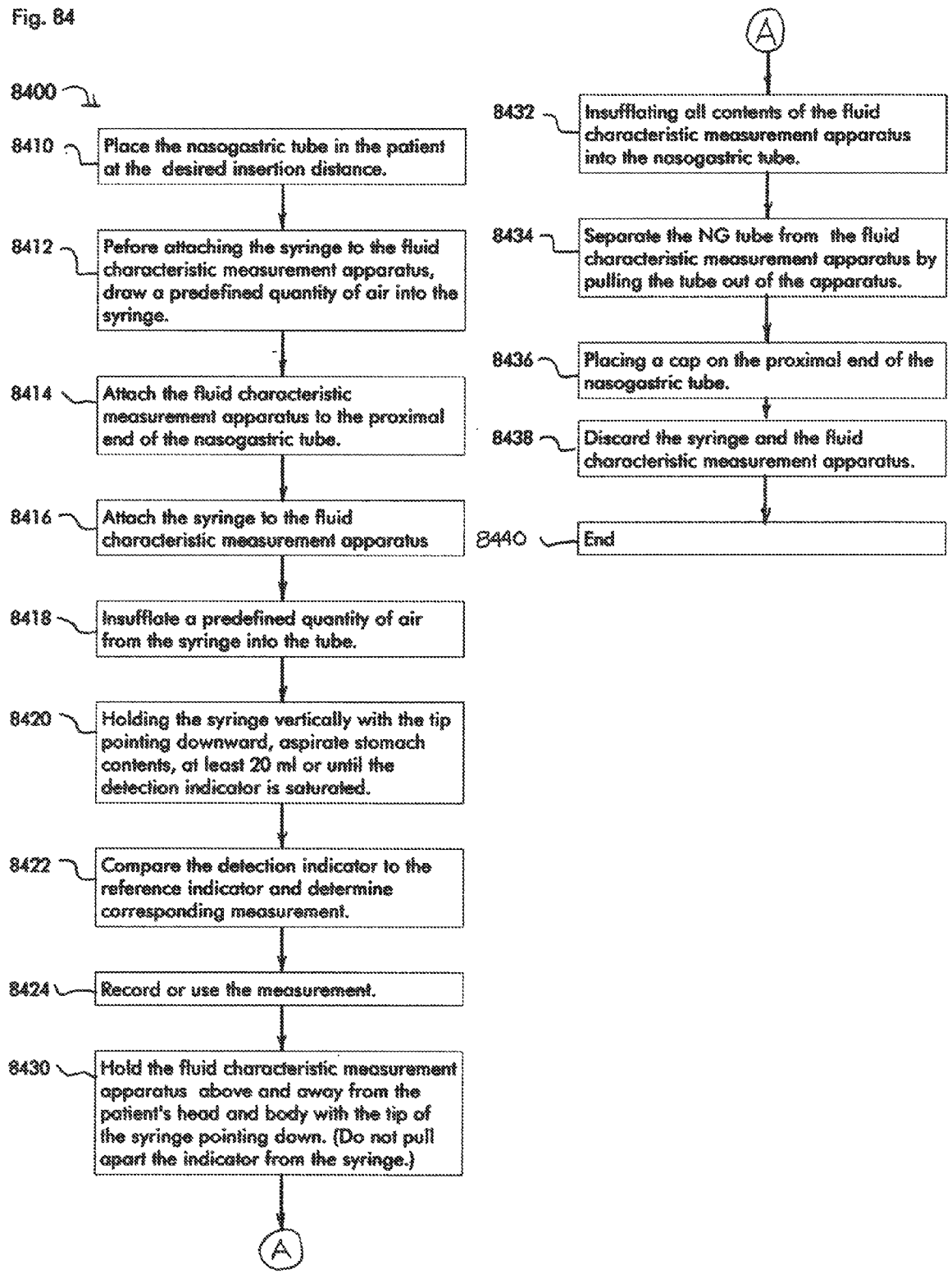
FIG. 84 is a flow diagram showing a method which may be used in conjunction with any of the fluid characteristic measurement apparatus disclosed herein to measure a characteristic of a fluid, such as that which may be obtained through a nasogastric tube which has been inserted into a medical patient.
Figure 67:
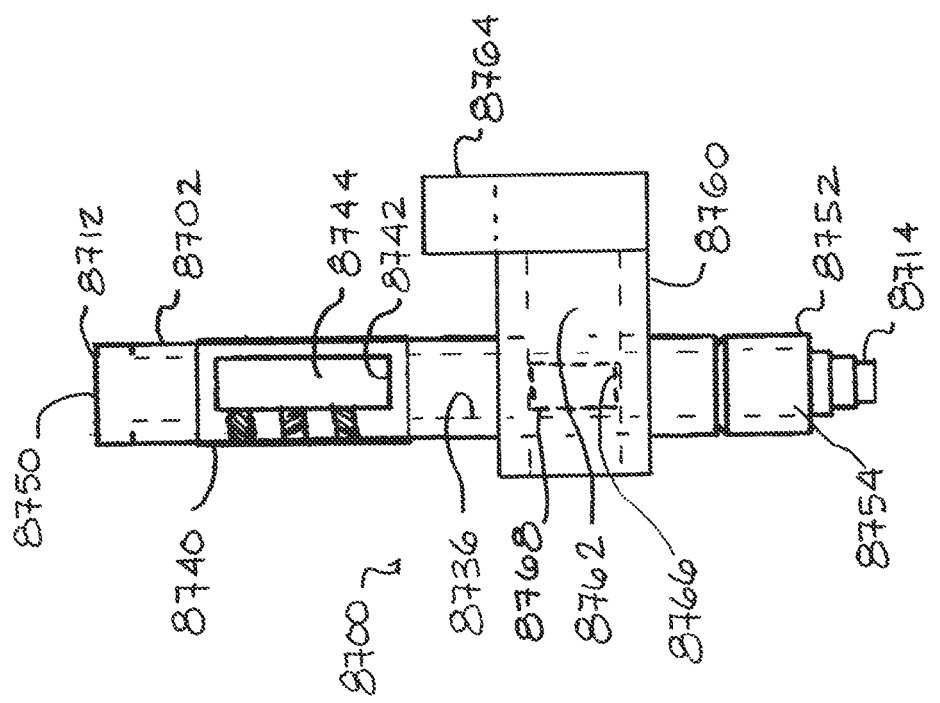

FIG. 84 is a flow diagram showing a method 8400 which may be used in conjunction with any of the fluid characteristic measurement apparatus disclosed herein to measure a characteristic of a fluid, such as that which may be obtained through a nasogastric tube which has been inserted into a medical patient. A syringe is used to aspirate fluid through the fluid characteristic measurement apparatus.

The method begins in step 8410, in which the user places the nasogastric tube in the patient at the desired insertion distance.

In step 8412, before attaching the syringe to the fluid characteristic measurement apparatus, the user draws a predefined quantity of air into the syringe for subsequent insufflation into the nasogastric tube to ensure that the distal end of the tube is not in contact with the stomach wall. An appropriate quantity of air drawn into the syringe may depend on the size of the patient, and, for example, may be about 10 ml for adults, 5 ml for children, and 1 ml infants. However, other quantities of air may be used as required by the particular circumstances in which the procedure is conducted.

In step 8414, the user attaches the fluid characteristic measurement apparatus to the proximal end of the nasogastric tube.

In step 8416, the user attaches the syringe to the fluid characteristic measurement apparatus.

In step 8418, the user insufflates a predefined quantity of air from the syringe into the nasogastric tube. This ensures that the distal end of the nasogastric tube is not in contact with the stomach wall. An appropriate quantity of air may depend on the size of the patient, and, for example, may be about 10 ml for adults, 5 ml for children, and 1 ml infants. However, other quantities of air may be used as required by the particular circumstances in which the procedure is conducted.

In step 8420 the user holds the syringe vertically with the tip pointing downward, and aspirates stomach contents, at least 20 ml or until the detection indicator is saturated.

In step 8422, the user compares the detection indicator to the reference indicator and determines corresponding measurement.

In step 8424, the user records or otherwise uses the measurement. For example, if the fluid characteristic measurement apparatus is configured to show correct placement of a nasogastric tube, the detection indicator is configured to match the reference indicator when the pH of the aspirate is less than 4. Thus, if the aspirate does not change the detection indicator to show the reference color, then the pH is not less than 4, and the tube may be misplaced. For another example, the detection indicator may also be configured to exhibit an appearance, e.g., a color, that can be compared to the reference indicator to establish a specific pH measurement of the fluid (subject to the resolution and range of the reference indicator). This measurement can guide a clinician in medical management of the patient. After medications are adjusted, a new detection indicator can be used with the same adapter in similar fashion to again measure the pH value of the aspirate. These are merely example ways in which the measurement can be used, and the measurements could be used in other appropriate ways. Also, characteristics other than pH could also be measured and used.

Steps 8430 through 8438 are directed to removal of the fluid characteristic measurement apparatus from the nasogastric tube. In step 8430, the user holds the fluid characteristic measurement apparatus above and away from the patient's head and body with the tip of the syringe pointing down. To avoid spillage, the fluid characteristic measurement apparatus should not be separated from the syringe.

In step 8432, which is optional, the user employs the syringe to insufflate all of the contents of the fluid characteristic measurement apparatus through the nasogastric tube and into the patient. Air at the top of the syringe will flush liquid from the syringe and the fluid characteristic measurement apparatus. Flushing the fluid characteristic measurement apparatus will prevent leakage of bodily fluids during the disconnection of the fluid characteristic measurement apparatus from the nasogastric tube.

In step 8434, the user separates the nasogastric tube from the fluid characteristic measurement apparatus by pulling the tube out of the apparatus.

In step 8436, which is optional, the user may place a cap on the proximal end of the nasogastric tube. This helps prevent leakage of bodily fluids.

In step 8438, which is optional, the user discards the syringe and the fluid characteristic measurement apparatus.

The method ends at 8440.

When removing the pH indicator from the NG tube as described in steps 8430-8434, it is typical that gastric fluid spills out. In comparison testing with water and gastric fluid, more spillage occurs with gastric fluid than with water. This may be because mucous that accompanies the gastric fluid is thicker than water, and as a result, both the mucous and gastric fluid in the fluid characteristic measurement apparatus is pulled out by gravity and by the adhesive force of the mucous and gastric fluid in the nasogastric tube.

FIG. 85 is a flow diagram showing a method 8500 which may be used in conjunction with the apparatus of FIGS. 82-83, including any of the fluid characteristic measurement apparatus disclosed herein, and an adaptor, such as the tee adaptor 8200, to measure a characteristic of a fluid, such as that which may be obtained through a nasogastric tube which has been inserted into a medical patient. The steps of method 8500 reduce the likelihood of spillage or leakage of bodily fluids and exposure of personnel to bodily fluids.

The method begins at step 8510, in which the user attaches the first end tubing connector 8230 of the tee adaptor to the nasogastric tube and closes the manual valve. The user also ensure the cap is on the accessory port. This step helps avoid spilling gastric fluid out of the nasogastric tube during its insertion into the patient.

In step 8512, the user places the nasogastric tube in the patient at the desired insertion distance.

In step 8514, before attaching the syringe to the fluid characteristic measurement apparatus, the user draws a predefined quantity of air into the syringe for subsequent insufflation into the nasogastric tube to ensure that the distal end of the tube is not in contact with the stomach wall. An appropriate quantity of air drawn into the syringe may depend on the size of the patient, and, for example, may be about 10 ml for adults, 5 ml for children, and 1 ml infants. However, other quantities of air may be used as required by the particular circumstances in which the procedure is conducted.

In step 8516, the user attaches the syringe to the fluid characteristic measurement apparatus.

In step 8518, the user removes the cap from the tee adaptor accessory port and inserts the fluid characteristic measurement apparatus and syringe into the accessory port.

In step 8520, the user insufflates a predefined quantity of air from the syringe into the nasogastric tube. This ensures that the distal end of the nasogastric tube is not in contact with the stomach wall. An appropriate quantity of air may depend on the size of the patient, and, for example, may be about 10 ml for adults, 5 ml for children, and 1 ml infants. However, other quantities of air may be used as required by the particular circumstances in which the procedure is conducted.

In step 8522, the user holds the fluid characteristic measurement apparatus vertically and aspirates fluid from the nasogastric tube until the detection indicator is saturated. During aspiration, all of the air that was in the nasogastric tube will be drawn into the syringe and there will be about 20-30 cc of air at the top by the plunger.

In step 8524, the user compares the detection indicator to the reference indicator and determines the corresponding measurement.

In step 8526, the user records or otherwise uses the measurement. For example, if the fluid characteristic measurement apparatus is configured to show correct placement of a nasogastric tube, the detection indicator is configured to match the reference indicator when the pH of the aspirate is less than 4. Thus, if the aspirate does not change the detection indicator to show the reference color, then the pH is not less than 4, and the tube may be misplaced. For another example, the detection indicator may also be configured to exhibit an appearance, e.g., a color, that can be compared to the reference indicator to establish a specific pH measurement of the fluid (subject to the resolution and range of the reference indicator). This measurement can guide a clinician in medical management of the patient. After medications are adjusted, a new detection indicator can be used with the same adapter in similar fashion to again measure the pH value of the aspirate. These are merely example ways in which the measurement can be used, and the measurements could be used in other appropriate ways. Also, characteristics other than pH could also be measured and used.

Steps 8528 through 8538 are directed to disconnection and removal of the fluid characteristic measurement apparatus from the tee adaptor.

In step 8528, while leaving the fluid characteristic measurement apparatus undisturbed in the accessory port, the user attaches the second end tubing connector to suction.

In step 8530, the user turns on the suction at the source and opens the manual valve on the tee adaptor. In one example, the manual valve is operated (e.g., step 8510) to disable suction before the conduit is coupled to the suction source.

In step 8532, the user insufflates the contents of the syringe and fluid characteristic measurement apparatus into the tee adaptor. Because the tee adaptor is attached to suction, the bodily fluids will not return to the patient, and instead may be drawn into a suction canister associated with the suction source. In addition, air in the top of syringe will completely flush the bodily fluids and gastric aspirate from the fluid characteristic measurement apparatus and syringe.

In step 8534, the user removes the fluid characteristic measurement apparatus and syringe as one unit from the tee adaptor and discard them. Because the bodily fluids and gastric aspirate have been flushed out of the fluid characteristic measurement apparatus and syringe, there is no spillage.

In step 8536, the user places the cap over the tee adaptor accessory port.

The method ends at 8538.

In some situations, it may be desirable to make an initial measurement of a characteristic of a bodily fluid to determine whether treatment is necessary, provide an appropriate treatment or therapy, and then recheck a characteristic to determine whether the treatment has been effective. For example, the pH of a patient's gastric aspirate may be initially measured to determine that treatment is needed. After treatment has been provided to adjust the pH, the pH may be measured again to determine if the pH has changed in a desirable way.

Figure 88:
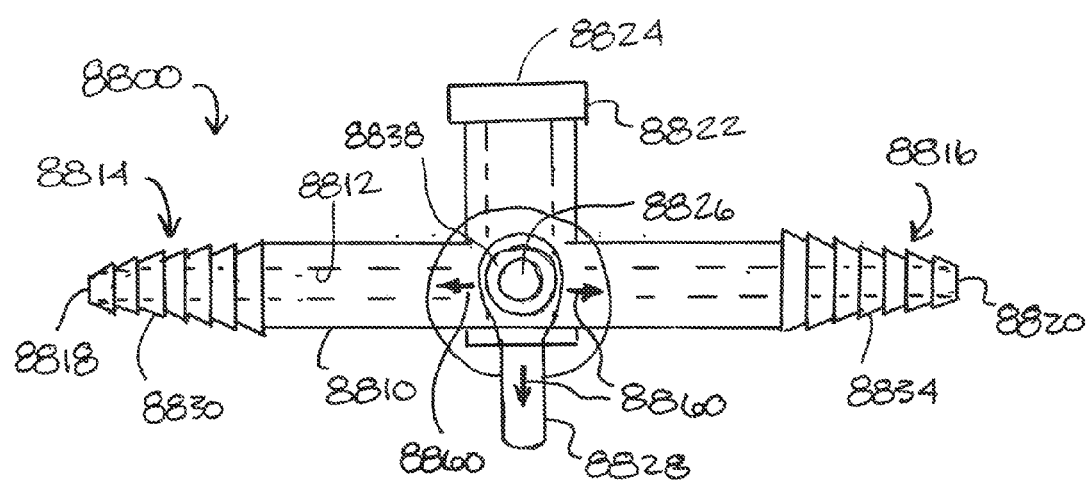
FIG. 88 is a side elevation view of a further implementation of a tee adaptor which may be used with any of the fluid characteristic measurement apparatus disclosed herein.

If apparatus similar to that of FIG. 82-83 or 88, is being used, the user may perform another measurement on the same patient by obtaining a new fluid characteristic measurement apparatus and a new syringe, and repeating steps 8514 through 8536. The user would close the stop-cock and attach a new fluid characteristic measurement apparatus and syringe and aspirate to saturate the detection indicator. After the measurement, the user may open the manual valve to suction, insufflate, remove the fluid characteristic measurement apparatus and syringe, and replace the accessory cap. Where a fluid characteristic measurement apparatus is used without apparatus similar to that of FIG. 82-83 or 88, e.g., the fluid characteristic measurement apparatus is directly connected to a nasogastric tube, repeat measurements can be accomplished by obtaining a new fluid characteristic measurement apparatus and a new syringe, and repeating steps 8412 through 8434.

One application of repeated testing is in optimizing the pH of aspirate so as to minimize ulcers, bleeding and pneumonia. Maintaining the pH of gastric aspirate above 4 will inhibit gastric stress ulcers and bleeding. However, raising the pH of gastric aspirate can increase the chances of pneumonia in critically ill patients. Because of this, tightly controlling the pH of gastric aspirate at a level high enough to inhibit gastric ulcers and bleeding but low enough to allow some inhibition of gastric colonization is desirable. It is possible that a pH level of 4 would be high enough to decrease bleeding, but low enough to inhibit bacterial growth of the stomach that may aid in an increase the incidence of pneumonia. Tightly controlling the pH of gastric aspirate could be performed by regularly checking the pH of aspirate and adjusting medications. The use of a removable and disposable fluid characteristic measurement apparatus can allow repeated measurements to be conducted efficiently with minimum risk of exposure of personnel to bodily fluids.

In another application of repeated measurement, it may be desirable to make an initial measurement to quickly ascertain that a threshold condition has been satisfied, and then make one or more additional measurements, such as measurements that may be more specific than the initial measurement. For example, the initial measurement may be used to detect gastric aspirate having a pH of around 4, indicating correct placement of a nasogastric tube in a patient's stomach. The subsequent measurement may be used measure the pH specifically, to determine whether treatment to adjust the gastric fluid pH is required, or earlier treatment has been successful. This may be accomplished by using different fluid characteristic measurement apparatus, each adapted to provide the desired measurement, along with a new syringe for each measurement, and repeating steps 8412 through 8434 where direct connection of the fluid characteristic measurement apparatus to a nasogastric tube is employed, or steps 8514 through 8536 where apparatus similar to that of FIG. 82-83 or 88 are used.

FIG. 86 is a flow diagram depicting a partial method 8600 for manufacturing a fluid characteristic measurement apparatus of the type generally shown in FIGS. 74 and 78. The method is not limited to the apparatus 7400, but could be used to manufacture other similar fluid characteristic measurement apparatus.

The method begins in step 8610, in which the manufacturer prepares a reference indicator calibrated to match the characteristics of the detection indicator which will be used with the apparatus. It is known that the response of various types of detection indicator media varies from manufacturer to manufacturer and lot to lot. For many types of detection indicators, in order to ensure that the measurements are as accurate as possible, it is necessary to test the detection indicator media for each separate manufacturing lot, and responsively prepare a reference indicator calibrated to match the response of the media produced in that lot. Other factors, such as time or temperature, can also affect the behavior of the certain detection indicator media, and therefore, some events or conditions may necessitate testing of the media and preparation of a calibrated reference indicator even for instances of media from the same manufacturing lot. This step is optional, because some detection indicator media may not require such calibration. For example, if the media is highly sensitive and the response of the media is unambiguous, or the media is extremely stable, or the user does not require an exact measurement result, calibration may be unnecessary.

In step 8612, an adhesive is applied to predetermined locations of the sealing member so as to receive and affix the detection indicator in a preferred location and orientation, such that when the sealing member is wrapped around the body of the fluid characteristic measurement apparatus, the detection indicator will be in the correct position for use. Applying the adhesive to the sealing member before the detection indicator is placed reduces pooling of the adhesive, which may improve the quality of the reading because the detection indicator will more likely be uniformly saturated. It also allows better positioning for manufacture. However, the adhesive could also be applied to the detection indicator alone, or to both the detection indicator and the sealing member. Moreover, step 8612 could be performed in a different sequence. For example, an adhesive may be applied to the detection indicator when the indicator medium is manufactured. Further, step 8612 is optional, and could be replaced by step 8612a, discussed further below, or the assembly operation may be performed without an adhesive or other attachment of the detection indicator to the sealing member. In that case, the detection indicator may simply be mechanically captured by the sealing member.

In step 8614, a piece of detection indicator media which has been formed to the correct size and shape is applied to the sealing member at the preferred location and orientation.

Alternately, steps 8612a and 8614a may be substituted for steps 8612 and 8614. In step 8612a, a light or partial vacuum is applied to one end of the apparatus in communication with the central lumen. In step 8614a, a piece of detection indicator media which has been formed to the correct size and shape is placed in a final desired location covering the detection openings. The pressure created by the vacuum applied to the central lumen holds the detection indicator media in place until the sealing member is wrapped in step 8618. The partial vacuum also assists in removing any bubbling in the sealing member when adhered to the housing 7202. Such bubbling could affect the clarity of housing and interfere with or introduce error into the reading. Once the sealing member is wrapped, vacuum may be removed.

In step 8616, an adhesive or sealant is applied to adhesive retaining channels of the housing of the fluid characteristic measurement apparatus. This step is optional, because the seal may formed using other means, for example but without limitation, thermal, pressure, or ultrasonic welding.

In step 8618, the sealing member is wrapped circumferentially around the body, placing the detection indicator in the correct position for use. Any required attachment or sealing operations are performed.

In step 8620, the exoskeleton is telescoped over the body and any required attachment or sealing operations are performed.

In step 8622, the exoskeleton retaining ring is applied to the body and any required attachment or sealing operations are performed.

The method ends at 8624.

FIG. 87 is a side elevation view of a further implementation of a fluid characteristic measurement apparatus 8700 in which certain components are arranged in an alternate configuration. The apparatus 8700 may generally be constructed in a manner similar to the apparatus 7200 of FIGS. 72-73 and 75, with certain variations from that construction noted hereinbelow. Accordingly, structures and features not specifically mentioned in connection with apparatus 8700 may be constructed or implemented in a manner similar to like structures and features of the apparatus 7200 of FIGS. 72-73 and 75. As best seen in FIG. 87, apparatus 8700 comprises a housing 8702 forming a generally tubular body, with a top end port 8712 having a first opening 8750 and a bottom end port 8752 having a second opening 8754 connected by a central lumen 8736 for fluid communication therethrough. A bottom end connector 8714, which may be, for example, a barb or adaptor, may be provided to couple the second opening 8754 to a nasogastric tube, adaptor, or other accessory. 8700 further comprises a detection indicator 8744 and a reference indicator 8740. Reference indicator 8740 has a reference indicator window 8742 through which the detection indicator 8744 is visible.

Apparatus 8700 further comprises a manually operated valve or stop-cock 8760 which controls fluid communication through central lumen 8736. Valve 8760 comprises a generally tubular valve journal 8766, in which a valve pintle 8762 is mounted for rotation about an axis perpendicular to the longitudinal axis of central lumen 8736. The pintle 8762 extends through the central lumen 8736. A handle 8764 attached to the pintle allows the pintle to be rotated. An aperture 8768 through the pintle is aligned with the central lumen 8736. In an "open" position, the pintle aperture 8768 joins opposite sides of the central lumen 8736 to allows fluid communication therethrough. In a "closed" position about 90 degrees of rotation from the "open" position, the pintle walls block the opposite sides of the central lumen, stopping fluid communication therethrough. In use, the valve 8760 may be closed to prevent fluid flow, for example, when the apparatus 8700 is being disconnected from a nasogastric tube or an adaptor thereto, thereby avoiding leakage of bodily fluids which have been drawn into the adaptor.

FIG. 88 is a side elevation view of a further implementation of a tee adaptor or right-angle adaptor 8800 which may be used with any of the fluid characteristic measurement apparatus disclosed herein to promote their use in a vertical orientation and minimize leakage of fluids. The adaptor 8800 is similar to that described in Lopez U.S. Pat. Nos. 4,790,832 and 4,895,562 and comprises a generally tubular body 8810 extending from a first end 8814 to a second end 8816. The body 8810 defines an interior lumen 8812 connecting a first end fluid opening 8818 at the first end 8814 to a second end fluid opening 8820 at the second end 8816. The first end may comprise a first end tubing connector 8830 for coupling tubing to the body 8810. The second end may comprise a second end tubing connector 8834 for coupling tubing to the body 8810. Either of these connectors 8830 and 8834 may be shaped in the form of a barb with appropriate ridges to securely engage the tubing. Alternatively, the connections may have other shapes appropriate for connection to tubing, adaptors, or accessories. Additional adaptors may also be used.

An accessory port 8822 is provided at an intermediate location along the body 8810 and extends generally perpendicular to the body 8810. The accessory port 8822 has an accessory port fluid opening 8824 providing a channel extending toward the interior lumen 8812. The accessory port 8822 may be adapted to receive a tubular member such as an end of a fluid characteristic measurement apparatus, a syringe nose, a needle, or other tube. Although the accessory port 8822 is characterized as extending generally perpendicular to the body 8810, the direction of accessory port 8822 may deviate from perpendicular; it is generally desirable that an accessory such as a fluid characteristic measurement apparatus be operable in a vertical or near vertical orientation when coupled to the port. For non-limiting examples, variations in the shape of the fluid characteristic measurement apparatus or use of the tee adaptor 8800 in applications where the body 8810 is in an orientation substantially different from the horizontal may require that the accessory port 8822 extend form the body 8810 in a direction other than perpendicular to allow the fluid characteristic measurement apparatus to be used in a vertical or near vertical orientation.

A manual valve is provided to control fluid communication among the accessory port and the portions of the interior lumen 8812 on either side of the valve. The two sides of the interior lumen 8812 and the accessory port fluid opening 8824 form a inverted-tee-shaped body channel intersecting at the valve 8826. The valve comprises a valve handle 8828 connected to a valve member or pintle 8838 which extends into and interrupts the channel intersection. The valve member has a tee-shaped channel that is generally aligned with the tee-shaped channel formed by the interior lumen 8812 and the accessory port fluid opening 8824.

The valve member 8838 is rotatable using the valve handle 8828 such that the various openings of the tee-shaped valve member channel are presented to the several legs of the tee-shaped body channel. It will be appreciated that the side of the valve member opposite the stem of the tee (the "blocking side") blocks fluid communication from that leg of the body channel to which it is presented. If the valve is rotated such that the three openings of the valve member are aligned with the three legs of the body channel, the blocking side faces none of the legs of the body channel, and three-way communication of fluid is permitted between all three legs of the body channel—the two sides of the interior lumen 8812 and the accessory port fluid opening 8824. If the valve is rotated into any other position, the blocking side of the valve member blocks fluid communication through the one leg of the body channel which it faces, and two-way fluid communication is permitted among the other two legs. Valve position indicia 8860 on the valve handle 8828 inform the user as to which legs of the body channel are connected for fluid communication; fluid communication is permitted among those legs of the body channel with which the arrows are aligned.

The tee adaptor 8800 may, for example, be used as an alternative to the tee adaptor 8200 in the configuration of FIG. 83. The first end tubing connector 8830 may be connected to a nasogastric tube which has been placed in a patient. The second end tubing connector 8834 may be connected to a suction source or tube. Any of the fluid characteristic measurement apparatus may be connected to accessory port 8822. A method similar to method 8600 of FIG. 86 may be used to operate equipment in this configuration to collect a sample of gastric fluid in the fluid characteristic measurement apparatus, take a measurement of a fluid characteristic, and remove and dispose of the used fluid characteristic measurement apparatus in a way that avoids leakage of bodily fluids and exposure of personnel thereto.

Figure 90:
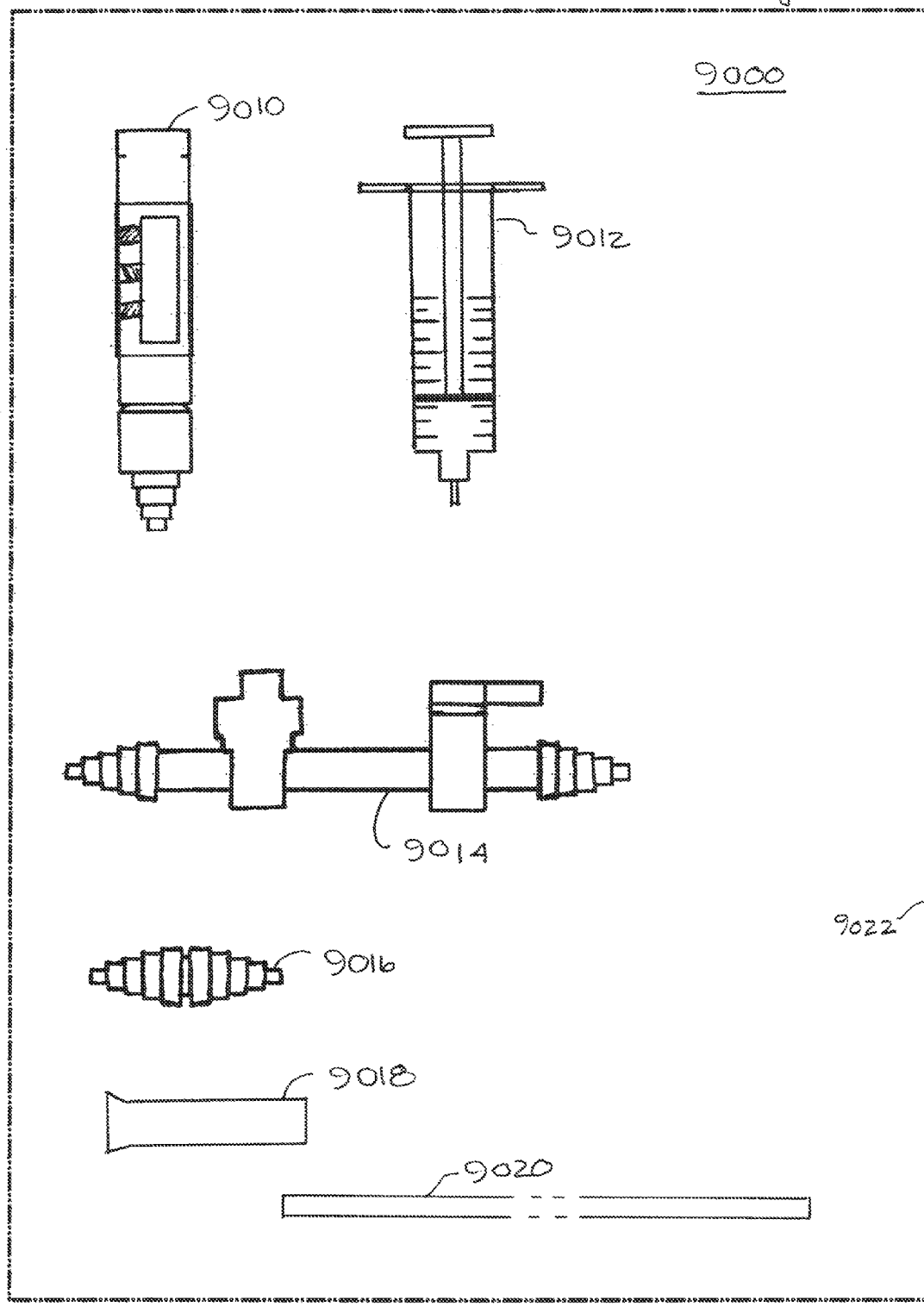
FIG. 90 depicts a system of components, including a fluid characteristic measurement apparatus, that may be supplied together for cooperative use in measurement and detection.

Any of the fluid characteristic measurement apparatus disclosed herein may be supplied with other components as a kit, group, or system thereof to aid personnel in rapid and correct deployment of the fluid characteristic measurement apparatus, thereby enabling personnel to perform measurements or detections quickly and accurately, possibly improving patient outcomes. FIG. 90 depicts one implementation of a system 9000 of components that may be supplied together for cooperative use in measurement and detection. System 9000 comprises at least one fluid characteristic measurement apparatus 9010, which may be implemented, for example, as any of the fluid characteristic measurement apparatus described herein, including a detection indicator configured to display at least one visual indication when in contact with a body fluid, which indication represents a value of a characteristic of the body fluid. System 9000 may further comprise additional components to facilitate deployment of fluid characteristic measurement apparatus 9010. For example, system 9000 may further comprise a syringe 9012, which may be used to aspirate and insufflate fluids. System 9000 may further comprise a right angle or tee adaptor 9014, which may be implemented using one of the tee adaptors 8200 of FIG. 82 or 8800 of FIG. 88. Other adaptors could also be used. System 9000 may also comprise one or more adaptors for connecting fluid characteristic measurement apparatus 9010, syringe 9012, or right-angle adaptor 9014 to tubing or other accessories. For example, system 9000 may comprise a barb adaptor 9016, and a flexible tubing adaptor 9018, or several of them, which may be used to couple components of the system 9000 to other tubing and accessories. System 9000 may further comprise one or more lengths 9010 of a flexible tubing. The components of system 9000 may be supplied in a container, here represented by line 9022, which may be implemented using any suitable container, such as a bag, pouch, or box. Furnishing components as a kit ensures compatibility of the components with one another, and reduces the probability of delay that might otherwise occur if personnel were required to collect these separate items prior to a detection or measurement procedure.

FIG. 91 is a side elevation view of a further implementation of a fluid characteristic measurement apparatus 9100 in which certain components are arranged in an alternate configuration. The apparatus 9100 may generally be constructed in a manner similar to the apparatus 7200 of FIGS. 72-73 and 75, with certain variations from that construction noted hereinbelow. Structures and features not specifically mentioned in connection with apparatus 7400 may be constructed or implemented in a manner similar to like structures and features of the apparatus 7200 of FIGS. 72-73 and 75. As best seen in FIG. 91, apparatus 9100 comprises a first body portion 9150 and a second body portion 9170 adapted to mate with the first body portion 9150. The first body portion 9150 has a first end 9152 with a first end opening 9154 and a second end 9156 with a second end opening 9158. The first end opening 9154 and second end opening 9158 are joined by a central lumen 9136 for fluid communication therethrough. As best seen in FIG. 91, the first end 9152 may be adapted for connection to tubing, an accessory, or other apparatus. For example, first end 9152 may be implemented as a barb fitting. However, other structures could also be used, and first end 9152 could further comprise an appropriate adaptor to broaden the range of devices and tubings to which the first end 9152 may be coupled.

First body portion 9150 comprises a detection indicator 9104, disposed in the interior of the body, and a reference indicator 9130, both of which are arranged so as to be juxtaposed, optically adjacent or otherwise easily visually inspected and compared. As best seen in FIG. 91, there is shown an example configuration of detection indicator 9104 and reference indicator 9130 in which reference indicator 9130 is wrapped circumferentially around the first body portion 9150, and a reference indicator window 9146 is provided through which detection indicator 9104 may be inspected and compared to indicia of reference indicator 9130. Reference indicator window 9146 may be constructed, for example, as a region of optically transparent or translucent material as a region from which material is omitted to form an aperture. At least a portion of first body portion 9150 is optically transparent or translucent to permit inspection of the detection indicator 9104 therethrough.

An interior chamber 9106 is provided in first body portion 9150 to house the detection indicator 9104. The interior chamber 9106 is in fluid communication with central lumen 9136 and may, for example but without limitation, be implemented as an enlargement or gallery thereof, and may comprise or be defined by one or more structures to retain the detection indicator 9104 in a desired position while permitting fluid communication with the central lumen 9136 and allowing saturation of the interior chamber 9106 when fluid is present in the central lumen. The detection indicator 9104 may be implemented using any of the structures, features and materials described herein in connection with detection indicators. The detection indicator 9104 is configured to display or exhibit at least one visual indication, appearance or other externally detectable manifestation that is responsive to the fluid characteristic or characteristics being measured by the apparatus 9100. For examples but without limitation: the detection indicator 9104 may respond when in contact with the fluid; the fluid may be a body fluid; and more particularly, the body fluid may be a liquid, such as gastric aspirate from a medical or veterinary patient. In an unmated configuration of first body portion 9150 and second body portion 9170, the detection indicator 9104 may be installed into interior chamber 9106 through second end opening 9158 of first body portion 9150. Thus, interior chamber 9106 may form a receptacle for receiving and housing the detection indicator 9104. Several different respective configurations of the detection indicator 9104, interior chamber 9106, reference indicator 9130, and structural components of the first body portion 9150 may be used. For example, first body portion 9150 may comprise a housing and exoskeleton similar to those of apparatus 7200, in which case the configurations of FIGS. 75, 78, 79, 80, and 81, or similar configurations, could be used.

In another implementation, first body portion 9150 may comprise a tubular member that functions as both the housing and exoskeleton of apparatus 7200. FIG. 92 depicts an example of such an implementation in a simplified cross-section view taken across the major longitudinal axis of the first body portion 9150 showing the relative placement of the tubular member 9210, the interior chamber 9106, the central lumen 9136, the detection indicator 9104, the reference indicator 9130, the reference indicator window 9146, and a detection indicator retaining member 9212. Detection indicator retaining member 9212 may be formed, for example, as a panel or plate-like structure extending across a portion of the interior wall or surface of the tubular member 9210 to define interior chamber 9106. The detection indicator retaining member 9212 may extend across points on the interior wall, substantially parallel to the longitudinal axis of the tubular member. Openings in detection indicator retaining member 9212 allow fluid communication among the interior chamber 9106 and central lumen 9136. The openings may, for example, be formed as holes, slots, or the like. Detection indicator retaining member 9212 could also be formed as a mesh. A floor may be provided in the interior chamber 9106 to retain detection indicator 9104 in a preferred longitudinal position within the interior chamber 9106. The floor may be solid, or may be a perforated, comb, mesh, or similar structure to promote fluid communication among the interior chamber 9106 and central lumen 9136.

FIG. 93 depicts a further example of an implementation of first body portion 9150 in a simplified cross-section view taken across the major longitudinal axis thereof showing the relative placement of the tubular member 9310, the interior chamber 9106, the central lumen 9136, the detection indicator 9104, the reference indicator 9130, the reference indicator window 9146, and a detection indicator retaining member 9312. Detection indicator retaining member 9312 may be constructed, for example, as a curved structure extending from the interior surface or wall of the tubular member and running along the interior surface or wall, thereby defining interior chamber 9106 as a curved slot near and conforming generally to the interior wall of the tubular member 9310. As in FIG. 92, interior chamber 9106 may be provided with a floor, and both the detection indicator retaining member 9312 and the floor may have apertures or other construction to promote fluid communication among interior chamber 9106 and central lumen 9136.

In other implementations, the detection indicator may be formed as a coating on a surface of the interior chamber 9106 or applied adhesively to a surface of interior chamber 9106, in which cases the detection indicator retaining structures may be omitted from interior chamber 9106, and interior chamber 9106 may be coextensive with at least a portion of central lumen 9136. FIG. 81 depicts an implementation where the detection indicator is applied to an interior surface of the housing, and the reference indicator is applied to the exterior surface of the exoskeleton. In an implementation where a tubular member functions as both the housing and exoskeleton, the detection indicator 9104 analogously could be applied to an inside surface of the tubular member, and the reference indicator 9130 analogously could be applied to the exterior surface of the tubular member.

Returning to FIG. 91, second body portion 9170 comprises a third end 9172 with a third end opening 9174 and a fourth end 9176 with a fourth end opening 9178. Third end opening 9174 and fourth end opening 9178 are joined by a central lumen for fluid communication therethrough. The fourth end 9176 of second body portion 9170 is adapted to mate with the second end 9156 of first body portion 9150. When the second body portion 9170 is mated with the first body portion 9150, central lumen 9136 allows fluid communication therethrough between first end opening 9154 and third end opening 9174. In addition, when mated, the second body portion 9170 may retain the detection indicator 9104 in interior chamber 9106. The mating may be facilitated by structural features, such as a section of reduced diameter on the second body portion 9170 which telescopes a distance into the first body portion 9150. An attachment or retaining structure 9182, which may be constructed, for example, as a thread or lip, may be provided to secure second body portion 9170 to first body portion 9150. A complementary structure may be provided on first body portion 9150. Other structures and arrangements thereof could also be used. For example, the section of reduced diameter may be provided on first body portion 9150 to telescope into second body portion 9170, or the two components may be abutted. Whether or not a structural attachment feature is provided, second body portion 9170 may be to first body portion 9150 using any appropriate attachment technology, including for example, but without limitation, an adhesive, or a structural attachment such as a thermal, pressure, or ultrasonic weld. Sealing Surface 9160 and sealing surface 9180 may be provided on first body portion 9150 and second body portion 9170, respectively, to receive a sealing component or treatment. For non-limiting example, the sealing component or treatment may be an O-ring, a sealant or adhesive, or an appropriate treatment that has the effect of forming a seal between the two components, such as ultrasonic, pressure, thermal, or chemical welding.

While reference has been made to measuring pH of gastric aspirate, any of the detection indicators disclosed herein could be configured for alternate measurements or detection using an indicating medium or apparatus that can be inspected from outside the measurement apparatus by a user or instrument. For example but without limitation, the detection indicator could detect or measure one or more of temperature, carbon dioxide, alkalinization, proteins, enzymes, chemicals, other biological agents or detectable components, or any other characteristics of bodily fluids or materials, in addition to or instead of gastric aspirate, such as blood, urine, or any other bodily fluids or tissue, including gases, vapors, air, and the like. For example but without limitation, a detection indicator could measure or detect the presence, amounts, concentrations, levels, or the like, of certain proteins in a sample. In one example, the detection indicator would change in color at a certain level of a protein in a blood sample, which could be collected using ordinary phlebotomy procedures and placed in a test tube for measurement. The detection indicator could, for example, respond to the presence of a protein such as kinase, myoglobin, troponin, or other cardiac muscle proteins which may indicate that the patient is suffering from a heart attack or other heart muscle injuries (e.g., microinfarctions). Other proteins, possibly found in bodily fluids other than blood, such as pepsin or bilirubin, could also be detected or measured. Also, the measured or detected sample may be collected from other bodily fluids, such as urine.

Although specific examples of detection indicators and indicator media have been disclosed herein, any indicator media appropriate to the sample and the characteristic to be measured could also be used. For example, if temperature is the characteristic to be measured, the indicator media could be a strip of temperature-indicating film bearing a liquid crystal material that displays a color corresponding to temperature. Other indicator media could also be used.

Moreover, although the examples disclosed herein contemplate ordinary visual inspection, by a human user, of a color or other appearance change in an indicator medium, the measurement or detection could also be performed or facilitated by external devices or instruments, such as where the change in the indicator medium is invisible or difficult for a human observer to accurately discern. For example, a measurement might require that the sample or an indicator medium be illuminated by ultra-violet light. For another example, a measurement might be performed by an instrument that senses the color of an indicator medium and records, displays, or otherwise signals a corresponding measurement result, rather than relying on the user's visual perception of the state of the indicator medium or a change therein.

The examples described above generally relate to human patients. Accordingly, various features such as the size and shape of the apparatus, range of pH or other fluid measurement criteria, related accessories, and their configuration are selected to promote their use with a human patient. Additionally, steps and/or methods are selected and/or adapted for use with human patients. In alternative implementations, the above-mentioned features may be selected to promote their use with non-human patients such as animals, including mammals, reptiles, amphibians, birds, fish, and invertebrates. As one example, a veterinarian at a zoo or clinic may take on the role of the practitioner and a dog, horse, lion, lizard, or other animal may be the "patient." Appropriate steps may be added or removed by the veterinarian as will be appreciated by those skilled in the art.

Figure 94:
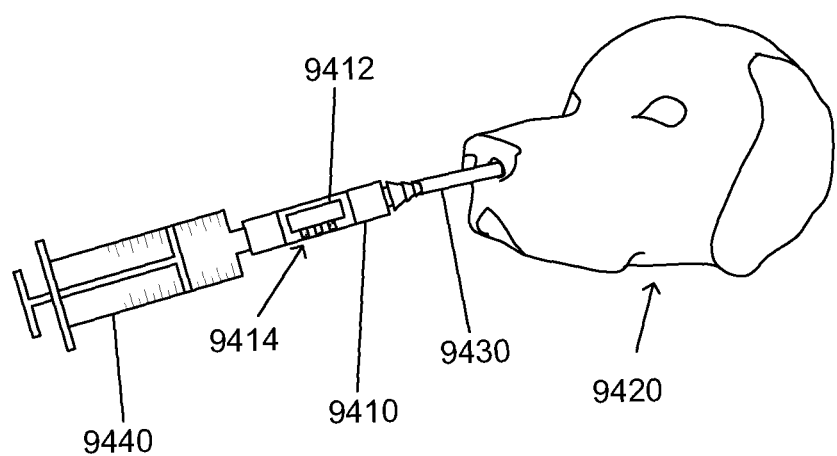
FIG. 94 is a side elevation view of a further implementation of a fluid characteristic measurement apparatus configured for use in a mammal.

FIG. 94 is a side elevation view of a further implementation of a fluid characteristic measurement apparatus 9410 in which certain components are arranged in an alternate configuration. The apparatus 9410 may generally be constructed in a manner similar to the apparatus described above (e.g., as shown in FIGS. 55, 72-73, 75, etc.) with certain variations from those constructions for use with a mammal, for example a canine patient 9420. Canine patient 9420 is shown with a nasogastric tube 9430 that has been placed using techniques known to those skilled in the veterinarian arts. A first end of the fluid characteristic measurement apparatus 9410 is removably engaged with the nasogastric tube 9430. A suction source, such as a syringe 9440, is removably engaged with a second end of the fluid characteristic measurement apparatus 9406. In this implementation, a detection indicator 9412 and a reference indicator 9414 of the apparatus 9410 may be configured for use with the canine patient 9420. For example, the detection indicator 9412 may be configured to provide a color change within a pH range approximately between 1 and 6 and the reference indicator 9414 may be configured with reference samples at pH values of 1.0, 1.5, 2.0, and 3.0. Alternative ranges and values for pH or other fluid characteristics for measurement by the apparatus will be apparent to those skilled in the art.

While the principles of the invention have been described above in connection with specific apparatus and applications, it is to be understood that this description is only an example and is not intended as a limitation on the scope of the invention. The above-described embodiments of the invention are merely examples of ways in which the invention may be carried out. Other ways may also be possible, and are within the scope of the following claims defining the invention.

What is claimed is:

1. An apparatus, comprising:
   a detection indicator configured to display at least one visual indication when in contact with a liquid from a body of a subject, said at least one visual indication representing a value of a characteristic of the body liquid;
   a housing with an interior chamber containing said detection indicator and configured to receive the body liquid and to provide contact between the body liquid and the detection indicator;
   an exoskeletal member into which said housing is nestably disposed;
   wherein the housing has an opening configured to removably engage a conduit adapted for liquid-transfer coupling with the subject so as to enable receiving body liquid from the subject.

2. The apparatus of claim 1 wherein said exoskeletal member is adapted to seal the housing from leaks in that portion of the housing nested in the exoskeletal member.

3. The apparatus of claim 1, further comprising a reference indicator configured to provide a reference visual indication for visual comparison with at least one of said at least one visual indication so as to enable determination of the value of the characteristic of the body liquid by a user.

4. The apparatus of claim 3 wherein the reference indicator is wrapped around at least half of a perimeter of the exoskeletal member.

5. The apparatus of claim 4 wherein at least a portion of the exoskeletal member is substantially optically transparent such that said detection indicator is viewable therethrough; and said reference indicator and said detection indicator are simultaneously viewable.

6. The apparatus of claim 4 wherein the reference indicator is wrapped around the entire perimeter of the exoskeletal member.

7. The apparatus of claim 3 wherein the exoskeletal member is formed as an optically transparent tube, and the reference indicator is disposed on an interior surface of said tube.

8. The apparatus of claim 7 wherein at least a portion of the exoskeletal member is substantially optically transparent such that said both the detection indicator and the reference indicator are simultaneously viewable therethrough.

9. The apparatus of claim 1 further comprising a filter disposed between the opening and the interior chamber.

10. The apparatus of claim 1 further comprising an automatic valve disposed between the opening and the interior chamber to permit liquid communication substantially exclusively in a single direction.

11. The apparatus of claim 1 further comprising an adaptor disposed in an opening of the apparatus in liquid communication with the interior chamber, the adaptor having body with a plurality of conical ribs thereon.

12. The apparatus of claim 11 further comprising a resilient sleeve circumferentially covering at least some of the plurality of conical ribs.

13. An apparatus, comprising:
   a detection indicator configured to display at least one visual indication when in contact with a body fluid, said at least one visual indication representing a value of a characteristic of the body fluid;

a housing with an interior chamber configured to receive the body fluid and to provide contact between the body fluid and the detection indicator;

wherein the housing is configured to removably engage a conduit adapted for fluid-transfer coupling with a patient so as to enable receiving body fluid from the patient; and a manually-operated valve disposed between the conduit and the interior chamber, which valve may be operated to allow or prevent fluid communication therebetween.

14. The apparatus of claim 1 wherein the body liquid is gastric aspirate.

15. The apparatus of claim 1 wherein the opening of the housing is configured to removably engage a nasogastric tube adapted for liquid-transfer coupling with a subject so as to enable receiving body liquid from the subject.

16. An apparatus, comprising:
a detection indicator configured to display at least one visual indication when in contact with a liquid from a body of a subject, said at least one visual indication representing a value of a characteristic of the body liquid;
a first body portion:
a second body portion adapted to mate with the first body portion;
wherein said first body portion and said second body portion are configured when in a mated assembly to form a liquid conduit from a first end of the mated assembly to a second end of the mated assembly:
the first body portion having an interior chamber adapted to house the detection indicator;
the liquid conduit having openings into the interior chamber to allow body liquid communication between the liquid conduit and the interior chamber and provide contact between the body liquid and the detection indicator;
wherein the first body portion comprises a tubular member and the interior chamber is at least partially defined by an interior wall of the tubular member and a panel extending across points on the interior wall.

17. The apparatus of claim 16 wherein the mated assembly is configured to removably engage a conduit adapted for liquid-transfer coupling with the subject so as to enable receiving body liquid from the subject.

18. The apparatus of claim 16 wherein the interior chamber forms a slot for receiving the detection indicator.

19. The apparatus of claim 16 wherein the interior chamber forms a curved slot conforming to the interior wall of the tubular member for receiving the detection indicator.

20. The apparatus of claim 16 wherein the body liquid is gastric aspirate.

21. The apparatus of claim 16 wherein said conduit is a nasogastric tube.

22. A method comprising:
coupling a fluid characteristic indicator to a conduit coupled to a patient source of body fluid so as to enable body fluid transfer between the patient and the fluid characteristic indicator;
aspirating a quantity of body fluid from said patient into said fluid characteristic indicator to saturate the fluid characteristic indicator; and
insufflating air into the fluid characteristic indicator to flush body fluid therefrom.

23. The method of claim 22 further comprising:
before aspirating body fluid from the patient, insufflating a predetermined quantity of air into the conduit.

24. The method of claim 22 further comprising:
further coupling said conduit to suction through a valve; and before coupling the conduit to suction, operating the valve to temporarily disable the suction.

25. The method of claim 24 further comprising: after aspirating body fluid from the patient, operating the valve to enable the suction, whereby the suction substantially prevents body fluid flushed from the fluid characteristic indicator from returning to the patient.

26. A method comprising:
coupling a fluid characteristic indicator to a conduit coupled to a patient source of body fluid, the couplings enabling body fluid transfer between the patient and the fluid characteristic indicator;
aspirating a quantity of body fluid from said patient into said fluid characteristic indicator to saturate the fluid characteristic indicator; and
insufflating air into the fluid characteristic indicator to flush body fluid therefrom, returning to the patient substantially all body fluid obtained therefrom.

27. The method of claim 26 further comprising: before aspirating body fluid from the patient, insufflating a predetermined quantity of air into the conduit.

28. The method of claim 27 further comprising: applying a cap to the conduit.

* * * * *